United States Patent [19]

Barenkamp

[11] Patent Number: 5,876,733
[45] Date of Patent: Mar. 2, 1999

[54] HIGH MOLECULAR WEIGHT SURFACE PROTEINS OF NON-TYPEABLE HAEMOPHILUS

[75] Inventor: Stephen J. Barenkamp, Webster Grove, Mo.

[73] Assignees: St. Louis University; Washington University

[21] Appl. No.: 469,880

[22] Filed: Jun. 6, 1995

Related U.S. Application Data

[63] Continuation of Ser. No. 302,832, filed as PCT/US93/02166 Mar. 16, 1993, Pat. No. 5,603,938.

[30] Foreign Application Priority Data

Mar. 16, 1992 [GB] United Kingdom .................. 9205704

[51] Int. Cl.$^6$ ................................................ A61K 39/102
[52] U.S. Cl. .................... 424/256.1; 424/193.1; 424/197.11; 424/185.1; 530/350; 536/23.1; 536/23.7
[58] Field of Search ............................ 424/256.1, 197.11, 424/193.1, 185.1; 530/350; 536/23.1, 23.7

[56] References Cited

PUBLICATIONS

Barenkamp et al. 1990. Ped. Infect. Dis. 9(5):333–339.
Barenkamp et al., Abstract 983, Pediatric Research, vol. 27.
Caputa et al., J. Clin. Microbiol., 1991, 29(11):2418–2423.
Scheerson et al. 1984. Infect. Immun. 45(3):582–591.
Barenkamp et al. 1992. Infect. Immun. 60(4):1302–1313.
Pediatric Infectious Disease Journal, vol. 9, No. 5, issued May 1990, S.J. Barenkamp et al., "Development of Serum Bactericidal Activity Following Nontypable *Haemophilus influenzae* Acute Otitis Media", pp. 333–339, see entire document.
Journal of Clinical Microbiology, vol. 29, No. 11, issued Nov. 1991, A.C. Caputa et al., "110 Kilodalton Recombinant Protein which is Immunoreactive with Sera from Humans, Dogs, and Horses with Lyme Borreliosis", pp. 2418–2423, see entire document.
Joint Meeting of the American Pediatric Society and the Society for Pediatric Research, 07–10 May 1990, S.J. Barenkamp, "Cloning and Expression of Genes for Nontypable *Haemophilus influenzae* (NTHI) High Molecular Weight (HMW) Outer Membrane Proteins which are Targets of Bactericidal Antibody", Abstract 983, Pediatric Research, vol. 27, (4 part 2).
The Journal of Infectious Diseases, vol. 165 (Suppl.), issued Aug. 1992, S.J.Barenkamp, "Outer Membrane Protein and Lipopolysaccharides of Nontypeable *Haemophilus influenzae*", pp. S181–S184, see entire document.

Infection and Immunity, vol. 60(40, issued Apr. 1992, S.J.Barenkamp et al., Cloning, Expression and DNA Sequence Analysis of Genes Encoding Nontypable *Haemophilus influenzae* High–Molecular–Weight Surface–Exposed Proteins Related to Filamentous Hemagglutinin of *Bordetella pertussis* pp. 1302–1313, see entire document.

Infection and Immunity, vol. 56(l), issued Jan. 1988, E.J. Hansen, Immune Enhancement of Pulmonary Clearance on Nontypable *Haemophilus influenzae*, pp. 182–190, see entire document, especially Figures 3 and 4.

Infection and Immunity, vol. 52(2), issued May 1986, S.J. Barenkamp, "Protection by Serum Antibodies in Experimental Nontypable *Haemophilus influenzae* Otitis Media", pp. 572–578, see Figures 1 and 2.

Proceedings of the National Academy of Sciences USA, vol. 80, issued Mar. 1983, R.A. Young et al, "Efficient Isolation of Genes by Using Antibody Probes", pp. 1194–1198, see entire document.

Infection and Immunity, vol. 45(3), issued Sep. 1984, R. Schneerson et al, "Serum Antibody Responses of Juvenile and Infant Rhesus Monkeys Injected with *Haemophilus influenzae* Type b and Pneumococcus Type 6A Capsular Polysaccharide–Protein Conjugates", pp. 582–591, see entire document.

Journal of Molecular Biology, vol. 157, issued 1982, J. Kyte et al, "A Simple Method for Displaying the Hydropathic Character of a Protein", pp. 105–132, see entire document.

Proceedings of the National Academy of Sciences, vol. 78(6), issued Jun. 1981, T.P.Hopp et al, "Prediction of Protein Antigenic Determinants from Amino Acid Sequences", pp. 3824–3828, see entire document.

Pediatr. Infect. Dis. J., 9: 333–339, 1990, Stephen J. Barenkamp and Frank F. Bodor, "Development of Serum Bacterial Activity Following Nontypable *Haemophilus influenzae* Acute Otitis Media".

*Primary Examiner*—James C. Housel
*Assistant Examiner*—Jennifer Shaver
*Attorney, Agent, or Firm*—Shoemaker and Mattare, Ltd.

[57] ABSTRACT

High molecular weight surfaces proteins of non-typeable *Haemophilus influenzae* which exhibit immunogenic properties and genes encoding the same are described. Specifically, genes coding for two immunodominant high molecular weight proteins, HMW1 and HMW2, have been cloned, expressed and sequenced, while genes coding for high molecular proteins HMW3 and HMW4 have been cloned, expressed and partially sequenced.

2 Claims, 68 Drawing Sheets

FIG. 1A. DNA SEQUENCE OF HIGH MOLECULAR WEIGHT PROTEIN I (HMW1)

```
  1  ACAGCGTTCT CTTAATACTA GTACAAACCC ACAATAAAAT ATGACAAACA
 51  ACAATTACAA CACCTTTTTT GCAGTCTATA TGCAAATATT TTAAAAAATA
101  GTATAAATCC GCCATATAAA ATGGTATAAT CTTTCATCTT TCATCTTTCA
151  TCTTTCATCT TTCATCTTTC ATCTTTCATC TTTCATCTTT CATCTTTCAT
201  CTTTCATCTT TCATCTTTCA TCTTTCATCT TTCATCTTTC ACATGCCCTG
251  ATGAACCCAG GGAAGGGAGG GAGGGGCAAG AATGAAGAGG GAGCTGAACG
301  AACGCAAATG ATAAAGTAAT TTAATTGTTC AACTAACCTT AGGAGAAAAT
351  ATGAACAAGC TATATCGTCT CAAATTCAGC AAACGCCTGA ATGCTTTGGT
401  TGCTGTGTCT GAATTGGCAC GGGGTTGTGA CCATTCCACA GAAAAAGGCA
451  GCGAAAAACC TGCTCGCATG AAAGTGCGTC ACTTAGCGTT AAAGCCACTT
501  TCCGCTATGT TACTATCTTT AGGTGTAACA TCTATTCCAC AATCTGTTTT
551  AGCAAGCGGC TTACAAGGAA TGGATGTAGT ACACGGCACA GCCACTATGC
601  AAGTAGATGG TAATAAAACC ATTATCCGCA ACAGTGTTGA CGATATCATT
651  AATTGGAAAC AATTTAACAT CGACCAAAAT GAAATGGTGC AGTTTTTACA
701  AGAAAACAAC AACTCCGCCG TATTCAACCG TGTTACATCT AACCAAATCT
```

FIG. 1B.

```
 751  CCCAATTAAA  AGGGATTTTA  GATTCTAACG  GACAAGTCTT  TTTAATCAAC
 801  CCAAATGGTA  TCACAATAGG  TAAAGACGCA  ATTATTAACA  CTAATGGCTT
 851  TACGGCTTCT  ACGCTAGACA  TTTCTAACGA  AAACATCAAG  GCGCGTAATT
 901  TCACCTTCGA  GCAAACCAAA  GATAAAGCGC  TCGCTGAAAT  TGTGAATCAC
 951  GGTTTAATTA  CTGTCGGTAA  AGACGGCAGT  GTAAATCTTA  TTGGTGGCAA
1001  AGTGAAAAAC  GAGGGTGTGA  TTAGCGTAAA  TGGTGGCAGC  ATTTCTTTAC
1051  TCGCAGGGCA  AAAAATCACC  ATCAGCGATA  TAATAAACCC  AACCATTACT
1101  TACAGCATTG  CCGCGCCTGA  AAATGAAGCG  GTCAATCTGG  GCGATATTTT
1151  TGCCAAAGGC  GGTAACATTA  ATGTCCGTGC  TGCCACTATT  CGAAACCAAG
1201  GTAAACTTTC  TGCTGATTCT  GTAAGCAAAG  ATAAAAGCGG  CAATATTGTT
1251  CTTTCCGCCA  AAGAGGGTGA  AGCGGAAATT  GGCGGTGTAA  TTTCCGCTCA
1301  AAATCAGCAA  GCTAAAGGCG  GCAAGCTGAT  GATTACAGGC  GATAAAGTCA
1351  CATTAAAAAC  AGGTGCAGTT  ATCGACCTTT  CAGGTAAAGA  AGGGGAGAA
1401  ACTTACCTTG  GCGGTGACGA  GCGCGGCGAA  GGTAAAAAGG  GCATTCAATT
1451  AGCAAAGAAA  ACCTCTTTAG  AAAAAGGCTC  AACCATCAAT  GTATCAGGCA
1501  AAGAAAAAGG  CGGACGCGCT  ATTGTGTGGG  GCGATATTGC  GTTAATTGAC
```

FIG. 1C.

```
1551  GGCAATATTA ACGCTCAAGG TAGTGGTGAT ATCGCTAAAA CCGGTGGTTT
1601  TGTGGAGACG TCGGGGCATG ATTTATTCAT CAAAGACAAT GCAATTGTTG
1651  ACGCCAAAGA GTGGTTGTTA GACCCGGATA ATGTATCTAT TAATGCAGAA
1701  ACAGCAGGAC GCAGCAATAC TTCAGAAGAC GATGAATACA CGGGATCCGG
1751  GAATAGTGCC AGCACCCCAA AACGAAACAA AGAAAAGACA ACATTAACAA
1801  ACACAACTCT TGAGAGTATA CTAAAAAAAG GTACCTTTGT TAACATCACT
1851  GCTAATCAAC GCATCTATGT CAATAGCTCC ATTAATTTAT CCAATGGCAG
1901  CTTAACTCTT TGGAGTGAGG GTCGGAGCGG TGGCGGCGTT GAGATTAACA
1951  ACGATATTAC CACCGGTGAT GATACCAGAG GTGCAAACTT AACAATTTAC
2001  TCAGGCGGCT GGGTTGATGT TCATAAAAAT ATCTCACTCG GGGCGCAAGG
2051  TAACATAAAC ATTACAGCTA AACAAGATAT CGCCCTTTGAG AAAGGAAGCA
2101  ACCAAGTCAT TACAGGTCAA GGGACTATTA CCTCAGGCAA TCAAAAGGT
2151  TTTAGATTTA ATAATGTCTC TCTAAACGGC ACTGGCAGCG GACTGCAATT
2201  CACCACTAAA AGAACCAATA AATACGCTAT CACAAATAAA TTTGAAGGGA
2251  CTTTAAATAT TTCAGGGAAA GTGAACATCT CAATGGTTTT ACCTAAAAAT
2301  GAAAGTGGAT ATGATAAATT CAAAGGACGC ACTTACTGGA ATTTAACCTC
```

FIG. 1D.

| | | | | | |
|---|---|---|---|---|---|
| 2351 | CTTAAATGTT | TCCGAGAGTG | GCGAGTTTAA | CCTCACTATT | GACTCCAGAG |
| 2401 | GAAGCGATAG | TGCAGGCACA | CTTACCCAGC | CTTATAATTT | AAACGGTATA |
| 2451 | TCATTCAACA | AAGACACTAC | CTTTAATGTT | GAACGAAATG | CAAGAGTCAA |
| 2501 | CTTTGACATC | AAGGCACCAA | TAGGGATAAA | TAAGTATTCT | AGTTTGAATT |
| 2551 | ACGCATCATT | TAATGGAAAC | ATTTCAGTTT | CGGGAGGGGG | GAGTGTTGAT |
| 2601 | TTCACACTTC | TCGCCTCATC | CTCTAACGTC | CAAACCCCCG | GTGTAGTTAT |
| 2651 | AAATTCTAAA | TACTTTAATG | TTTCAACAGG | GTCAAGTTTA | AGATTAAAA |
| 2701 | CTTCAGGCTC | AACAAAAACT | GGCTTCTCAA | TAGAGAAAGA | TTTAACTTTA |
| 2751 | AATGCCACCG | GAGGCAACAT | AACACTTTTG | CAAGTTGAAG | GCACCGATGG |
| 2801 | AATGATTGGT | AAAGGCATTG | TAGCCAAAAA | AAACATAACC | TTTGAAGGAG |
| 2851 | GTAACATCAC | CTTTGGCTCC | AGGAAAGCCG | TAACAGAAAT | CGAAGGCAAT |
| 2901 | GTTACTATCA | ATAACAACGC | TAACGTCACT | CTTATCGGTT | CGGATTTGA |
| 2951 | CAACCATCAA | AAACCTTTAA | CTATTAAAAA | AGATGTCATC | ATTAATAGCG |
| 3001 | GCAACCTTAC | CGCTGGAGGC | AATATTGTCA | ATATAGCCGG | AAATCTTACC |
| 3051 | GTTGAAAGTA | ACGCTAATTT | CAAAGCTATC | ACAAATTTCA | CTTTTAATGT |
| 3101 | AGGCGGCTTG | TTTGACAACA | AAGGCAATTC | AAATATTTCC | ATTGCCAAAG |
| 3151 | GAGGGGCTCG | CTTTAAAGAC | ATTGATAATT | CCAAGAATTT | AAGCATCACC |

FIG. 1E.

```
3201 ACCAACTCCA GCTCCACTTA CCGCACTATT ATAAGCGGCA ATATAACCAA
3251 TAAAAACGGT GATTTAAATA TTACGAACGA AGGTAGTGAT ACTGAAATGC
3301 AAATTGGCGG CGATGTCTCG CAAAAAGAAG GTAATCTCAC GATTTCTTCT
3351 GACAAAATCA ATATTACCAA ACAGATAACA ATCAAGGCAG GTGTTGATGG
3401 GGAGAATTCC GATTCAGACG CGACAAACAA TGCCAATCTA ACCATTAAAA
3451 CCAAAGAATT GAAATTAACG CAAGACCTAA ATATTTCAGG TTTCAATAAA
3501 GCAGAGATTA CAGCTAAAGA TGGTAGTGAT TTAACTATTG GTAACACCAA
3551 TAGTGCTGAT GGTACTAATG CCAAAAAAGT AACCTTTAAC CAGGTTAAAG
3601 ATTCAAAAAT CTCTGCTGAC GGTCACAAGG TGACACTACA CAGCAAAGTG
3651 GAAACATCCG GTAGTAATAA CAACACTGAA GATAGCAGTG ACAATAATGC
3701 CGGCTTAACT ATCGATGCAA AAAATGTAAC AGTAAACAAC AATATTACTT
3751 CTCACAAAGC AGTGAGCATC TCTGCGACAA GTGGAGAAAT TACCACTAAA
3801 ACAGGTACAA CCATTAACGC AACCACTGGT AACGTGGAGA TAACCGCTCA
3851 AACAGGTAGT ATCCTAGGTG GAATTGAGTC CAGCTCTGGC TCTGTAACAC
3901 TTACTGCAAC CGAGGGCGCT CTTGCTGTAA GCAATATTTC GGGCAACACC
3951 GTTACTGTTA CTGCAAATAG CGGTGCATTA ACCACTTTGG CAGGCTCTAC
```

FIG. 1F.

```
4001 AATTAAAGGA ACCGAGAGTG TAACCACTTC AAGTCAATCA GGCGATATCG
4051 GCGGTACGAT TTCTGGTGGC ACAGTAGAGG TTAAAGCAAC CGAAAGTTTA
4101 ACCACTCAAT CCAATTCAAA AATTAAAGCA ACAACAGGCG AGGCTAACGT
4151 AACAAGTGCA ACAGGTACAA TTGGTGGTAC GATTTCCGGT AATACGGTAA
4201 ATGTTACGGC AAACGCTGGC GATTTAACAG TTGGGAATGG CGCAGAAATT
4251 AATGCGACAG AAGGAGCTGC AACCTTAACT ACATCATCGG GCAAATTAAC
4301 TACCGAAGCT AGTTCACACA TTACTTCAGC CAAGGGTCAG GTAAATCTTT
4351 CAGCTCAGGA TGGTAGCGTT GCAGGAAGTA TTAATGCCGC CAATGTGACA
4401 CTAAATACTA CAGGCACTTT AACTACCGTG AAGGGTTCAA ACATTAATGC
4451 AACCAGCGGT ACCTTGGTTA TTAACGCAAA AGACGCTGAG CTAAATGGCG
4501 CAGCATTGGG TAACCACACA GTGGTAAATG CAACCAACGC AAATGGCTCC
4551 GGCAGCGTAA TCGCGACAAC CTCAAGCAGA GTGAACATCA CTGGGGATTT
4601 AATCACAATA AATGGATTAA ATATCATTTC AAAAAACGGT ATAAACACCG
4651 TACTGTTAAA AGGCGTTAAA ATTGATGTGA AATACATTCA ACCGGGTATA
4701 GCAAGCGTAG ATGAAGTAAT TGAAGCGAAA CGCATCCCTTG AGAAGGTAAA
4751 AGATTTATCT GATGAAGAAA GAGAAGCGTT AGCTAAACTT GGAGTAAGTG
4801 CTGTACGTTT TATTGAGCCA AATAATACAA TTACAGTCGA TACACAAAAT
```

FIG. 1G.

```
4851 GAATTTGCAA CCAGACCATT AAGTCGAATA GTGATTTCTG AAGGCAGGGC
4901 GTGTTCTCA  AACAGTGATG GCGCGACGGT GTGCGTTAAT ATCGCTGATA
4951 ACGGGCGGTA GCGGTCAGTA ATTGACAAGG TAGATTTCAT CCTGCAATGA
5001 AGTCATTTTA TTTTCGTATT ATTTACTGTG TGGGTTAAAG TTCAGTACGG
5051 GCTTTACCCA TCTTGTAAAA AATTACGGAG AATACAATAA AGTATTTTTA
5101 ACAGGTTATT ATTATG
```

FIG. 2A. AMINO ACID SEQUENCE OF HIGH MOLECULAR WEIGHT PROTEIN I

```
  1  MNKIYRLKFS  KRLNALVAVS  ELARGCDHST  EKGSEKPARM  KVRHLALKPL
 51  SAMLLSLGVT  SIPQSVLASG  LQGMDVVHGT  ATMQVDGNKT  IIRNSVDAII
101  NWKQFNIDQN  EMVQFLQENN  NSAVFNRVTS  NQISQLKGIL  DSNGQVFLIN
151  PNGITIGKDA  IINTNGFTAS  TLDISNENIK  ARNFTFEQTK  DKALAEIVNH
201  GLITVGKDGS  VNLIGGKVKN  EGVISVNGGS  ISLLAGQKIT  ISDIINPTIT
251  YSIAAPENEA  VNLGDIFAKG  GNINVRAATI  RNQGKLSADS  VSKDKSGNIV
301  LSAKEGEAEI  GGVISAQNQQ  AKGGKLMITG  DKVTLKTGAV  IDLSGKEGGE
351  TYLGGDERGE  GKNGIQLAKK  TSLEKGSTIN  VSGKEKGGRA  IVWGDIALID
401  GNINAQGSGD  IAKTGGFVET  SGHDLFIKDN  AIVDAKEWLL  DFDNVSINAE
451  TAGRSNTSED  DEYTGSGNSA  STPKRNKEKT  TLTNTTLESI  LKKGTFVNIT
501  ANQRIYVNSS  INLSNGSLTL  WSEGRSGGGV  EINNDITTGD  DTRGANLTIY
551  SGGWVDVHKN  ISLGAQNIN   ITAKQDIAFE  KGSNQVITGQ  GTITSGNQKG
601  FRFNNVSLNG  TGSGLQFTTK  RTNKYAITNK  FEGTLNISGK  VNISMVLPKN
651  ESGYDKFKGR  TYWNLTSLNV  SESGEFNLTI  DSRGSDSAGT  LTQPYNLNGI
701  SFNKDTTFNV  ERNARVNFDI  KAPIGINKYS  SLNYASFNGN  ISVSGGGSVD
```

FIG. 2B.

```
 751 FTLLASSSNV QTPGVVINSK YFNVSTGSSL RFKTSGSTKT GFSIEKDLTL
 801 NATGGNITLL QVEGTDGMIG KGIVAKKNIT FEGGNITFGS RKAVTEIEGN
 851 VTINNNANVT LIGSDFDNHQ KPLTIKKDVI INSGNLTAGG NIVNIAGNLT
 901 VESNANFKAI TNFTFNVGGL FDNKGNSNIS IAKGGARFKD IDNSKNLSIT
 951 TNSSSTYRTI ISGNITNKNG DLNITNEGSD TEMQIGGDVS QKEGNLTISS
1001 DKINITKQIT IKAGVDGENS DSDATNNANL TIKTKELKLT QDLNISGFNK
1051 AEITAKDGSD LTIGNTNSAD GTNAKKVTFN QVKDSKISAD GHKVTLHSKV
1101 ETSGSNNNTE DSSDNNAGLT IDAKNVTVNN NITSHKAVSI SATSGEITTK
1151 TGTTINATTG NVEITAQTGS ILGGIESSSG SVTLTATEGA LAVSNISGNT
1201 VTVTANSGAL TTLAGSTIKG TESVTTSSQS GDIGGTISGG TVEVKATESL
1251 TTQSNSKIKA TTGEANVTSA TGTIGGTISG NTVNVTANAG DLTVGNGAEI
1301 NATEGAATLT TSSGKLTTEA SSHITSAKGQ VNLSAQDGSV AGSINAANVT
1351 LNTTGTLTTV KGSNINATSG TLVINAKDAE LNGAALGNHT VVNATNANGS
1401 GSVIATTSSR VNITGDLITI NGLNIISKNG INTVLLKGVK IDVKYIQPGI
1451 ASVDEVIEAK RILEKVKDLS DEEREALAKL GVSAVRFIEP NNTITVDTQN
1501 EFATRPLSRI VISEGRACFS NSDGATVCVN IADNGR
```

FIG. 3A. AMINO ACID SEQUENCE OF HIGH MOLECULAR WEIGHT PROTEIN II (HMw2)

```
  1  TAAATATACA AGATAATAAA AATAAATCAA GATTTTTGTG ATGACAAACA
 51  ACAATTACAA CACCTTTTTT GCAGTCTATA TGCAAATATT TTAAAAAAAT
101  AGTATAAATC CGCCATATAA AATGGTATAA TCTTTCATCT TTCATCTTTA
151  ATCTTTCATC TTTCATCTTT CATCTTTCAT ATCTTTCATC TCATCTTTCA
201  TCTTTCATCT TTCATCTTTC ATCTTTCATC TTTCATCTTT CACATGAAAT
251  GATGAACCGA GGGAAGGGAG GGAGGGGCAA GAATGAAGAG GGAGCTGAAC
301  GAACGCAAAT GATAAAGTAA TTTAATTGTT CAACTAACCT TAGGAGAAAA
351  TATGAACAAG ATATATCGTC TCAAATTCAG CAAACGCCTG AATGCTTTGG
401  TTGCTGTGTC TGAATTGGCA CGGGGTGTG ACCATTCCAC AGAAAAAGGC
451  TTCCGCTATG TTACTATCTT TAGGTGTAAC CACTTAGCGT TAAAGCCACT
501  TTCCGCTATG TTACTATCTT TAGGTGTAAC ATCTATTCCA CAATCTGTTT
551  TAGCAAGCGG CTTACAAGGA ATGGATGTAG TACACGGCAC AGCCACTATG
601  CAAGTAGATG GTAATAAAAC CATTATCCGC AACAGTGTTG ACGCTATCAT
651  TAATTGGAAA CAATTTAACA TCGACCAAAA TGAAATGGTG CAGTTTTTAC
701  AAGAAAACAA CAACTCCGCC GTATTCAACC GTGTTACATC TAACCAAATC
```

FIG. 3B.

```
 751  TCCCAATTAA AAGGGATTTT AGATTCTAAC GGACAAGTCT TTTTAATCAA
 801  CCCAAATGGT ATCACAATAG GTAAAGACGC AATTATTAAC ACTAATGGCT
 851  TTACGGCTTC TACGCTAGAC ATTTCTAACG AAAACATCAA GGCGCGTAAT
 901  TTCACCTTCG AGCAAACCAA AGATAAAGCG CTCGCTGAAA TTGTGAATCA
 951  CGGTTTAATT ACTGTCGGTA AAGACGGCAG TGTAAATCTT ATTGGTGGCA
1001  AAGTGAAAAA CGAGGGTGTG ATTAGCGTAA ATGGTGGCAG CATTTCTTTA
1051  CTCGCAGGGC AAAAAATCAC CATCAGCGAT ATAATAAACC CAACCATTAC
1101  TTACAGCATT GCCCGCGCCTG AAAATGAAGC GGTCAATCTG GGCGATATTT
1151  TTGCCAAAGG CGGTAACATT AATGTCCGTG CTGCCACTAT TCGAAACCAA
1201  GGTAAACTTT CTGCTGATTC TGTAAGCAAA GATAAAAGCG GCAATATTGT
1251  TCTTTCCGCC AAAGAGGGTG AAGCGGAAAT TGGCGGTGTA ATTTCCGCTC
1301  AAAATCAGCA AGCTAAAGGC GGCAAGCTGA TGATTACAGG CGATAAAGTC
1351  ACATTAAAAA CAGGTGCAGT TATCGACCTT TCAGGTAAAG AAGGGGAGA
1401  AACTTACCTT GGCGGTGACG AGCGCGGCGA AGGTAAAAAC GGCATTCAAT
1451  TAGCAAAGAA AACCTCTTTA GAAAAAGGCT CAACCATCAA TGTATCAGGC
1501  AAAGAAAAAG GCGGACGCGC TATTGTGTGG GGCGATATTG CGTTAATTGA
```

FIG. 3C.

```
1551  CGGCAATATT  AACGCTCAAG  GTAGTGGTGA  TATCGCTAAA  ACCGGTGTT
1601  TTGTGGAGAC  ATCGGGGCAT  TATTTATCCA  TTGACAGCAA  TGCAATTGTT
1651  AAAACAAAAG  AGTGGTTGCT  AGACCCTGAT  GATGTAACAA  TTGAAGCCGA
1701  AGACCCCCTT  CGCAATAATA  CCGGTATAAA  TGATGAATTC  CCAACAGGCA
1751  CCGGTGAAGC  AAGCGACCCT  AAAAAAAATA  GCGAACTCAA  AACAACGCTA
1801  ACCAATACAA  CTATTTCAAATTATCTGAAA  AACGCCTGGA  CAATGAATAT
1851  AACGGCATCA  AGAAAACTTA  CCGTTAATAG  CTCAATCAAC  ATCGGAAGCA
1901  ACTCCCACTT  AATTCTCCAT  AGTAAAGGTC  AGCGTGGCGG  AGGCGTTCAG
1951  ATTGATGGAG  ATATTACTTC  TAAAGGCGGA  AATTTAACCA  TTTATTCTGG
2001  CGGATGGGTT  GATGTTCATA  AAAATATTAC  GCTTGATCAG  GGTTTTTAA
2051  ATATTACCGC  CGCTTCCGTA  GCTTTTGAAG  GTGGAAATAA  CAAAGCACGC
2101  GACGCGGCAA  ATGCTAAAAT  TGTCGCCCAG  GGCACTGTAA  CCATTACAGG
2151  AGAGGGAAAA  GATTTCAGGG  CTAACAACGT  ATCTTTAAAC  GGAACGGGTA
2201  AAGGTCTGAA  TATCATTTCA  TCAGTGAATA  ATTTAACCCA  CAATCTTAGT
2251  GGCACAATTA  ACATATCTGG  GAATATAACA  ATTAACCAAA  CTACGAGAAA
2301  GAACACCTCG  TATTGGCAAA  CCAGCCATGA  TTCGCACTGG  AACGTCAGTG
2351  CTCTTAATCT  AGAGACAGGC  GCAAATTTTA  CCTTTATTAA  ATACATTTCA
```

FIG. 3D.

```
2401  AGCAATAGCA  AAGGCTTAAC  AACACAGTAT  AGAAGCTCTG  CAGGGGTGAA
2451  TTTTAACGGC  GTAAATGGCA  ACATGTCATT  CAATCTCAAA  GAAGGAGCGA
2501  AAGTTAATTT  CAAATTAAAA  CCAAACGAGA  ACATGAACAC  AAGCAAACCT
2551  TTACCAATTC  GGTTTTTAGC  CAATATCACA  GCCACTGGTG  GGGCTCTGT
2601  TTTTTTGAT  ATATATGCCA  ACCATTCTGG  CAGAGGGCT  GAGTTAAAAA
2651  TGAGTGAAAT  TAATATCTCT  AACGGCGCTA  ATTTTACCTT  AAATTCCCAT
2701  GTTCGCGGCG  ATGACGCTTT  TAAAATCAAC  AAAGACTTAA  CCATAAATGC
2751  AACCAATTCA  AATTTCAGCC  TCAGACAGAC  GAAAGATGAT  TTTTATGACG
2801  GGTACGCACG  CAATGCCATC  AATTCAACCT  ACAACATATC  CATTCTGGGC
2851  GGTAATGTCA  CCCTTGGTGG  ACAAAACTCA  AGCAGCAGCA  TTACGGGGAA
2901  TATTACTATC  GAGAAAGCAG  CAAATGTTAC  GCTAGAAGCC  AATAACGCCC
2951  CTAATCAGCA  AAACATAAGG  GATAGAGTTA  TAAAACTTGG  CAGCTTGCTC
3001  GTTAATGGGA  GTTTAAGTTT  AACTGGCGAA  AATGCAGATA  TTAAAGGCAA
3051  TCTCACTATT  TCAGAAAGCG  CCACTTTTAA  AGGAAAGACT  AGAGATACCC
3101  TAAATATCAC  CGGCAATTTT  ACCAATAATG  GCACTGCCGA  AATTAATATA
3151  ACACAAGGAG  TGGTAAAACT  TGGCAATGTT  ACCAATGATG  GTGATTTAAA
```

FIG. 3E.

```
3201  CATTACCACT CACGCTAAAC GCAACCAAAG AAGCATCATC GGCGGAGATA
3251  TAATCAACAA AAAAGGAAGC TTAAATATTA CAGACAGTAA TAATGATGCT
3301  GAAATCCAAA TTGGCGGCAA TATCTCGCAA AAAGAAGGCA ACCTCACGAT
3351  TTCTTCCGAT AAAATTAATA TCACCAAACA GATAACAATC AAAAAGGGTA
3401  TTGATGGAGA GGACTCTAGT TCAGATGCGA CAAGTAATGC CAACCTAACT
3451  ATTAAAACCA AAGAATTGAA ATTGACAGAA GACCTAAGTA TTTCAGGTTT
3501  CAATAAAGCA GAGATTACAG CCAAAGATGG TAGAGATTTA ACTATTGGCA
3551  ACAGTAATGA CGGTAACAGC GGTGCCGAAG CCAAAAACAGT AACTTTTAAC
3601  AATGTTAAAG ATTCAAAAAT CTCTGCTGAC GGTCACAATG TGACACTAAA
3651  TAGCAAAGTG AAAACATCTA GCAGCAATGG CGGACGTGAA AGCAATAGCG
3701  ACAACGATAC CGGCTTAACT ATTACTGCAA AAAATGTAGA AGTAAACAAA
3751  GATATTACTT CTCTCAAAAC AGTAAATATC ACCGCGTCGG AAAAGGTTAC
3801  CACCACAGCA GGCTCGACCA TTAACGCAAC AAATGGCAAA GCAAGTATTA
3851  CAACCAAAAC AGGTGATATC AGCGGGTACGA TTTCCGGTAA CACGGTAAGT
3901  GTTAGCGCGA CTGGTGATTT AACCACTAAA TCCGGCTCAA AAATTGAAGC
3951  GAAATCGGGT GAGGCTAATG TAACAAGTGC AACAGGTACA ATTGGCGGTA
```

FIG. 3F.

```
4001 CAATTTCCGG TAATACGGTA AATGTTACGG CAAACGCTGG CGATTAACA
4051 GTTGGGAATG GCGCAGAAAT TAATGCGACA GAAGGAGCTG CAACCTTAAC
4101 CGCAACAGGG AATACCTTGA CTACTGAAGC CGGTTCTAGC ATCACTTCAA
4151 CTAAGGGTCA GGTAGACCTC TTGGCTCAGA ATGGTAGCAT CGCAGGAAGC
4201 ATTAATGCTG CTAATGTGAC ATTAAATACT ACAGGCACCT TAACCACCGT
4251 GGCAGGCTCG GATATTAAAG CAACCAGCGG CACCTTGGTT ATTAACGCAA
4301 AAGATGCTAA GCTAAATGGT GATGCATCAG GTGATAGTAC AGAAGTGAAT
4351 GCAGTCAACG CAAGCGGCTC TGGTAGTGTG ACTGCGGCAA CCTCAAGCAG
4401 TGTGAATATC ACTGGGGATT TAAACACAGT AAATGGGTTA AATATCATTT
4451 CGAAAGATGG TAGAAACACT GTGCGCTTAA GAGGCAAGGA AATTGAGGTG
4501 AAATATATCC AGCCAGGTGT AGCAAGTGTA GAAGAAGTAA TTGAAGCGAA
4551 ACGCGTCCTT GAAAAAGTAA AAGATTATC TGATGAAGAA AGAGAAACAT
4601 TAGCTAAACT TGGTGTAAGT GCTGTACGTT TTGTTGAGCC AAATAATACA
4651 ATTACAGTCA ATACACAAAA TGAATTTACA ACCAGACCGT CAAGTCAAGT
4701 GATAATTTCT GAAGGTAAGG CGTGTTTCTC AAGTGGTAAT GGCGCACGAG
4751 TATGTACCAA TGTTGCTGAC GATGGACAGC CGTAGTCAGT AATTGACAAG
4801 GTAGATTTCA TCCTGCAATG AAGTCATTTT ATTTTCGTAT TATTTACTGT
```

FIG. 3G.

```
4851  GTGGGTTAAA GTTCAGTACG GGCTTTACCC ATCTTGTAAA AAATTACGGA
4901  GAATACAATA AAGTATTTTT AACAGGTTAT TATTATG
```

FIG. 4A. AMINO ACID SEQUENCE OF HIGH MOLECULAR WEIGHT PROTEIN 2

```
  1  MNKIYRLKFS KRLNALVAVS ELARGCDHST EKGSEKPARM KVRHLALKPL
 51  SAMLLSLGVT SIPQSVLASG LQGMDVVHGT ATMQVDGNKT IIRNSVDAII
101  NWKQFNIDQN EMVQFLQENN NSAVFNRVTS NQISQLKGIL DSNGQVFLIN
151  PNGITIGKDA IINTNGFTAS TLDISNENIK ARNFTFEQTK DKALAEIVNH
201  GLITVGKDGS VNLIGGKVKN EGVISVNGGS ISLLAGQKIT ISDIINPTIT
251  YSIAAPENEA VNLGDIFAKG GNINVRAATI RNQGKLSADS VSKDKSGNIV
301  LSAKEGEAEI GGVISAQNQQ AKGGKLMITG DKVTLKTGAV IDLSGKEGGE
351  TYLGGDERGE GKNGIQLAKK TSLEKGSTIN VSGKEKGGRA IVWGDIALID
401  GNINAQGSGD IAKTGGFVET SGHDLFIKDN AIVDAKEWLL DFDNVSINAE
451  DPLRNNTGIN DEFPTGTGEA SDPKKNSELK TTLTNTTISN YLKNAWTMNI
501  TASRKLTVNS SINIGSNSHL ILHSKGQRGG GVQIDGDITS KGGNLTIYSG
551  GWVDVHKNIT LDQGFLNITA ASVAFEGGNN KARDAANAKI VAQGTVTITG
601  EGKDFRANNV SLNGTGKGLN IISSVNNLTH NLSGTINISG NITINQTTRK
651  NTSYWQTSHD SHWNVSALNL ETGANFTFIK YISSNSKGLT TQYRSSAGVN
701  FNGVNGNMSF NLKEGAKVNF KLKPNENMNT SKPLPIRFLA NITATGGGSV
```

FIG. 4B.

```
751  FFDIYANHSG RGAELKMSEI NISNGANFTL NSHVRGDDAF KINKDLTINA
801  TNSNFSLRQT KDDFYDGYAR NAINSTYNIS ILGGNVTLGG QNSSSSITGN
851  ITIEKAANVT LEANNAPNQQ NIRDRVIKLG SLLVNGSLSL TGENADIKGN
901  LTISESATFK GKTRDTLNIT GNFTNNGTAE INITQGVVKL GNVTNDGDLN
951  ITTHAKRNQR SIIGGDIINK KGSLNITDSN NDAEIQIGGN ISQKEGNLTI
1001 SSDKINITKQ ITIKKGIDGE DSSSDATSNA NLTIKTKELK LTEDLSISGF
1051 NKAEITAKDG RDLTIGNSND GNSGAEAKTV TFNNVKDSKI SADGHNVTLN
1101 SKVKTSSSNG GRESNSDNDT GLTITAKNVE VNKDITSLKT VNITASEKVT
1151 TTAGSTINAT NGKASITTKT GDISGTISGN TVSVSATVDL TTKSGSKIEA
1201 KSGEANVTSA TGTIGGTISG NTVNVTANAG DLTVGNGAEI NATEGAATLT
1251 ATGNTLTTEA GSSITSTKGQ VDLLAQNGSI AGSINAANVT LNTTGTLTTV
1301 AGSDIKATSG TLVINAKDAK LNGDASGDST EVNAVNASGS GSVTAATSSS
1351 VNITGDLNTV NGLNIISKDG RNTVRLRGKE IEVKYIQPGV ASVEEVIEAK
1401 RVLEKVKDLS DEERETLAKL GVSAVRFVEP NNTITVNTQN EFTTRPSSQV
1451 IISEGKACFS SGNGARVCTN VADDGQP
```

FIG. 6A.

```
  1 ACAGCGTTCT CTTAATACTA GTACAAACCC ACAATAAAAT ATGACAAACA
 51 ACAATTACAA CACCTTTTTT GCAGTCTATA TGCAAATATT TTAAAAAATA
101 GTATAAATCC GCCATATAAA ATGGTATAAT CTTTCATCTT TCATCTTTCA
151 TCTTTCATCT TTCATCTTTC ATCTTTCATC TTTCATCTTT CATCTTTCAT
201 CTTTCATCTT TCATCTTTCA TCTTTCATCT TTCATCTTTC ACATGAAATG
251 ATGAACCGAG GGAAGGGAGG GAGGGCAAG AATGAAGAGG GAGCTGAACG
301 AACGCAAATG ATAAAGTAAT TTAATTGTTC AACTAACCTT AGGAGAAAAT
351 ATGAACAAGA TATATCGTCT CAAATTCAGC AAACGCCCTGA ATGCTTTGGT
401 TGCTGTGTCT GAATTGGCAC GGGGTTGTGA CCATTCCACA GAAAAAGGCA
451 GCGAAAAACC TGCTCGCATG AAAGTGCGTC ACTTAGCGTT AAAGCCACTT
501 TCCGCTATGT TACTATCTTT AGGTGTAACA TCTATTCCAC AATCTGTTTT
551 AGCAAGCGGC TTACAAGGAA TGGATGTAGT ACACGGCACA GCCACTATGC
601 AAGTAGATGG TAATAAAACC ATTATCCGCA ACAGTGTTGA CGCTATCATT
651 AATTGGAAAC AATTTAACAT CGACCAAAAT GAAATGGTGC AGTTTTTACA
701 AGAAAACAAC AACTCCGCCG TATTCAACCG TGTTACATCT AACCAAATCT
751 CCCAATTAAA AGGGATTTTA GATTCTAACG GACAAGTCTT TTTAATCAAC
```

FIG. 6B.

```
 801 CCAAATGGTA TCACAATAGG TAAAGACGCA ATTATTAACA CTAATGGCTT
 851 TACGGCTTCT ACGCTAGACA TTTCTAACGA AAACATCAAG GCGCGTAATT
 901 TCACCTTCGA GCAAACCAAA GATAAAGCGC TCGCTGAAAT TGTGAATCAC
 951 GGTTTAATTA CTGTCGGTAA AGACGGCAGT GTAAATCTTA TTGGTGGCAA
1001 AGTGAAAAAC GAGGGTGTGA TTAGCGTAAA TGGTGGCAGC ATTTCTTTAC
1051 TCGCAGGGCA AAAAATCACC ATCAGCGATA TAATAAACCC AACCATTACT
1101 TACAGCATTG CCGCGCCTGA AAATGAAGCG GTCAATCTGG GCGATATTTT
1151 TGCCAAAGGC GGTAACATTA ATGTCCGTGC TGCCACTATT CGAAACCAAG
1201 CTTTCCGCCA AAGAGGGTGA AGCCGAAATT GGCGGTGTAA TTTCCGCTCA
1251 AAATCAGCAA GCTAAAGGCG GCAAGCTGAT GATTACAGGC GATAAAGTCA
1301 CATTAAAAAC AGTGCAGTT ATCGACCTTT CAGGTAAAGA AGGGGAGAA
1351 ACTTACCTTG GCGGTGACGA GCGCGGCGAA GGTAAAAACG GCATTCAATT
1401 AGCAAAGAAA ACCTCTTTAG AAAAAGGCTC AACCATCAAT GTATCAGGCA
1451 AAGAAAAAGG CGGACGCGCT ATTGTGTGGG GCGATATTGC GTTAATTGAC
1501 GGCAATATTA ACGCTCAAGG TAGTGGTGAT ATCGCTAAAA CCGGTGGTTT
1551 TGTGGAGACG TCGGGGCATG ATTTATTCAT CAAAGACAAT GCAATTGTTG
```

FIG. 6C.

```
1651  ACGCCAAAGA  GTGGTTGTTA  GACCCGGATA  ATGTATCTAT  TAATGCAGAA
1701  ACAGCAGGAC  GCAGCAATAC  TTCAGAAGAC  GATGAATACA  CGGGATCCGG
1751  GAATAGTGCC  AGCACCCCAA  AACGAAACAA  AGAAAAGACA  ACATTAACAA
1801  ACACAACTCT  TGAGAGTATA  CTAAAAAAAG  GTACCTTTGT  TAACATCACT
1851  GCTAATCAAC  GCATCTATGT  CAATAGCTCC  ATTAATTTAT  CCAATGGCAG
1901  CTTAACTCTT  TGGAGTGAGG  GTCGGAGCGG  TGGCGGCGTT  GAGATTAACA
1951  ACGATATTAC  CACCGGTGAT  GATACCAGAG  GTGCAAACTT  AACAATTTAC
2001  TCAGGCGGCT  GGGTTGATGT  TCATAAAAAT  ATCTCACTCG  GGGCGCAAGG
2051  TAACATAAAC  ATTACAGCTA  AACAAGATAT  CGCCTTTGAG  AAAGGAAGCA
2101  ACCAAGTCAT  TACAGGTCAA  GGGACTATTA  CCTCAGGCAA  TCAAAAAGGT
2151  TTTAGATTTA  ATAATGTCTC  TCTAAACGGC  ACTGGCAGCG  GACTGCAATT
2201  CACCACTAAA  AGAACCAATA  AATACGCTAT  CACAAATAAA  TTTGAAGGGA
2251  CTTTAAATAT  TTCAGGGAAA  GTGAACATCT  CAATGGTTTT  ACCTAAAAAT
2301  GAAAGTGGAT  ATGATAAATT  CAAAGGACGC  ACTTACTGGA  ATTTAACCTC
2351  GAAAGTGGAT  ATGATAAATT  CAAAGGACGC  CCTCACTATT  GACTCCAGAG
2401  GAAGCGATAG  TGCAGGCACA  CTTACCCAGC  CTTATAATTT  AAACGGTATA
2451  TCATTCAACA  AAGACACTAC  CTTTAATGTT  GAACGAAATG  CAAGAGTCAA
```

FIG. 6D.

```
2501  CTTTGACATC  AAGGCACCAA  TAGGGATAAA  TAAGTATTCT  AGTTTGAATT
2551  ACGCATCATT  TAATGGAAAC  ATTTCAGTTT  CGGGAGGGGG  GAGTGTTGAT
2601  TTCACACTTC  TCGCCTCATC  CTCTAACGTC  CAAACCCCCG  GTGTAGTTAT
2651  AAATTCTAAA  TACTTTAATG  TTTCAACAGG  GTCAAGTTTA  AGATTAAAA
2701  CTTCAGGCTC  AACAAAAACT  GGCTTCTCAA  TAGAGAAAGA  TTTAACTTTA
2751  AATGCCACCG  GAGGCAACAT  AACACTTTTG  CAAGTTGAAG  GCACCGATGG
2801  AATGATTGGT  AAAGGCATTG  TAGCCAAAAA  AAACATAACC  TTTGAAGGAG
2851  GTAAGATGAG  GTTTGGCTCC  AGGAAAGCCG  TAACAGAAAT  CGAAGGCAAT
2901  GTTACTATCA  ATAACAACGC  TAACGTCACT  CTTATCGGTT  CGGATTTTGA
2951  CAACCATCAA  AAACCTTTAA  CTATTAAAAA  AGATGTCATC  ATTAATAGCG
3001  GCAACCTTAC  CGCTGGAGGC  AATATTGTCA  ATATAGCCGG  AAATCTTACC
3051  GTTGAAAGTA  ACGCTAATTT  CAAAGCTATC  ACAAATTTCA  CTTTTAATGT
3101  AGGCGGCTTG  TTTGACAACA  AAGGCAATTC  AAATATTTCC  ATTGCCAAAG
3151  GAGGGGCTCG  CTTTAAAGAC  ATTGATAATT  CCAAGAATTT  AAGCATCACC
3201  ACCAACTCCA  GCTCCACTTA  CCGCACTATT  ATAAGCGGCA  ATATAACCAA
3251  TAAAAACGGT  GATTTAAATA  TTACGAACGA  AGGTAGTGAT  ACTGAAATGC
```

FIG. 6E.

```
3301 AAATTGGCGG CGATGTCTCG CAAAAAGAAG GTAATCTCAC GATTTCTTCT
3351 GACAAAATCA ATATTACCAA ACAGATAACA ATCAAGGCAG GTGTTGATGG
3401 GGAGAATTCC GATTCAGACG CGACAAACAA TGCCAATCTA ACCATTAAAA
3451 CCAAAGAATT GAAATTAACG CAAGACCTAA ATATTTCAGG TTTCAATAAA
3501 GCAGAGATTA CAGCTAAAGA TGGTAGTGAT TTAACTATTG GTAACACCAA
3551 TAGTGCTGAT GGTACTAATG CCAAAAAAGT AACCTTTAAC CAGGTTAAAG
3601 ATTCAAAAAT CTCTGCTGAC GGTCACAAGG TGACACTACA CAGCAAAGTG
3651 GAAACATCCG GTAGTAATAA CAACACTGAA GATAGCAGTG ACAATAATGC
3701 CGGCTTAACT ATCGATGCAA AAAATGTAAC AGTAAACAAC AATATTACTT
3751 CTCACAAAGC AGTGAGCATC TCTGCGACAA GTGGAGAAAT TACCACTAAA
3801 ACAGGTACAA CCATTAACGC AACCACTGGT AACGTGGAGA TAACCGCTCA
3851 AACAGGTAGT ATCCTAGGTG GAATTGAGTC CAGCTCTGGC TCTGTAACAC
3901 TTACTGCAAC CGAGGGCGCT CTTGCTGTAA GCAATATTTC GGGCAACACC
3951 GTTACTGTTA CTGCAAATAG CGGTGCATTA ACCACTTTGG CAGGCTCTAC
4001 AATTAAAGGA ACCGAGAGTG TAACCACTTC AAGTCAATCA GGCGATATCG
4051 GCGGTACGAT TTCTGGTGGC ACAGTAGAGG TTAAAGCAAC CGAAAGTTTA
```

FIG. 6F.

```
4101 ACCACTCAAT CCAATTCAAA AATTAAAGCA ACAACAGGCG AGGCTAACGT
4151 AACAAGTGCA ACAGGTACAA TTGGTGGTAC GATTTCCGGT AATACGGTAA
4201 ATGTTACGGC AAACGCTGGC GATTTAACAG TTGGGAATGG CGCAGAAATT
4251 AATGCGACAG AAGGAGCTGC AACCTTAACT ACATCATCGG GCAAATTAAC
4301 TACCGAAGCT AGTTCACACA TTACTTCAGC CAAGGGTCAG GTAAATCTTT
4351 CAGCTCAGGA TGGTAGCGTT GCAGGAAGTA TTAATGCCGC CAATGTGACA
4401 CTAAATACTA CAGGCACTTT AACTACCGTG AAGGGTTCAA ACATTAATGC
4451 AACCAGCGGT ACCTTGGTTA TTAACGCAAA AGACGCTGAG CTAAATGGCG
4501 CAGCATTGGG TAACCACACA GTGGTAAATG CAACCAACGC AAATGGCTCC
4551 GGCAGCGTAA TCGCGACAAC CTCAAGCAGA GTGAACATCA CTGGGGATTT
4601 AATCACAATA AATGGATTAA ATATCATTTC AAAAAACGGT ATAAACACCG
4651 TACTGTTAAA AGGCGTTAAA ATTGATGTGA AATACATTCA ACCGGGTATA
4701 GCAAGCGTAG ATGAAGTAAT TGAAGGCGAAA CGCATCCCTTG AGAAGGTAAA
4751 AGATTTATCT GATGAAGAAA GAGAAGCGTT AGCTAAACTT GGCGTAAGTG
4801 CTGTACGTTT TATTGAGCCA AATAATACAA TTACAGTCGA TACACAAAAT
4851 GAATTTGCAA CCAGACCATT AAGTCGAATA GTGATTTCTG AAGGCAGGGC
4901 GTGTTTCTCA AACAGTGATG GCGCGACGGT GTGCGTTAAT ATCGCTGATA
```

FIG. 6G.

```
4951 ACGGGCGGTA GCGGTCAGTA ATTGACAAGG TAGATTTCAT CCTGCAATGA
5001 AGTCATTTTA TTTTCGTATT ATTTACTGTG TGGGTTAAAG TTCAGTACGG
5051 GCTTTACCCA TCTTGTAAAA AATTACGGAG AATACAATAA AGTATTTTTA
5101 ACAGGTTATT ATTATGAAAA ATATAAAAAG CAGATTAAAA CTCAGTGCAA
5151 TATCAGTATT GCTTGGCCTG GCTTCTTCAT CATTGTATGC AGAAGAAGCG
5201 TTTTTAGTAA AAGGCTTTCA GTTATCTGGT GCACTTGAAA CTTTAAGTGA
5251 AGACGCCCAA CTGTCTGTAG CAAAATCTTT ATCTAAATAC CAAGGCTCGC
5301 AAACTTTAAC AAACCTAAAA ACAGCACAGC TTGAATTACA GGCTGTGCTA
5351 GATAAGATTG AGCCAAATAA GTTGATGTG ATATTGCCAC AACAAACCAT
5401 TACGGATGGC AATATTATGT TTGAGCTAGT CTCGAAATCA GCCGCAGAAA
5451 GCCAAGTTTT TTATAAGGCG AGCCAGGGTT ATAGTGAAGA AAATATCGCT
5501 CGTAGCCTGC CATCTTTGAA ACAAGGAAAA GTGTATGAAG ATGGTCGTCA
5551 GTGGTTCGAT TTGCGTGAAT TCAATATGGC AAAAGAAAAT CCACTTAAAG
5601 TCACTCGCGT GCATTACGAG TTAAACCCTA AAAACAAAAC CTCTGATTTG
5651 GTAGTTGCAG GTTTTTCGCC TTTTGGCAAA ACGCGTAGCT TTGTTTCCTA
5701 TGATAAGTTC GGCGCAAGGG AGTTTAACTA TCAACGTGTA AGTCTAGGTT
```

FIG. 6H.

```
5751 TTGTAAATGC CAATTTGACC GGACATGATG ATGTATTAAA TCTAAACGCA
5801 TTGACCAATG TAAAAGCACC ATCAAAATCT TATGCGGTAG GCATAGGATA
5851 TACTTATCCG TTTTATGATA AACACCAATC CTTAAGTCTT TATACCAGCA
5901 TGAGTTATGC TGATTCTAAT GATATCGACG GCTTACCAAG TGCGATTAAT
5951 CGTAAATTAT CAAAAGGTCA ATCTATCTCT GCGAATCTGA AATGGAGTTA
6001 TTATCTCCCG ACATTAACC TTGGAATGGA AGACCAGTTT AAAATTAATT
6051 TAGGCTACAA CTACCGCCAT ATTAATCAAA CATCCGAGTT AAACACCCTG
6101 GGTGCAACGA AGAAAAAATT TGCAGTATCA GGCGTAAGTG CAGGCATTGA
6151 TGGACATATC CAATTTACCC CTAAAACAAT CTTTAATATT GATTTAACTC
6201 ATCATTATTA CGCGAGTAAA TTACCAGGCT CTTTTGGAAT GGAGCGCATT
6251 GGCGAAACAT TTAATCGCAG CTATCACATT AGCACAGCCA GTTTAGGGTT
6301 GAGTCAAGAG TTTGCTCAAG GTTGGCATTT TAGCAGTCAA TTATCGGGTC
6351 AGTTACTCT ACAAGATATA AGTAGCATAG ATTTATTCTC TGTAACAGGT
6401 ACTTATGGCG TCAGAGGCTT TAAATACGGC GGTGCAAGTG GTGAGCGCGG
6451 TCTTGTATGG CGTAATGAAT TAAGTATGCC AAAATACACC CGCTTTCAAA
6501 TCAGCCCTTA TGCGTTTTAT GATGCAGGTC AGTTCCGTTA TAATAGCGAA
6551 AATGCTAAAA CTTACGGCGA AGATATGCAC ACGGTATCCT CTGCGGGTTT
```

FIG. 6I.

```
6601  AGGCATTAAA  ACCCTCTCCTA  CACAAAACTT  AAGCTTAGAT  GCTTTTGTTG
6651  CTCGTCGCTT  TGCAAATGCC  AATAGTGACA  ATTTGAATGG  CAACAAAAAA
6701  CGCACAAGCT  CACCTACAAC  CTTCTGGGGT  AGATTAACAT  TCAGTTTCTA
6751  ACCCTGAAAT  TTAATCAACT  GGTAAGCGTT  TACAGTCTAT  GTTTATAACT
6801  ATATGCTTTA  CCCGCCAATT  TACAGTCTAT  ACGCAACCCT  GTTTTCATCC
6851  TTATATATCA  AACAAAACTAA  GCAAACCAAG  CAAACCAAGC  AAACCAAGCA
6901  AACCAAGCAA  ACCAAGCAAA  CCAAGCAAAC  CAAGCAAACC  AAGCAAACCA
6951  AGCAAACCAA  GCAAACCAAG  CAAACCAAGC  AAACCAAGCA  ATGCTAAAAA
7001  ACAATTTATA  TGATAAACTA  AAACATACTC  CATACCATGG  CAATACAAGG
7051  GATTTAATAA  TATGACAAAA  GAAAATTTAC  AAAGTGTTCC  ACAAAATACG
7101  ACCGCTTCAC  TTGTAGAATC  AAACAACGAC  CAAACTTCCC  TGCAAATACT
7151  TAAACAACCA  CCCAAACCCA  ACCTATTACG  CCTGGAACAA  CATGTCGCCA
7201  AAAAAGATTA  TGAGCTTGCT  TGCCGCGAAT  TAATGGCGAT  TTTGGAAAAA
7251  ATGGACGCTA  ATTTTGGAGG  CGTTCACGAT  ATTGAATTTG  ACGCACCTGC
7301  TCAGCTGGCA  TATCTACCCG  AAAAACTACT  AATTCATTTT  GCCACTCGTC
7351  TCGCTAAATGC  AATTACAACA  CTCTTTTCCG  ACCCCGAATT  GGCAATTTCC
```

FIG. 6J.

```
7401 GAAGAAGGGG CATTAAAGAT GATTAGCCTG CAACGCTGGT TGACGCTGAT
7451 TTTTGCCTCT TCCCCCTACG TTAACGCAGA CCATATTCTC AATAAATATA
7501 ATATCAACCC AGATTCCGAA GGTGGCTTTC ATTTAGCAAC AGACAACTCT
7551 TCTATTGCTA AATTCTGTAT TTTTTACTTA CCCGAATCCA ATGTCAATAT
7601 GAGTTTAGAT GCGTTATGGG CAGGGAATCA ACAACTTTGT GCTTCATTGT
7651 GTTTTGCGTT GCAGTCTTCA CGTTTTATTG GTACTGCATC TGCGTTTCAT
7701 AAAAGAGCGG TGGTTTTACA GTGGTTTCCT AAAAAACTCG CCGAAATTGC
7751 TAATTTAGAT GAATTGCCTG CAAATATCCT TCATGATGTA TATATGCACT
7801 GCAGTTATGA TTTAGCAAAA AACAAGCACG ATGTTAAGCG TCCATTAAAC
7851 GAACTTGTCC GCAAGCATAT CCTCACGCAA GGATGGCAAG ACCGCTACCT
7901 TTACACCTTA GGTAAAAAGG ACGGCAAACC TGTGATGATG GTACTGCTTG
7951 AACATTTTAA TTCGGGACAT TCGATTTATC GCACGCATTC AACTTCAATG
8001 ATTGCTGCTC GAGAAAAATT CTATTTAGTC GGCTTAGGCC ATGAGGGCGT
8051 TGATAACATA GGTCGAGAAG TGTTTGACGA GTTCTTTGAA ATCAGTAGCA
8101 ATAATATAAT GGAGAGACTG TTTTTTATCC GTAAACAGTG CGAAACTTTC
8151 CAACCCGCAG TGTTCTATAT GCCAAGCATT GGCATGGATA TTACCACGAT
```

FIG. 6K.

```
8201  TTTGTGAGC  AACACTCGGC  TTGCCCCTAT  TCAAGCTGTA  GCCTTGGGTC
8251  ATCCTGCCAC  TACGCATTCT  GAATTTATTG  ATTATGTCAT  CGTAGAAGAT
8301  GATTATGTGG  GCAGTGAAGA  TTGTTTAGC   GAAACCCTTT  TACGCTTACC
8351  CAAAGATGCC  CTACCTTATG  TACCATCTGC  ACTCGCCCCA  CAAAAAGTGG
8401  ATTATGTACT  CAGGGAAAAC  CCTGAAGTAG  TCAATATCGG  TATTGCCGCT
8451  ACCACAATGA  AATTAAACCC  TGAATTTTTG  CTAACATTGC  AAGAAATCAG
8501  AGATAAAGCT  AAAGTCAAAA  TACATTTTCA  TTTCGCACTT  GGACAATCAA
8551  CAGGCTTGAC  ACACCCTTAT  GTCAAATGGT  TTATCGAAAG  CTATTTAGGT
8601  GACGATGCCA  CTGCACATCC  CCACGCACCT  TATCACGATT  ATCTGGCAAT
8651  ATTGCGTGAT  TGCGATATGC  TACTAAATCC  GTTTCCTTTC  GGTAATACTA
8701  ACGGCATAAT  TGATATGGTT  ACATTAGGTT  TAGTTGGTGT  ATGCAAAACG
8751  GGGGATGAAG  TACATGAACA  TATTGATGAA  GGTCTGTTTA  AACGCTTAGG
8801  ACTACCAGAA  TGGCTGATAG  CCGACACACG  AGAAACATAT  ATTGAATGTG
8851  CTTTGCGTCT  AGCAGAAAAC  CATCAAGAAC  GCCTTGAACT  CCGTCGTTAC
8901  ATCATAGAAA  ACAACGGCTT  ACAAAAGCTT  TTTACAGGCG  ACCCTCGTCC
8951  ATTGGGCAAA  ATACTGCTTA  AGAAAACAAA  TGAATGGAAG  CGGAAGCACT
9001  TGAGTAAAAA  ATAACGGTTT  TTTAAAGTAA  AAGTGCGGTT  AATTTTCAAA
```

FIG. 6L.

```
9051 GCGTTTTAAA AACCTCTCAA AAATCAACCG CACTTTTATC TTTATAACGC
9101 TCCCGGCGC TGACAGTTTA TCTCTTTCTT AAAATACCCA TAAAATTGTG
9151 GCAATAGTTG GGTAATCAAA TTCAATTGTT GATACGGCAA ACTAAAGACG
9201 GCGCGTTCTT CGGCAGTCAT C
```

FIG. 7A.

```
  1  CGCCACTTCA ATTTTGGATT GTTGAAATTC AACTAACCAA AAAGTGCGGT
 51  TAAAATCTGT GGAGAAAATA GGTTGTAGTG AAGAACGAGG TAATTGTTCA
101  AAAGGATAAA GCTCTCTTAA TTGGGCATTG GTTGGCGTTT CTTTTTCGGT
151  TAATAGTAAA TTATATTCTG GACGACTATG CAATCCACCA ACAACTTTAC
201  CGTTGGTTTT AAGCGTTAAT GTAAGTTCTT GCTCTTCTTG GCGAATACGT
251  AATCCCATTT TTTGTTTAGC AAGAAAATGA TCGGGATAAT CATAATAGGT
301  GTTGCCCAAA AATAAATTTT GATGTTCTAA AATCATAAAT TTTGCAAGAT
351  ATTGTGGCAA TTCAATACCT ATTTGTGGCG AAATCGCCAA TTTTAATTCA
401  ATTTCTTGTA GCATAATATT TCCCACTCAA ATCAACTGGT TAAATATACA
451  AGATAATAAA AATAAATCAA GATTTTTGTG ATGACAAACA ACAATTACAA
501  CACCTTTTTT GCAGTCTATA TGCAAATATT TTAAAAAAAT AGTATAAATC
551  CGCCATATAA AATGGTATAA TCTTTCATCT TTCATCTTTC ATCTTTCATC
601  TTTCATCTTT CATCTTTCAT CTTTCATCTT TCATCTTTCA TCTTTCATCT
651  TTCATCTTTC ATCTTTCATC TTTCATCTTT CACATGAAAT GATGAACCGA
701  GGGAAGGGAG GGAGGGGCAA GAATGAAGAG GGAGCTGAAC GAACGCAAAT
751  GATAAAGTAA TTTAATTGTT CAACTAACCT TAGGAGAAAA TATGAACAAG
```

FIG. 7B.

```
 801  ATATATCGTC TCAAATTCAG CAAACGCCTG AATGCTTTGG TTGCTGTGTC
 851  TGAATTGGCA CGGGGTTGTG ACCATTCCAC AGAAAAAGGC AGCGAAAAAC
 901  CTGCTCGCAT GAAAGTGCGT CACTTAGCGT TAAAGCCACT TTCCGCTATG
 951  TTACTATCTT TAGGTGTAAC ATCTATTCCA CAATCTGTTT TAGCAAGCGG
1001  CAATTTAACA TCGACCAAAA TGAAATGGTG CAGTTTTTAC AAGAAAACAA
1051  GTAATAAAAC CATTATCCGC AACAGTGTTG ACGCTATCAT TAATTGGAAA
1101  CAATTTAACA TCGACCAAAA TGAAATGGTG CAGTTTTTAC AAGAAAACAA
1151  CAACTCCGCC GTATTCAACC GTGTTACATC TAACCAAATC TCCCAATTAA
1201  AAGGGATTTT AGATTCTAAC GGACAAGTCT TTTTAATCAA CCCAAATGGT
1251  ATCACAATAG GTAAAGACGC AATTATTAAC ACTAATGGCT TTCACCTTCG
1301  TACGCTAGAC ATTTCTAACG AAAACATCAA GGCGCGTAAT TTCACCTTCG
1351  AGCAAACCAA AGATAAAGCG CTCGCTGAAA TTGTGAATCA CGGTTTAATT
1401  ACTGTCGGTA AAGACGGCAG TGTAAATCTT ATTGGTGGCA AAGTGAAAAA
1451  CGAGGGTGTG ATTAGCGTAA ATGGTGGCAG CATTTCTTTA CTCGCAGGGC
1501  AAAAAATCAC CATCAGCGAT ATAATAAACC CAACCATTAC TTACAGCATT
1551  GCCGCGCCTG AAAATGAAGC GGTCAATCTG GGCGATATTT TTGCCAAAGG
```

FIG. 7C.

```
1601  CGGTAACATT  AATGTCCGTG  CTGCCACTAT  TCGAAACCAA  GGTAAACTTT
1651  CTGCTGATTC  TGTAAGCAAA  GATAAAAGCG  GCAATATTGT  TCTTTCCGCC
1701  AAAGAGGGTG  AAGCGGAAAT  TGGCGGTGTA  ATTTCCGCTC  AAAATCAGCA
1751  AGCTAAAGGC  GGCAAGCTGA  TGATTACAGG  CGATAAAGTC  ACATTAAAAA
1801  CAGGTGCAGT  TATCGACCTT  TCAGGTAAAG  AAGGGGGAGA  AACTTACCTT
1851  GGCGGTGACG  AGCGCGGCGA  AGGTAAAAAC  GGCATTCAAT  TAGCAAAGAA
1901  AACCTCTTTA  GAAAAAGGCT  CAACCATCAA  TGTATCAGGC  AAAGAAAAG
1951  GCGGGACGCG  TATTGTGTGG  GGCGATATTG  CGTTAATTGA  CGGCAATATT
2001  AACGCTCAAG  GTAGTGGTGA  TATCGCTAAA  ACCGGTGTT  TTGTGGAGAC
2051  ATCGGGCAT  TATTTATCCA  TTGACAGCAA  TGCAATTGTT  AAAACAAAAG
2101  AGTGGTTGCT  AGACCCTGAT  GATGTAACAA  TTGAAGCCGA  AGACCCCTT
2151  CGCAATAATA  CCGGTATAAA  TGATGAATTC  CCAACAGGCA  CCGGTGAAGC
2201  AAGCGACCCT  AAAAAAAATA  GCGAACTCAA  AACAACGCTA  ACCAATACAA
2251  CTATTTCAAA  TTATCTGAAA  CTCAATCAAC  CAATGAATAT  AACGGCATCA
2301  AGAAAACTTA  CCGTTAATAG  AACGCCTGGA  ATCGGAAGCA  ACTCCCACTT
2351  AATTCTCCAT  AGTAAAGGTC  AGCGTTGGCGG  AGGCGTTCAG  ATTGATGGAG
2401  ATATTACTTC  TAAAGGCGGA  AATTTAACCA  TTTATTCTGG  CGGATGGGTT
```

FIG. 7D.

```
2451  GATGTTCATA AAAATATTAC GCTTGATCAG GGTTTTTTAA ATATTACCGC
2501  CGCTTCCGTA GCTTTTGAAG GTGGAAATAA CAAAGCACGC GACGCGGCAA
2551  ATGCTAAAAT TGTCGCCCAG GGCACTGTAA CCATTACAGG AGAGGGAAAA
2601  GATTTCAGGG CTAACAACGT ATCTTTAAAC GGAACGGGTA AAGGTCTGAA
2651  TATCATTTCA TCAGTGAATA ATTTAACCCA CAATCTTAGT GGCACAATTA
2701  ACATATCTGG GAATATAACA ATTAACCAAA CTACGAGAAA GAACACCTCG
2751  TATTGGCAAA CCAGCCATGA TTCGCACTGG AACGTCAGTG CTCTTAATCT
2801  AGAGACAGGC GCAAATTTTA CCTTTATTAA ATACATTTCA AGCAATAGCA
2851  AAGGCTTAAC AACACAGTAT AGAAGCTCTG CAGGGGTGAA TTTTAACGGC
2901  GTAAATGGCA ACATGTCATT CAATCTCAAA GAAGGAGCGA AAGTTAATTT
2951  CAAATTAAAA CCAAACGAGA ACATGAACAC AAGCAAACCT TTACCAATTC
3001  GGTTTTTAGC CAATATCACA GCCACTGGTG GGGCTCTGT  TTTTTTTGAT
3051  ATATATGCCA ACCATTCTGG CAGAGGGGCT GAGTTAAAAA TGAGTGAAAT
3101  TAATATCTCT AACGGGCTA  ATTTTACCTT AAATTCCCAT GTTCGCGGCG
3151  ATGACGCTTT TAAAATCAAC AAAGACTTAA CCATAAATGC AACCAATTCA
3201  AATTTCAGCC TCAGACAGAC GAAAGATGAT TTTTATGACG GGTACGCACG
```

FIG. 7E.

```
3251  CAATGCCATC  AATTCAACCT  ACAACATATC  CATTCTGGGC  GGTAATGTCA
3301  CCCTTGGTGG  ACAAAACTCA  AGCAGCAGCA  TTACGGGGAA  TATTACTATC
3351  GAGAAAGCAG  CAAATGTTAC  GCTAGAAGCC  AATAACGCCC  CTAATCAGCA
3401  AAACATAAGG  GATAGAGTTA  TAAAACTTGG  CAGCTTGCTC  GTTAATGGGA
3451  GTTTAAGTTT  AACTGGCGAA  AATGCAGATA  TTAAAGGCAA  TCTCACTATT
3501  TCAGAAAGCG  CCACTTTTAA  AGGAAAGACT  AGAGATACCC  TAAATATCAC
3551  CGGCAATTTT  ACCAATAAATG  GCACTGCCGA  AATTAATATA  ACACAAGGAG
3601  TGGTAAAACT  TGGCAATGTT  ACCAATGATG  GTGATTTAAA  CATTACCACT
3651  CACGCTAAAC  GCAACCAAAG  AAGCATCATC  GGCGGAGATA  TAATCAACAA
3701  AAAAGGAAGC  TTAAATATTA  CAGACAGTAA  TAATGATGCT  GAAATCCAAA
3751  TTGGCGGCAA  TATCTCGCAA  AAAGAAGGCA  ACCTCACGAT  TTCTTCCGAT
3801  AAAATTAATA  TCACCAAACA  GATAACAATC  AAAAAGGGTA  TTGATGGAGA
3851  GGACTCTAGT  TCAGATGCGA  CAAGTAATGC  CAACCTAACT  ATTAAAACCA
3901  AAGAATTGAA  ATTGACAGAA  AAAGAAGGCA  GACCTAAGTA  TTTCAGGTTT  CAATAAAGCA
3951  GAGATTACAG  CCAAAGATGG  TAGAGATTTA  ACTATTGGCA  ACAGTAATGA
4001  CGGTAACAGC  GGTGCCGAAG  CCAAAACAGT  AACTTTTAAC  AATGTTAAAG
```

FIG. 7F.

```
4051  ATTCAAAAAT CTCTGCTGAC GGTCACAATG TGACACTAAA TAGCAAAGTG
4101  AAAACATCTA GCAGCAATGG CGGACGTGAA AGCAATAGCG ACAACGATAC
4151  CGGCTTAACT ATTACTGCAA AAAATGTAGA AGTAAACAAA GATATTACTT
4201  CTCTCAAAAC AGTAAATATC ACCGCGTCGG AAAAGGTTAC CACCACAGCA
4251  GGCTCGACCA TTAACGCAAC AAATGGCAAA GCAAGTATTA CAACCAAAAC
4301  AGGTGATATC AGCGGTACGA TTTCCGGTAA CACGGTAAGT GTTAGCGCGA
4351  CTGGTGATTT AACCACTAAA TCCGGCTCAA AAATTGAAGC GAAATCGGGT
4401  GAGGCTAATG TAACAAGTGC AACAGGTACA ATTGGCGGTA CAATTCCGG
4451  TAATACGGTA AATGTTACGG CAAACGCTGG CGATTTAACA GTTGGGAATG
4501  GCGCAGAAAT TAATGCGACA GAAGGAGCTG CAACCTTAAC CGCAACAGGG
4551  AATACCTTGA CTACTGAAGC CGGTTCTAGC ATCACTTCAA CTAAGGGTCA
4601  GGTAGACCTC TTGGCTCAGA ATGGTAGCAT CGCAGGAAGC ATTAATGCTG
4651  CTAATGTGAC ATTAAATACT ACAGGCACCT TAACCACCGT GGCAGGCTCG
4701  GATATTAAAG CAACCAGCGG CACCTTGGTT ATTAACGCAA AAGATGCTAA
4751  GCTAAATGGT GATGCATCAG GTGATAGTAC AGAAGTGAAT GCAGTCAACG
4801  ACTGGGGATT TGGTAGTGTG ACTGCGGCAA CCTCAAGCAG TGTGAATATC
4851  ACTGGGGATT TAAACACAGT AAATGGGTTA AATATCATTT CGAAAGATGG
```

FIG. 7G.

```
4901  TAGAAACACT  GTGCGCTTAA  GAGGCAAGGA  AATTGAGGTG  AAATATATCC
4951  AGCCAGGTGT  AGCAAGTGTA  GAAGAAGTAA  TTGAAGCGAA  ACGCGTCCTT
5001  GAAAAAGTAA  AAGATTTATC  TGATGAAGAA  AGAGAAACAT  TAGCTAAACT
5051  TGGTGTAAGT  GCTGTACGTT  TTGTTGAGCC  AAATAATACA  ATTACAGTCA
5101  ATACACAAAA  TGAATTACA   ACCAGACCGT  CAAGTCAAGT  GATAATTTCT
5151  GAAGGTAAGG  CGTGTTTCTC  AAGTGGTAAT  GGCGCACGAG  TATGTACCAA
5201  TGTTGCTGAC  GATGGACAGC  CGTAGTCAGT  AATTGACAAG  GTAGATTTCA
5251  TCCTGCAATG  AAGTCATTTT  ATTTCGTAT   TATTTACTGT  GTGGGTTAAA
5301  GTTCAGTACG  GGCTTTACCC  ATCTTGTAAA  AAATTACGGA  GAATACAATA
5351  AAGTATTTTT  AACAGGTTAT  TATTATGAAA  AATATAAAAA  GCAGATTAAA
5401  ACTCAGTGCA  ATATCAGTAT  TGCTTGGCCT  GGCTTCTTCA  TCATTGTATG
5451  CAGAAGAAGC  GTTTTAGTA   AAAGGCTTTC  AGTTATCTGG  TGCACTTGAA
5501  ACTTTAAGTG  AAGACGCCCA  ACTGTCTGTA  GCAAAATCTT  TATCTAAATA
5551  CCAAGGCTCG  CAAACTTAAA  CAAACCTAAA  AACAGCACAG  CTTGAATTAC
5601  AGGCTGTGCT  AGATAAGATT  GAGCCAAATA  AATTGATGT   GATATTGCCG
5651  CAACAAACCA  TTACGGATGG  CAATATCATG  TTTGAGCTAG  TCTCGAAATC
```

FIG. 7H.

```
5701  AGCCGCAGAA  AGCCAAGTTT  TTTATAAGGC  GAGCCAGGGT  TATAGTGAAG
5751  AAAATATCGC  TCGTAGCCTG  CCATCTTTGA  AACAAGGAAA  AGTGTATGAA
5801  GATGGTCGTC  AGTGGTTCGA  TTTGCGTGAA  TTTAATATGG  CAAAAGAAAA
5851  CCCGCTTAAG  GTTACCCGTG  TACATTACGA  ACTAAACCCT  AAAAACAAAA
5901  CCTCTAATTT  GATAATTGCG  GGCTTCTCGC  CTTTTGGTAA  AACGCGTAGC
5951  TTTATTTCTT  ATGATAATTT  CGGCGCGAGA  GAGTTTAACT  ACCAACCGTGT
6001  AAGCTTGGGT  TTTGTTAATG  CCAATTTAAC  TGGTCATGAT  GATGTGTTAA
6151  TTATACCAGT  ATGAGTTATG  CTGATTCTAA  TGATATCGAC  GGCTTACCAA
6201  GTGCGATTAA  TCGTAAATTA  TCAAAAGGTC  AATCTATCTC  TGCGAATCTG
6251  AAATGGAGTT  ATTATCTCCC  AACATTTAAC  CTTGGGCATGG  AAGACCAATT
6301  TAAAATTAAT  TTAGGCTACA  ACTACCGCCA  TATTAATCAA  ACCTCCGCGT
6351  TAAATCGCTT  GGGTGAAACG  AAGAAAAAT  TTGCAGTATC  AGGCGTAAGT
6401  GCAGGCATTG  ATGGACATAT  CCAATTTACC  CCTAAAAACAA  TCTTTAATAT
6451  TGATTTAACT  CATCATTATT  ACGCGAGTAA  ATTACCAGGC  TCTTTTGGAA
6501  TGGAGCGCAT  TGGCGAAACA  TTTAATCGCA  GCTATCACAT  TAGCACAGCC
6551  AGTTAGGGT  TGAGTCAAGA  GTTTGCTCAA  GGTTGGCATT  TTAGCAGTCA
6601  ATTATCAGGT  CAATTTACTC  TACAAGATAT  TAGCAGTATA  GATTATTCT
```

FIG. 7I.

```
6651  CTGTAACAGG  TACTTATGGC  GTCAGAGGCT  TTAAATACGG  CGGTGCAAGT
6701  GGTGAGCGCG  GTCTTGTATG  GCGTAATGAA  TTAAGTATGC  CAAAATACAC
6751  CCGCTTCCAA  ATCAGCCCTT  ATGCGTTTTA  TGATGCAGGT  CAGTTCCGTT
6801  ATAATAGCGA  AAATGCTAAA  ACTTACGGGCG  AAGATATGCA  CACGGTATCC
6851  TCTGCGGGTT  TAGGCATTAA  AACCTCTCCT  ACACAAAACT  TAAGCCTAGA
6901  TGCTTTTGTT  GCTCGTCGCT  TTGCAAATGC  CAATAGTGAC  AATTTGAATG
6951  GCAACAAAAA  ACGCACAAGC  TCACCTACAA  CCTTCTGGGG  GAGATTAACA
7001  TTCAGTTTCT  AACCCTGAAA  TTTAATCAAC  TGGTAAGCGT  TCCGCCTACC
7051  AGTTTATAAC  TATATGCTTT  ACCCGCCAAT  TTACAGTCTA  TAGGCAACCC
7101  TGTTTTTACC  CTTATATATC  AAATAAACAA  GCTAAGCTGA  GCTAAGCAAA
7151  CCAAGCAAAC  TCAAGCAAGC  CAAGTAATAC  TAAAAAAACA  ATTTATATGA
7201  TAAACTAAAG  TATACTCCAT  GCCATGGCGA  TACAAGGGAT  TTAATAATAT
7251  GACAAAAGAA  AATTTGCAAA  ACGCTCCTCA  AGATGCGACC  GCTTTACTTG
7301  CGGAATTAAG  CAACAATCAA  ACTCCCCCTGC  GAATATTTAA  ACAACCACGC
7351  AAGCCCAGCC  TATTACGCTT  GGAACAACAT  ATCGCAAAAA  AAGATTATGA
7401  GTTTGCTTGT  CGTGAATTAA  TGGTGATTCT  GGAAAAAATG  GACGCTAATT
```

FIG. 7J.

```
7451  TTGGAGGCGT  TCACGATATT  GAATTTGACG  CACCCGCTCA  GCTGGCATAT
7501  CTACCCGAAA  AATTACTAAT  TTATTTGCC   ACTCGTCTCG  CTAATGCAAT
7551  TACAACACTC  TTTTCCGACC  CCGAATTGGC  AATTCTGAA   GAAGGGGCGT
7601  TAAAGATGAT  TAGCCTGCAA  CGCTGGTTGA  CGCTGATTTT  TGCCTCTTCC
7651  CCCTACGTTA  ACGCAGACCA  TATTCTCAAT  AAATATAATA  TCAACCCAGA
7701  TTCCGAAGGT  GGCTTTCATT  TAGCAACAGA  CAACTCTTCT  ATTGCTAAAT
7751  TCTGTATTTT  TTACTTACCC  GAATCAATG   TCAATATGAG  TTTAGATGCG
7801  TTATGGCAG   GGAATCAACA  ACTTTGTGCT  TCATTGTGTT  TTGCGTTGCA
7851  GTCTTCACGT  TTTATTGGTA  CCGCATCTGC  GTTTCATAAA  AGAGCGGTGG
7901  TTTTACAGTG  GTTCCTAAA   AAACTCGCCG  AAATTGCTAA  TTTAGATGAA
7951  TTGCCTGCAA  ATATCCTTCA  TGATGTATAT  ATGCACTGCA  GTTATGATTT
8001  AGCAAAAAAC  AAGCACGATG  TTAAGCGTCC  ATTAAACGAA  CTTGTCCGCA
8051  AGCATATCCT  CACGCAAGGA  TGGCAAGACC  GCTACCTTTA  CACCTTAGGT
8101  AAAAGGACG   GCAAACCTGT  GATGATGGTA  CTGCTTGAAC  ATTTTAATTC
8151  GGGACATTCG  ATTTATCGTA  CACATTCAAC  TTCAATGATT  GCTGCTCGAG
8201  AAAAATTCTA  TTTAGTCGGC  TTAGGCCATG  AGGGCGTTGA  TAAAATAGGT
```

FIG. 7K.

```
8251  CGAGAAGTGT TTGACGAGTT CTTTGAAATC AGTAGCAATA ATATAATGGA
8301  GAGACTGTTT TTTATCCGTA AACAGTGCGA AACTTTCCAA CCCGCAGTGT
8351  TCTATATGCC AAGCATTGGC ATGGATATTA CCACGATTTT TGTGAGCAAC
8401  ACTCGGCTTG CCCCTATTCA AGCTGTAGCC CTGGGTCATC CTGCCACTAC
8451  GCATTCTGAA TTTATTGATT ATGTCATCGT AGAAGATGAT TATGTGGGCA
8501  GTGAAGATTG TTTCAGCGAA ACCCTTTTAC GCTTACCCAA AGATGCCCTA
8551  CCTTATGTAC CTTCTGCACT CGCCCCACAA AAAGTGGATT ATGTACTCAG
8601  GGAAAACCCT GAAGTAGTCA ATATCGGTAT TGCCGCTACC ACAATGAAAT
8651  TAAACCCTGA ATTTTTGCTA ACATTGCAAG AAATCAGAGA TAAAGCTAAA
8701  GTCAAAATAC ATTTTCATTT CGCACTTGGA CAATCAACAG GCTTGACACA
8751  CCCTTATGTC AAATGGTTTA TCGAAAGCTA CACGATTATC GATGCCACTG
8801  CACATCCCCA CGCACCTTAT TCCTTTCGGT TGGCAATATT GCGTGATTGC
8851  GATATGCTAC TAAATCCGTT TTAGGTGTAT AATACTAACG GCATAATTGA
8901  TATGGTTACA TTAGGTTTAG TTGGTGTATG CAAAACGGGG GATGAAGTAC
8951  ATGAACATAT TGATGAAGGT CTGTTTAAAC GCTTAGGACT ACCAGAATGG
9001  CTGATAGCCG ACACACGAGA AACATATATT GAATGTGCTT TGCGTCTAGC
9051  AGAAAACCAT CAAGAACGCC TTGAACTCCG TCGTTACATC ATAGAAAACA
```

FIG. 7L.

```
9101  ACGGCTTACA  AAAGCTTTTT  ACAGGGCGACC  CTCGTCCATT  GGGCAAAATA
9151  CTGCTTAAGA  AAACAAATGA  ATGGAAGCGG  AAGCACTTGA  GTAAAAAATA
9201  ACGGTTTTTT  AAAGTAAAAG  TGCGGTTAAT  TTTCAAAGCG  TTTTAAAAAC
9251  CTCTCAAAAA  TCAACCGCAC  TTTTATCTTT  ATAACGATCC  CGCACGCTGA
9301  CAGTTTATCA  GCCTCCCGCC  ATAAAACTCC  GCCTTTCATG  GCGGAGATTT
9351  TAGCCAAAAC  TGGCAGAAAT  TAAAGGCTAA  AATCACCAAA  TTGCACCACA
9401  AAATCACCAA  TACCCACAAA  AAA
```

FIG. 8A.

```
  1 GATCAATCTG GGCGATATTT TTGCCAAAGG TGGTAACATT AATGTCCGCG
 51 CTGCCACTAT TCGCAATAAA GGTAAACTTT CTGCCGACTC TGTAAGCAAA
101 GATAAAAGTG GTAACATTGT TCTCTCTGCC AAAGAAGGTG AAGCGGAAAT
151 TGGCGGTGTA ATTCCGCTC AAAATCAGCA AGCCAAAGGT GGTAAGTTGA
201 TGATTACAGG CGATAAAGTT ACATTGAAAA CGGGTGCAGT TATCGACCTT
251 TCGGGTAAAG AAGGGGGAGA AACTTATCTT GGCGGTGACG AGCGTGGCGA
301 AGGTAAAAAC GGCATTCAAT TAGCAAAGAA AACCACTTTA GAAAAAGGCT
351 CAACAATTAA TGTGTCAGGT AAAGAAAAAG GTGGGCGCGC TATTGTATGG
401 GGCGATATTG CGTTAATTGA CGGCAATATT AATGCCCAAG GTAAAGATAT
451 CGCTAAAACT GGTGGTTTTG TGGAGACGTC GGGGCATTAC TTATCCATTG
501 ATGATAACGC AATTGTTAAA ACAAAAGAAT GGCTACTAGA CCCAGAGAAT
551 GTGACTATTG AAGCTCCTTC CGCTTCTCGC GTCGAGCTGG GTGCCGATAG
601 GAATTCCCAC TCGGCAGAGG TGATAAAAGT GACCCTAAAA AAAAATAACA
651 CCTCCTTGAC AACACTAACC AATACAACCA TTTCAAATCT TCTGAAAAGT
701 GCCCACGTGG TGAACATAAC GGCAAGGAGA AAACTTACCG TTAATAGCTC
751 TATCAGTATA GAAAGAGGCT CCCACTTAAT TCTCCACAGT GAAGGTCAGG
```

FIG. 8B.

```
 801  GCGGTCAAGG TGTTCAGATT GATAAAGATA TTACTTCTGA AGGCGGAAAT
 851  TTAACCATTT ATTCTGGCGG ATGGGTTGAT GTTCATAAAA ATATTACGCT
 901  TGGTAGCGGC TTTTTAAACA TCACAACTAA AGAAGGAGAT ATCGCCTTCG
 951  AAGACAAGTC TGGACGGAAC AACCTAACCA TTACAGCCCA AGGGACCATC
1001  ACCTCAGGTA ATAGTAACGG CTTTAGATTT AACAACGTCT CTCTAAACAG
1051  CCTTGGCGGA AAGCTGAGCT TTACTGACAG CAGAGAGGAC AGAGGTAGAA
1101  GAACTAAGGG TAATATCTCA AACAAATTTG ACGGAACGTT AAACATTTCC
1151  GGAACTGTAG ATATCTCAAT GAAAGCACCC AAAGTCAGCT GGTTTTACAG
1201  AGACAAAGGA CGCACCTACT GGAACGTAAC CACTTTAAAT GTTACCTCGG
1251  GTAGTAAATT TAACCTCTCC ATTGACAGCA CAGGAAGTGG CTCAACAGGT
1301  CCAAGCATAC GCAATGCAGA ATTAAATGGC ATAACATTTA ATAAAGCCAC
1351  TTTTAATATC GCACAAGGCT CAACAGCTAA CTTTAGCATC AAGGCATCAA
1401  TAATGCCCTT TAAGAGTAAC GCTAACTACG CATTATTTAA TGAAGATATT
1451  TCAGTCTCAG GGGGGGTAG CGTTAATTTC AAACTTAACG CCTCATCTAG
1501  CAACATACAA ACCCCTGGCG TAATTATAAA ATCTCAAAAC TTTAATGTCT
1551  CAGGAGGGTC AACTTTAAAT CTCAAGGCTG AAGGTTCAAC AGAAACCGCT
1601  TTTTCAATAG AAAATGATTT AAACTTAAAC GCCACCGGTG GCAATATAAC
```

FIG. 8C.

```
1651  AATCAGACAA  GTCGAGGGTA  CCGATTCACG  CGTCAACAAA  GGTGTCGCAG
1701  CCAAAAAAAA  CATAACTTTT  AAAGGGGGTA  ATATCACCTT  CGGCTCTCAA
1751  AAAGCCACAA  CAGAAATCAA  AGGCAATGTT  ACCATCAATA  AAAACACTAA
1801  CGCTACTCTT  CGTGGTGCGA  ATTTTGCCGA  AAACAAATCG  CCTTTAAATA
1851  TAGCAGGAAA  TGTTATTAAT  AATGGCAACC  TTACCACTGC  CGGCTCCATT
1901  ATCAATATAG  CCGGAAATCT  TACTGTTTCA  AAAGGCGCTA  ACCTTCAAGC
1951  TATAACAAAT  TACACTTTTA  ATGTAGCCGG  CTCATTTGAC  AACAATGGCG
2001  CTTCAAACAT  TTCCATTGCC  AGAGGAGGGG  CTAAATTTAA  AGATATCAAT
2051  AACACCAGTA  GCTTAAATAT  TACCACCAAC  TCTGATACCA  CTTACCGCAC
2101  CATTATAAAA  GGCAATATAT  CCAACAAATC  AGGTGATTTG  AATATTATTG
2151  ATAAAAAAAG  CGACGCTGAA  ATCCAAATTG  GCGGCAATAT  CTCACAAAAA
2201  GAAGGCAATC  TCACAATTTC  TTCTGATAAA  GTAAATATTA  CCAATCAGAT
2251  AACAATCAAA  GCAGGCGTTG  AAGGGGGGCG  TTCTGATTCA  AGTGAGGCAG
2301  AAAATGCTAA  CCTAACTATT  CAAACCAAAG  AGTTAAAATT  GGCAGGAGAC
2351  CTAAATATTT  CAGGCTTTAA  TAAAGCAGAA  ATTACAGCTA  AAATGGCAG
2401  TGATTTAACT  ATTGGCAATG  CTAGCGGTGG  TAATGCTGAT  GCTAAAAAAG
```

FIG. 8D.

```
2451  TGACTTTTGA CAAGGTTAAA GATTCAAAAA TCTCGACTGA CGGTCACAAT
2501  GTAACACTAA ATAGCGAAGT GAAAACGTCT AATGGTAGTA GCAATGCTGG
2551  TAATGATAAC AGCACCGGTT TAACCATTTC CGCAAAAGAT GTAACGGTAA
2601  ACAATAACGT TACCTCCCAC AAGACAATAA ATATCTCTGC CGCAGCAGGA
2651  AATGTAACAA CCAAAGAAGG CACAACTATC AATGCAACCA CAGGCAGCGT
2701  GGAAGTAACT GCTCAAAATG GTACAATTAA AGGCAACATT ACCTCGCAAA
2751  ATGTAACAGT GACAGCAACA GAAAATCTTG TTACCACAGA GAATGCTGTC
2801  ATTAATGCAA CCAGCGGCAC AGTAAACATT AGTACAAAAA CAGGGGATAT
2851  TAAAGGTGGA ATTGAATCAA CTTCCGGTAA TGTAAATATT ACAGCGAGCG
2901  GCAATACACT TAAGGTAAGT AATATCACTG GTCAAGATGT AACAGTAACA
2951  GCGGATGCAG GAGCCTTGAC AACTACAGCA GGCTCAACCA TTAGTGCGAC
3001  AACAGGCAAT GCAAATATTA CAACCAAAAC AGGTGATATC AACGGTAAAG
3051  TTGAATCCAG CTCCGGCTCT GTAACACTTG TTGCAACTGG AGCAACTCTT
3101  GCTGTAGGTA ATATTTCAGG TAACACTGTT ACTATTACTG CGGATAGCGG
3151  TAAATTAACC TCCACAGTAG GTTCTACAAT TAATGGGACT AATAGTGTAA
3201  CCACCTCAAG CCAATCAGGC GATATTGAAG GTACAATTTC TGGTAATACA
3251  GTAAATGTTA CAGCAAGCAC TGGTGATTTA ACTATTGGAA ATAGTGCAAA
```

FIG. 8E.

```
3301  AGTTGAAGCG  AAAAATGGAG  CTGCAACCTT  AACTGCTGAA  TCAGGCAAAT
3351  TAACCACCCA  AACAGGCTCT  AGCATTACCT  CAAGCAATGG  TCAGACAACT
3401  CTTACAGCCA  AGGATAGCAG  TATCGCAGGA  AACATTAATG  CTGCTAATGT
3451  GACGTTAAAT  ACCACAGGCA  CTTTAACTAC  TACAGGGGAT  TCAAAGATTA
3501  ACGCAACCAG  TGGTACCTTA  ACAATCAATG  CAAAAGATGC  CAAATTAGAT
3551  GGTGCTGCAT  CAGGTGACCG  CACAGTAGTA  AATGCAACTA  ACGCAAGTGG
3601  CTCTGGTAAC  GTGACTGCGA  AAACCTCAAG  CAGCGTGAAT  ATCACCGGGG
3651  ATTTAAACAC  AATAAATGGG  TTAAATATCA  TTTCGGAAAA  TGGTAGAAAC
3701  ACTGTGCGCT  TAAGAGGCAA  GGAAATTGAT  GTGAAATATA  TCCAACCAGG
3751  TGTAGCAAGC  GTAGAAGAGG  TAATTGAAGC  GAAACGCGTC  CTTGAGAAGG
3801  TAAAAGATTT  ATCTGATGAA  GAAAGAGAAA  CACTAGCCAA  ACTTGGTGTA
3851  AGTGCTGTAC  GTTTCGTTGA  GCCAAATAAT  GCCATTACGG  TTAATACACA
3901  AAACGAGTTT  ACAACCAAAC  CATCAAGTCA  AGTGACAATT  TCTGAAGGTA
3951  AGGCGTGTTT  CTCAAGTGGT  AATGGCGCAC  GAGTATGTAC  CAATGTTGCT
4001  GACGATGGAC  AGCAGTAGTC  AGTAATTGAC  AAGGTAGATT  TCATCCTGCA
4051  ATGAAGTCAT  TTTATTTTCG  TATTATTTAC  TGTGTGGGTT  AAAGTTCAGT
```

FIG. 8F.

```
4101  ACGGGCTTTA CCCACCTTGT AAAAAATTAC GAAAAATACA ATAAAGTATT
4151  TTTAACAGGT TATTATTATG AAAACATAA  AAAGCAGATT AAAACTCAGT
4201  GCAATATCAA TATTGCTTGG CTTGGCTTCT TCATCGACGT ATGCAGAAGA
4251  AGCGTTTTTA GTAAAAGGCT TTCAGTTATC TGGCGCG
```

FIG. 9A.

```
  1  GGGAATGAGC GTCGTACACG GTACAGCAAC CATGCAAGTA GACGGCAATA
 51  AAACCACTAT CCGTAATAGC GTCAATGCTA TCATCAATTG GAAACAATTT
101  AACATTGACC AAAATGAAAT GGAGCAGTTT TTACAAGAAA GCAGCAACTC
151  TGCCGTTTTC AACCGTGTTA CATCTGACCA AATCTCCCAA TTAAAGGGA
201  TTTTAGATTC TAACGGACAA GTCTTTTTAA TCAACCCAAA TGGTATCACA
251  ATAGGTAAAG ACGCAATTAT TAACACTAAT GGCTTTACTG CTTCTACGCT
301  AGACATTTCT AACGAAAACA TCAAGGCGCG TAATTTCACC CTTGAGCAAA
351  CCAAGGATAA AGCACTCGCT GAAATCGTGA ATCACGGTTT AATTACCGTT
401  GGTAAAGACG GTAGCGTAAA CCTTATTGGT GGCAAAGTGA AAAACGAGGG
451  CGTGATTAGC GTAAATGGCG GTAGTATTTC TTTACTTGCA GGGCAAAAAA
501  TCACCATCAG CGATATAATA AATCCAACCA TCACTTACAG CATTGCTGCA
551  CCTGAAAACG AAGCGATCAA TCTGGGCGAT ATTTTTGCCA AAGGTGGTAA
601  CATTAATGTC CGCGCTGCCA CTATTCGCAA TAAAGGTAAA CTTTCTGCCG
651  ACTCTGTAAG CAAAGATAAA AGTGGTAACA TTGTTCTCTC TGCCAAAGAA
701  GGTGAAGCGG AAATTGGCGG TGTAATTTCC GCTCAAAATC AGCAAGCCAA
751  AGGTGGTAAG TTGATGATTA CAGGTGATAA AGTCACATTA AAAACAGGTG
```

FIG. 9B.

```
 801  CAGTTATCGA CCTTTCAGGT AAAGAAGGGG GAGAGACTTA TCTTGGCGGT
 851  GATGAGCGTG GCGAAGGTAA AAATGGTATT CAATTAGCGA AGAAACCTC
 901  TTTAGAAAAA GGCTCGACAA TTAATGTATC AGGCAAAGAA AAAGGCGGGC
 951  GCGCTATTGT ATGGGGCGAT ATTGCATTAA TTAATGGTAA CATTAATGCT
1001  CAAGGTAGCG ATATTGCTAA AACTGGCGGC TTTGTGGAAA CATCAGGACA
1051  TGACTTATCC ATTGGTGATG ATGTGATTGT TGACGCTAAA GAGTGGTTAT
1101  TAGACCCAGA TGATGTGTCC ATTGAAACTC TTACATCTGG ACGCAATAAT
1151  ACCGGCGAAA ACCAAGGATA TACAACAGGA AACAAACTCA AAGAGTCACC
1201  TAAAGGTAAT AGTATTCTA TATGTTAATA TCACTGCTAA ACTCTTGAGC
1251  AAATCCTAAG AAGAGGTTCT CTTATCTAAT GGCAGTTTAA TAATAGAATT
1301  TATGTTAATA GCTCCATCAA TTAACGGTGA TATTACCTCA CACTTCACAC
1351  TAAACGAGAT GGAGTTAAAA GGCTCTTGGG TTTGATGTTCA AACGAAAATG
1401  GTAATTTAAC CATTAAAGCA CGGGTTTTTT GAATATTGTC GCTGGGGATT TAAAAACATC
1451  ACGCTTGGTA CGGGTTTTTT GAATATTGTC GCTGGGGATT CTGTAGCTTT
1501  TGAGAGAGAG GGCGATAAAG CACGTAAACG AACAGATGCT CAAATTACCG
1551  CACAAGGGAC GATAACCGTC AATAAAGATG ATAAACAATT TAGATTCAAT
1601  AATGTATCTA TTAACGGGAC GGGCAAGGGT TTAAAGTTTA TTGCAAATCA
```

FIG. 9C.

```
1651  AAATAATTTC  ACTCATAAAT  TTGATGGCGA  AATTAACATA  TCTGGAATAG
1701  TAACAATTAA  CCAAACCACG  AAAAAAGATG  TTAAATACTG  GAATGCATCA
1751  AAAGACTCTT  ACTGGAATGT  TTCTTCTCTT  ACTTTGAATA  CGGTGCAAAA
1801  ATTTACCTTT  ATAAAATTCG  TTGATAGCGG  CTCAAATTCC  CAAGATTTGA
1851  GGTCATCACG  TAGAAGTTTT  GCAGGCGTAC  ATTTTAACGG  CATCGGAGGC
1901  AAAACAAACT  TCAACATCGG  AGCTAACGCA  AAAGCCTTAT  TTAAATTAAA
1951  ACCAAACGCC  GCTACAGACC  CAAAAAAAGA  ATTACCTATT  ACTTTTAACG
2001  CCAACATTAC  AGCTACCGGT  AACAGTGATA  GCTCTGTGAT  GTTTGACATA
2051  CACGCCAATC  TTACCTCTAG  AGCTGCCGGC  ATAAACATGG  ATTCAATTAA
2101  CATTACCGGC  GGGCTTGACT  TTTCCATAAC  ATCCCATAAT  CGCAATAGTA
2151  ATGCTTTTGA  AATCAAAAAA  GACTTAACTA  TAAATGCAAC  TGGCTCGAAT
2201  TTTAGTCTTA  AGCAAACGAA  AGATTCTTTT  TATAATGAAT  ACAGCAAACA
2251  CGCCATTAAC  TCAAGTCATA  ATCTAACCAT  TCTTGGCGGC  AATGTCACTC
2301  TAGGTGGGGA  AAATTCAAGC  AGTAGCATTA  TCTTGGCGGC  CAATATCACC
2351  AATAAAGCAA  ATGTTACATT  ACAAGCTGAC  ACCAGCAACA  GCAACACAGG
2401  CTTGAAGAAA  AGAACTCTAA  CTCTTGGCAA  TATATCTGTT  GAGGGAATT
```

FIG. 9D.

```
2451  TAAGCCTAAC TGGTGCAAAT GCAAACATTG TCGGCAATCT TTCTATTGCA
2501  GAAGATTCCA CATTTAAAGG AGAAGCCAGT GACAACCTAA ACATCACCGG
2551  CACCTTTACC AACAACGGTA CCGCCAACAT TAATATAAAA CAAGGAGTGG
2601  TAAAACTCCA AGGCGATATT ATCAATAAAG GTGGTTTAAA TATCACTACT
2651  AACGCCTCAG GCACTCAAAA AACCATTATT AACGGAAATA TAACTAACGA
2701  AAAAGGCGAC TTAAACATCA AGAATATTAA AGCCCGACGC GAAATCCAAA
2751  TTGGCGGCAA TATCTCACAA AAAGAAGGCA ATCTCACAAT TTCTTCTGAT
2801  AAAGTAAATA TTACCAATCA GATAACAATC AAAGCAGGCG TTGAAGGGGG
2851  GCGTTCTGAT TCAAGTGAGG CAGAAAATGC TAACCTAACT ATTCAAACCA
2901  AAGAGTTAAA ATTGGCAGGA GACCTAAATA TTTCAGGCTT TAATAAAGCA
2951  GAAATTACAG CTAAAAATGG CAGTGATTTA ACTATTGGCA ATGCTAGCGG
3001  TGGTAATGCT GATGCTAAAA AAGTGACTTT TGACAAGGTT AAAGATTCAA
3051  AAATCTCGAC TGACGGTCAC AATGTAACAC TAAATAGCGA AGTGAAAACG
3101  TCTAATGGTA GTAGCAATGC TGGTAATGAT AACAGCACCG GTTTAACCAT
3151  TTCCGCAAAA GATGTAACGG TAAACAATAA CGTTACCTCC CACAAGACAA
3201  TAAATATCTC TGCCGCAGCA GGAAATGTAA CAACCAAAGA AGGCACAACT
3251  ATCAATGCAA CCACAGGCAG CGTGGAAGTA ACTGCTCAAA ATGGTACAAT
```

FIG. 9E.

```
3301 TAAAGGCAAC ATTACCTCGC AAAATGTAAC AGTGACAGCA ACAGAAAATC
3351 TTGTTACCAC AGAGAATGCT GTCATTAATG CAACCAGCGG CACAGTAAAC
3401 ATTAGTACAA AAACAGGGGA TATTAAAGGT GGAATTGAAT CAACTTCCGG
3451 TAATGTAAAT ATTACAGCGA GCGGCAATAC ACTTAAGGTA AGTAATATCA
3501 CTGGTCAAGA TGTAACAGTA ACAGCGGATG CAGGAGCCTT GACAACTACA
3551 GCAGGCTCAA CCATTAGTGC GACAACAGGC AATGCAAATA TTACAACCAA
3601 AACAGGTGAT ATCAACGGTA AAGTTGAATC CAGCTCCGGC TCTGTAACAC
3651 TTGTTGCAAC TGGAGCAACT CTTGCTGTAG GTAATATTTC AGGTAACACT
3701 GTTACTATTA CTGCGGATAG CGGTAAATTA ACCTCCACAG TAGGTTCTAC
3751 AATTAATGGG ACTAATAGTG TAACCACCTC AAGCCAATCA GGCGATATTG
3801 AAGGTACAAT TTCTGGTAAT ACAGTAAATG TTACAGCAAG CACTGGTGAT
3851 TTAACTATTG GAAATAGTGC AAAAGTTGAA GCGAAAAATG GAGCTGCAAC
3901 CTTAACTGCT GAATCAGGCA AATTAACCAC CCAAACAGGC TCTAGCATTA
3951 CCTCAAGCAA TGGTCAGACA ACTCTTACAG CCAAGGATAG CAGTATCGCA
4001 GGAAACATTA ATGCTGCTAA TGTGACGTTA AATACCACAG GCACTTTAAC
4051 TACTACAGGG GATTCAAAGA TTAACGCAAC CAGTGGTACC TTAACAATCA
```

FIG. 9F.

```
4101 ATGCAAAAGA TGCCAAATTA GATGGTGCTG CATCAGGTGA CCGCACAGTA
4151 GTAAATGCAA CTAACGCAAG TGGCTCTGGT AACGTGACTG CGAAACCTC
4201 AAGCAGCGTG AATATCACCG GGGATTAAA CACAATAAAT GGGTTAAATA
4251 TCATTTCGGA AAATGGTAGA AACACTGTGC GCTTAAGAGG CAAGGAAATT
4301 GATGTGAAAT ATATCCAACC AGGTGTAGCA AGCGTAGAAG AGGTAATTGA
4351 AGCGAAACGC GTCCTTGAGA AGGTAAAAGA TTTATCTGAT GAAGAAAGAG
4401 AAACACTAGC CAAACTTGGT GTAAGTGCTG TACGTTTCGT TGAGCCAAAT
4451 AATGCCATTA CGGTTAATAC ACAAAACGAG TTTACAACCA AACCATCAAG
4501 TCAAGTGACA ATTTCTGAAG GTAAGGCGTG TTTCTCAAGT GGTAATGGCG
4551 CACGAGTATG TACCAATGTT GCTGACGATG GACAGCAGTA GTCAGTAATT
4601 GACAAGGTAG ATTTCATCCT GCAATGAAGT CATTTTATTT TCGTATTATT
4651 TACTGTGTGG GTTAAAGTTC AGTACGGGCT TTACCCACCT TGTAAAAAAT
4701 TA
```

FIG. 10A. COMPARISON OF DERIVED AMINO ACID SEQUENCE

```
              1                                                          50
Hmw3com       ..........  ..........  ..........  ..........  ..........
Hmw4com       ..........  ..........  ..........  ..........  ..........
Hmw1com       MNKIYRLKFS  KRLNALVAVS  ELARGCDHST  EKGSEKPARM  KVRHLALKPL
Hmw2com       MNKIYRLKFS  KRLNALVAVS  ELARGCDHST  EKGSEKPARM  KVRHLALKPL 51                                                        100
Hmw3com       ..........  ..........  ..........  ..........  ..........
Hmw4com       ..........  ..........  ..GMSVVHGT  ATMQVDGNKT  TIRNSVNAII
Hmw1com       SAMLLSLGVT  SIPQSVLASG  LQGMSVVHGT  ATMQVDGNKT  TIRNSVNAII
Hmw2com       SAMLLSLGVT  SIPQSVLASG  LQGMSVVHGT  ATMQVDGNKT  TIRNSVNAII 101                                                       150
Hmw3com       ..........  ..........  ..........  ..........  ..........
Hmw4com       NWKQFNIDQN  EMEQFLQESS  NSAVFNRVTS  DQISQLKGIL  DSNGQVFLIN
```

FIG. 10B.

```
Hmw1com  NWKQFNIDQN EMVQFLQENN NSAVFNRVTS NQISQLKGIL DSNGQVFLIN
Hmw2com  NWKQFNIDQN EMVQFLQENN NSAVFNRVTS NQISQLKGIL DSNGQVFLIN
              151                                              200
Hmw3com  .......... .......... .......... .......... ..........
Hmw4com  PNGITIGKDA IINTNGFTAS TLDISNENIK ARNFTLEQTK DKALAEIVNH
Hmw1com  PNGITIGKDA IINTNGFTAS TLDISNENIK ARNFTLEQTK DKALAEIVNH
Hmw2com  PNGITIGKDA IINTNGFTAS TLDISNENIK ARNFTLEQTK DKALAEIVNH
              201                                              250
Hmw3com  .......... .......... .......... .......... ..........
Hmw4com  GLITVGKDGS VNLIGGKVKN EGVISVNGGS ISLLAGQKIT ISDIINPTIT
Hmw1com  GLITVGKDGS VNLIGGKVKN EGVISVNGGS ISLLAGQKIT ISDIINPTIT
Hmw2com  GLITVGKDGS VNLIGGKVKN EGVISVNGGS ISLLAGQKIT ISDIINPTIT
              251                                              300
Hmw3com  .......... INLGDIFAKG GNINVRAATI RNKGKLSADS VSKDKSGNIV
```

FIG. 10C.

| | | | | | | |
|---|---|---|---|---|---|---|
| Hmw4com | YSIAAPENEA | INLGDIFAKG | GNINVRAATI | RNKGKLSADS | VSKDKSGNIV | |
| Hmw1com | YSIAAPENEA | VNLGDIFAKG | GNINVRAATI | RNKGKLSADS | VSKDKSGNIV | |
| Hmw2com | YSIAAPENEA | VNLGDIFAKG | GNINVRAATI | RNKGKLSADS | VSKDKSGNIV | |

301                                                                                       350

| | | | | | | |
|---|---|---|---|---|---|---|
| Hmw3com | LSAKEGEAEI | GGVISAQNQQ | AKGGKLMITG | DKVTLKTGAV | IDLSGKEGGE | |
| Hmw4com | LSAKEGEAEI | GGVISAQNQQ | AKGGKLMITG | DKVTLKTGAV | IDLSGKEGGE | |
| Hmw1com | LSAKEGEAEI | GGVISAQNQQ | AKGGKLMITG | DKVTLKTGAV | IDLSGKEGGE | |
| Hmw2com | LSAKEGEAEI | GGVISAQNQQ | AKGGKLMITG | DKVTLKTGAV | IDLSGKEGGE | |

351                                                                                       400

| | | | | | | |
|---|---|---|---|---|---|---|
| Hmw3com | TYLGGDERGE | GKNGIQLAKK | TTLEKGSTIN | VSGKEKGGRA | IVWGDIALID | |
| Hmw4com | TYLGGDERGE | GKNGIQLAKK | TTLEKGSTIN | VSGKEKGGRA | IVWGDIALID | |
| Hmw1com | TYLGGDERGE | GKNGIQLAKK | TTLEKGSTIN | VSGKEKGGRA | IVWGDIALID | |
| Hmw2com | TYLGGDERGE | GKNGIQLAKK | TTLEKGSTIN | VSGKEKGGRA | IVWGDIALID | |

FIG. 10D.

```
        401                                                                    450
Hmw3com GNINAQGK.D IAKTGGFVET SGHYLSIDDN AIVKTKEWLL DPENVTIEAP
Hmw4com GNINAQGS.D IAKTGGFVET SGHDLSIGDD VIVDAKEWLL DPDDVSIETL
Hmw1com GNINAQGSGD IAKTGGFVET SGHDLFIKDN AIVDAKEWLL DPDNVTINAE
Hmw2com GNINAQGSGD IAKTGGFVET SGHYLSIESN AIVKTKEWLL DPDDVTIEAE 451                                                                    500
Hmw3com SASRVELGAD RNSHSAEVIK VTLKKNNTSL TTLTNTTISN LLKSAHVVNI
Hmw4com TSGRNNTGEN QGYTTGDGTK ESPKGNSISK PTLTNSTLEQ ILRRGSYVNI
Hmw1com TAGRSNTSED DEYTGSGNSA STPKRNKE.K TTLTNTTLES ILKKGTFVNI
Hmw2com DPLRNNTGIN DEFPTGTGEA SDPKKNSELK TTLTNTTISN YLKNAWTMNI 501                                                                    550
Hmw3com TARRKLTVNS SISIERGSHL ILHSEGQGGQ GVQIDKDITS .E...GGNLT
Hmw4com TANNRIYVNS SINLSNGS.L TLHTK...RD GVKINGDITS NE...NGNLT
Hmw1com TANQRIYVNS SINL.SNGSL TLWSEGRSGG GVEINNDITT GDDTRGANLT
Hmw2com TASRKLTVNS SINGSNGSHL ILHSKGQRGG GVQIDGDIT. ...SKGGNLT
```

FIG. 10E.

```
       551                                                        600
Hmw3com  IYSGGWVDVH  KNITLGS.GF  LNITTKEGDI  AFEDKSGR..  ..NNLTITAQ
Hmw4com  IKAGSWVDVH  KNITLGT.GF  LNIVAGDS.V  AFEREGDKAR  NATDAQITAQ
Hmw1com  IYSGGWVDVH  KNISLGAQGN  INITAKQD.I  AFEKGSNQV.  ......ITGQ
Hmw2com  IYSGGWVDVH  KNITLD.QGF  LNITA.AS.V  AFEGGNNKAR  DANNLTITAQ 601                                                        650
Hmw3com  GTITSG.NSN  GFRFNNVSLN  SLGGKLSFTD  SREDRGRRTK  GNISNKFDGT
Hmw4com  GTITVNKDDK  QFRFNNVSIN  GTGKGLKFIA  NQN.......  .NFTHKFDGE
Hmw1com  GTIT.SGNQK  GFRFNNVSLN  GTGSGLQFTT  KRTN......K  YAITNKFEGT
Hmw2com  GTVTITGEGK  DFRANNVSLN  GTGKGLNIIS  SVNN......  ..LTHNLSGT 651                                                        700
Hmw3com  LNISGTVDIS  MKAPKVSWFY  RD.KGRTYWN  VTTLNVTSGS  KFNLSIDSTG
Hmw4com  INISGIVTIN  QTTKKDVKYW  NA.SKDSYWN  VSSLTLNTVQ  KFTF.IKFVD
Hmw1com  LNISGKVNIS  MVLPKNESGY  DKFKGRTYWN  LTSLNVSESG  EFNLTIDSRG
```

FIG. 10F.

```
Hmw2com  INISGNITIN QTTRKNTSYW QTSHD.SHWN VSALNLETGA NFTF.IKYIS 701                                              750
Hmw3com  SGSTG...PS IRNA..ELNG ITFN....KA TFNIAQGSTA NFSIKASIMP
Hmw4com  SGSNS...QD LRSSRRSFAG VHFNGIGGKT NFNIGANAKA LFKLKPNAAT
Hmw1com  SDSAGTLTQ. ....PYNLNG ISFN...KDT TFNVERNARV NFDIKAPIGI
Hmw2com  SNSKGLTTQY RSSAGVNFNG V..N...GNM SFNLKEGAKV NFKLKPNENM 751                                              800
Hmw3com  FKSNANYAL. FNEDISVSG. .GGSVNFKLN ASSSNIQTPG VIIKSQNFNV
Hmw4com  DPKKELPIT. FNANITATGN SDSSVMFDIH A...NLTSRA AGINMDSINI
Hmw1com  NKYSSLNYAS FNGNISVSG. .GGSVDFTLL ASSSNVQTPG VVINSKYFNV
Hmw2com  NTSKPLPI.R FLANITATG. .GGSVFFDIY ANHS...GRG AELKMSEINI 801                                              850
Hmw3com  SGGSTLNLKA EGSTETAFSI ENDLNLNATG GNITIRQVEG T..DSRVNKG
Hmw4com  TGGLDFSITS HNRNSNAFEI KKDLTINATG SNFSLKQTKD SFYNEYSKHA
```

FIG. 10G.

```
Hmw1com  STGSSLRFKT  SGSTKTGFSI  EKDLTLNATG  GNITLLQVEG  T..DGMIGKG
Hmw2com  SNGANFTLNS  HVRGDDAFKI  NKDLTINATN  SNFSLRQTKD  DFYDGYARNA
                                                                  900

Hmw3com  VAAKKNITFK  GGNITFGSQK  ATTEIKGNVT  INKNTNATLR  GANFAEN...
Hmw4com  INSSHNLTIL  GGNVTLGGEN  SSSSITGNIN  ITNKANVTLQ  ADTSNSNTGL
Hmw1com  IVAKKNITFE  GGNITFGSRK  AVTEIEGNVT  INNNANVTLI  GSDFDNHQ..
Hmw2com  INSTYNISIL  GGNVTLGGQN  SSSSITGNIT  IEKAANVTLE  ANNAPNQQNI
                                                                  950

Hmw3com  KSPLNIAGNV  INNGNLTTAG  SIINIAGNLT  VSKGANLQAI  TNYTFNVAGS
Hmw4com  KKRTLTLGNI  SVEGNLSLTG  ANANIVGNLS  IAEDSTFKGE  ASDNLNITGT
Hmw1com  KPLTIKKDVI  INSGNLTAGG  NIVNIAGNLT  VESNANFKAI  TNFTFNVGGL
Hmw2com  RDRVIKLGSL  LVNGSLSLTG  ENADIKGNLT  ISESATFKGK  TRDTLNITGN
                                                                 1000
```

FIG. 10H.

```
              1001                                                           1050
Hmw3com  FDNNGASNIS  IARGGAKFK.  DINNTSSLNI  TTNSDTTYRT  IIKGNISNKS
Hmw4com  FTNNGTANIN  IKQGVVKLQG  DINNKGGLNI  TTNASGTQKT  IINGNITNEK
Hmw1com  FDNKGNSNIS  IAKGGARFK.  DIDNSKNLSI  TTNSSSTYRT  IISGNITNKN
Hmw2com  FTNNGTAEIN  ITQGVVKLG.  NVTNDGDLNI  TTHAKRNQRS  IIGGDIINNK Hmw3com  GDLNIIDKKS  DAEIQIGGNI  SQKEGNLTIS  SDKVNITNQI  TIKAGVEGGR
Hmw4com  GDLNIKNIKA  DAEIQIGGNI  SQKEGNLTIS  SDKVNITNQI  TIKAGVEGGR
Hmw1com  GDLNITNEGS  DTEMQIGGDI  SQKEGNLTIS  SDKINITKQI  TIKAGVDGEN
Hmw2com  GSLNITDSNN  DAEIQIGGNI  SQKEGNLTIS  SDKINITKQI  TIKKGIDGED 1051                                                           1100
Hmw3com  SDSSEAENAN  LTIQTKELKL  AGDLNISGFN  KAEITAKNGS  DLTIGNASGG
Hmw4com  SDSSEAENAN  LTIQTKELKL  AGDLNISGFN  KAEITAKNGS  DLTIGNASGG
Hmw1com  SDSDATNNAN  LTIKTKELKL  TQDLNISGFN  KAEITAKDGS  DLTIGNTNSA
Hmw2com  SSSDATSNAN  LTIKTKELKL  TEDLSISGFN  KAEITAKDGR  DLTIGNSNDG
```

FIG. 10I.

```
         1101                                                    1150
Hmw3com  N..ADAKKVT FDKVKDSKIS TDGHNVTLNS EVKT..SNGS SNAGNDNSTG
Hmw4com  N..ADAKKVT FDKVKDSKIS TDGHNVTLNS EVKT..SNGS SNAGNDNSTG
Hmw1com  D.GTNAKKVT FNQVKDSKIS ADGHKVTLHS KVETSGSNNN TEDSSDNNAG
Hmw2com  NSGAEAKKVT FNNVKDSKIS ADGHNVTLNS KVKTSSSNGG RESNSDNDTG 1151                                                    1200
Hmw3com  LTISAKDVTV NNNVTSHKTI NISAAAGNVT TKEGTTINAT TGSVEVTAQN
Hmw4com  LTISAKDVTV NNNVTSHKTI NISAAAGNVT TKEGTTINAT TGSVEVTAQN
Hmw1com  LTIDAKNVTV NNNITSHKAV SISATSGEIT TKTGTTINAT TGNVEIT....
Hmw2com  LTITAKNVEV NKDVTSLKTV NITA.SEKVT TTAGSTINAT NGKASIT....

1201                                                    1250
Hmw3com  GTIKGNITSQ NVTVTATENL VTTENAVINA TSGTVNISTK TGDIKGGIES
Hmw4com  GTIKGNITSQ NVTVTATENL VTTENAVINA TSGTVNISTK TGDIKGGIES
Hmw1com  .......... .......... .......... ........AQ TGDIKGGIES
```

FIG. 10J.

```
Hmw2com  ..........  ..........  ..........  ..........  ..........  ..........TK  T.........
              1251                                                                      1300
Hmw3com  TSGNVNITAS  GNTLKVSNIT  GQDVTVTADA  GALTTTAGST  ISATTGNANI
Hmw4com  TSGNVNITAS  GNTLKVSNIT  GQDVTVTADA  GALTTTAGST  ISATTGNANI
Hmw1com  SSGSVTLTAT  EGALAVSNIS  GNTVTVTANS  GALTTLAGST  IKG.TESVTT
Hmw2com  ..........  ..........  ..........  ..........  ..........
              1301                                                                      1350
Hmw3com  TTKTGDINGK  VESSSGSVTL  VATGATLAVG  NISGNTVTIT  ADSGKLTSTV
Hmw4com  TTKTGDINGK  VESSSGSVTL  VATGATLAVG  NISGNTVTIT  ADSGKLTSTV
Hmw1com  SSQSGDIG..  ..........  .........G  TISGGTVEVK  ATESLTTQSN
Hmw2com  ...GDIS..   ..........  .........G  TISGNTVSVS  ATVDLTTKSG
              1351                                                                      1400
Hmw3com  GSTINGTNSV  TTSSQSGDIE  GTISGNTVNV  TASTGDLTIG  NSAKVEAKNG
Hmw4com  GSTINGTNSV  TTSSQSGDIE  GTISGNTVNV  TASTGDLTIG  NSAKVEAKNG
```

FIG. 10K.

```
Hmw1com  SKIKATTGEA  NVTSATGTIG  GTISGNTVNV  TANAGDLTVG  NGAEINATEG
Hmw2com  SKIEAKSGEA  NVTSATGTIG  GTISGNTVNV  TANAGDLTVG  NGAEINATEG
                                                              1450

Hmw3com  AATLTAESGK  LTTQTGSSIT  SSNGQTTLTA  KDSSIAGNIN  AANVTLNTTG
Hmw4com  AATLTAESGK  LTTQTGSSIT  SSNGQTTLTA  KDSSIAGNIN  AANVTLNTTG
Hmw1com  AATLTTSSGK  LTTEASSHIT  SAKGQVNLSA  QDSSVAGSIN  AANVTLNTTG
Hmw2com  AATLTATGNT  LTTEAGSSIT  STKGQVDLLA  QNSSIAGNIN  AANVTLNTTG
                                                              1500

Hmw3com  TLTTTGDSKI  NATSGTLTIN  AKDAKLDGAA  SGDRTVVNAT  NASGSGNVTA
Hmw4com  TLTTTGDSKI  NATSGTLTIN  AKDAKLDGAA  SGDRTVVNAT  NASGSGNVTA
Hmw1com  TLTTVKGSNI  NATSGTLTIN  AKDAELNGAA  LGNHTVVNAT  NANGSGSVIA
Hmw2com  TLTTVAGSDI  KATSGTLTIN  AKDAKLNGDA  SGDSTEVNAV  NASGSGSVTA
                                                              1550
```

FIG. 10L.

```
                                                                    1600
         1551
Hmw3com  KTSSSVNITG DLNTINGLNI ISENGRNTVR LRGKEIDVKY IQPGVASVEE
Hmw4com  KTSSSVNITG DLNTINGLNI ISENGRNTVR LRGKEIDVKY IQPGVASVEE
Hmw1com  TTSSRVNITG DLITINGLNI ISKNGINTVL LKGVKIDVKY IQPGIASVDE
Hmw2com  ATSSSVNITG DLNTVNGLNI ISKDGRNTVR LRGKEIEVKY IQPGVASVEE 1601
Hmw3com  VIEAKRVLEK VKDLSDEERE TLAKLGVSAV RFVEPNNAIT VNTQNEFTTK
Hmw4com  VIEAKRVLEK VKDLSDEERE TLAKLGVSAV RFVEPNNAIT VNTQNEFTTK
Hmw1com  VIEAKRILEK VKDLSDEERE ALAKLGVSAV RFIEPNNTIT VDTQNEFATR
Hmw2com  VIEAKRVLEK VKDLSDEERE TLAKLGVSAV RFVEPNNTIT VNTQNEFTTR 1632
Hmw3com  PSSQVTISEG KACFSSGNGA RVCTNVADDG QQ
Hmw4com  PSSQVTISEG KACFSSGNGA RVCTNVADDG QQ
Hmw1com  PLSRIVISEG RACFSNSDGA TVCVNIADNG R.
Hmw2com  PSSQVIISEG KACFSSGNGA RVCTNVADDG QP
```

HIGH MOLECULAR WEIGHT SURFACE PROTEINS OF NON-TYPEABLE HAEMOPHILUS

This is a continuation of application Ser. No. 08/302,832, filed as PCT/US93/02166 Mar. 16, 1993, now U.S. patent Ser. No. 5,603,938.

FIELD OF INVENTION

This invention relates to high molecular weight proteins of non-typeable haemophilus.

BACKGROUND OF THE INVENTION

Non-typeable *Haemophilus influenzae* are non-encapslated organisms that are defined by their lack of reactivity with antisera against known *H. influenzae* capsular antigens.

These organisms commonly inhabit the upper respiratory tract of humans and are frequently responsible for infections, such as otitis media, sinusitis, conjunctivitis, bronchitis and pneumonia. Since these organisms do not have a polysaccharide capsule, they are not controlled by the present *Haemophilus influenzae* type b (Hib) vaccines, which are directed towards Hib bacterial capsular polysaccharides. The non-typeable strains, however, do produce surface antigens that can elicit bactericidal antibodies. Two of the major outer membrane proteins, P2 and P6, have been identified as targets of human serum bactericidal activity. However, it has been shown that the P2 protein Haemophilus strains. Thus, a P2-based vaccine would not protect against all strains of the organism.

There have previously been identified by Barenkamp et al (*Pediatr. Infect. Dis. J.*, 9:333–339, 1990) a group of high-molecular-weight (HMW) proteins that appeared to be major targets of antibodies present in human convalescent sera. Examination of a series of middle ear isolates revealed the presence of one or two such proteins in most strains. However, prior to the present invention, the structures of these proteins were unknown as were pure isolates of such proteins.

SUMMARY OF THE INVENTION

The inventors, in an effort to further characterize the high molecular weight (HMW) Haemophilus proteins, have cloned, expressed and sequenced the genes coding for two immunodominant HMW proteins (designated HMW1 and HMW2) from a prototype non-typeable Haemophilus strain and have cloned, expressed and almost completely sequenced the genes coding for two additional immunodominant HMW proteins (designated HMW3 and HMW4) from another non-typeable Haemophilus strain.

In accordance with one aspect of the present invention, therefore, there is provided an isolated and purified gene coding for a high molecular weight protein of a non-typeable Haemophilus strain, particularly a gene coding for protein HMW1, HMW2, HMW3 or HMW4, as well as any variant or fragment of such protein which retains the immunological ability to protect against disease caused by a non-typeable Haemophilus strain. In another aspect, the invention provides a high molecular weight protein of non-typeable *Haemophilus influenzae* which is encoded by these genes.

BRIEF DESCRIPTION OF DRAWINGS

FIGS. 1A–1G is a DNA sequence of a gene coding for protein HMW1 (SEQ ID NO: 1);

FIGS. 2A–2B is a derived amino acid sequence of protein HMW1 (SEQ ID NO: 2);

FIGS. 3A–3G is a DNA sequence of a gene coding for protein HMW2 (SEQ ID NO: 3);

FIGS. 4A–4B is a derived amino acid sequence of HMW2 (SEQ ID NO: 4);

FIGS. 6A–6L contains the DNA sequence of a gene cluster for the hmw1 gene (SEQ ID NO: 5), comprising nucleotides 351 to 4958 (ORF a) (as in FIG. 1), as well as two additional downstream genes in the 3' flanking region, comprising ORFs b, nucleotides 5114–6748 and c nucleotides 7062–9011;

FIGS. 7A–7L contains the DNA sequence of a gene cluster for the hmw2 gene (SEQ ID NO: 6), comprising nucleotides 792 to 5222 (ORF a) (as in FIG. 3), as well as two additional downstream genes in the 3' flanking region, comprising ORFs b, nucleotides 5375–7009 and c, nucleotides 7249–9198;

FIGS. 8A–8G is a partial DNA sequence of a gene coding for protein HMW3 (SEQ ID NO: 7);

FIGS. 9A–9F is a partial DNA sequence of a gene coding for protein HMW4 (SEQ ID NO: 8); and FIGS. 10A–10L is a comparison table for the derived amino acid sequence for proteins HMW1, HMW2, HMW3 and HMW4.

GENERAL DESCRIPTION OF INVENTION

Figure 5A:
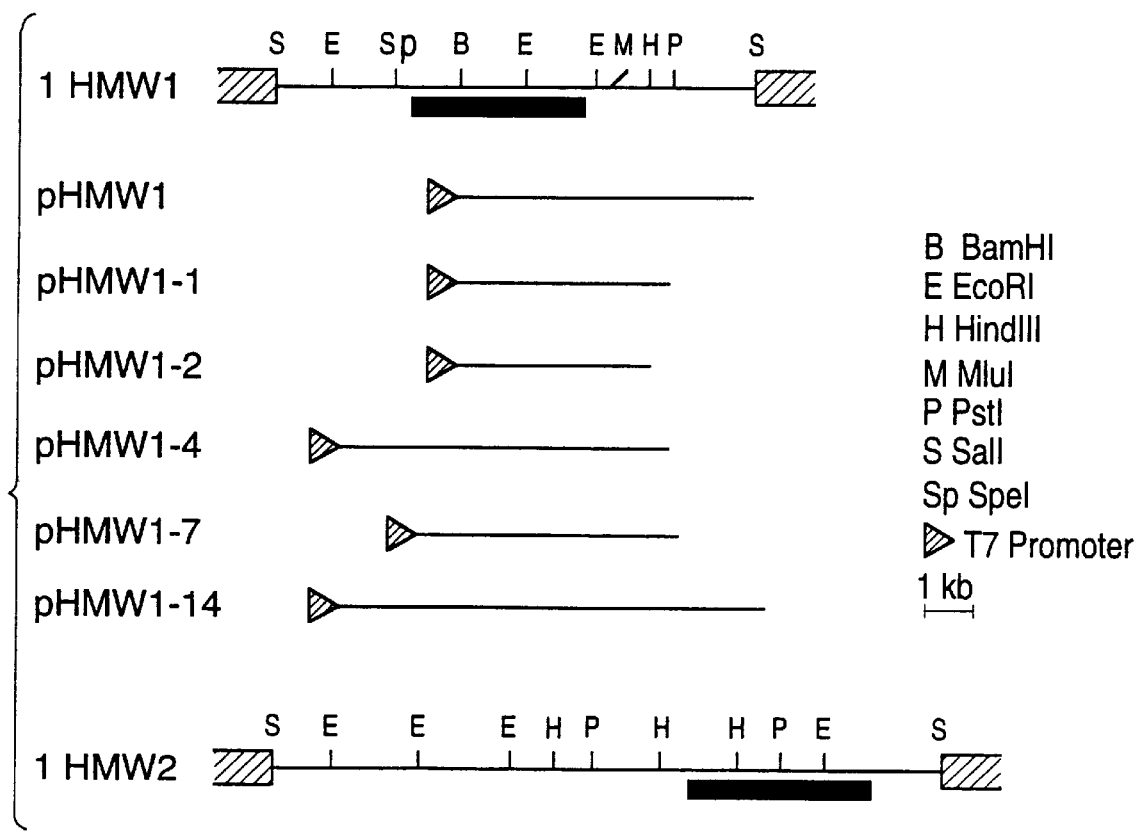
FIG. 5A shows restriction maps of representative recombinant phages which contained the HMW1 or HMW2 structural genes, the locations of the structural genes being indicated by the shaded bars.

The DNA sequences of the genes coding for HMW1 and HMW2, shown in FIGS. 1 and 3 respectively, were shown to be about 80% identical, with the first 1259 base pairs of the genes being identical. The derived amino acid sequences of the two HMW proteins, shown in FIGS. 2 and 4 respectively, are about 70% identical. Furthermore, the encoded proteins are antigenically related to the filamentous hemagglutinin surface protein of *Bordetella pertussis*. A monoclonal antibody prepared against filamentous hemagglutinin (FHA) of *Bordetella pertussis* was found to recognize both of the high molecular weight proteins. This data suggests that the HMW and FHA proteins may serve similar biological functions. The derived amino acid sequences of the HMW1 and HMW2 proteins show sequence similarity to that for the FHA protein. It has further been shown that these antigenically-related proteins are produced by the majority of the non-typeable strains of Haemophilus. Antisera raised against the protein expressed by the HMW1 gene recognizes both the HMW2 protein and the *B. pertussis* FHA. The present invention includes an isolated and purified high molecular weight protein of non-typeable haemophilus which is antigenically related to the *B. pertussis* FHA, which may be obtained from natural sources or produced recombinantly.

A phage genomic library of a known strain of non-typeable Haemophilus was prepared by standard methods and the library was screened for clones expressing high molecular weight proteins, using a high titre antiserum against HMW's. A number of strongly reactive DNA clones were plaque-purified and sub-cloned into a T7 expression plasmid. It was found that they all expressed either one or the other of the two high-molecular-weight proteins designated HMW1 and HMW2, with apparent molecular weights of 125 and 120 kDa, respectively, encoded by open reading frames of 4.6 kb and 4.4 kb, respectively.

Representative clones expressing either HMW1 or HMW2 were further characterized and the genes isolated, purified and sequenced. The DNA sequence of HMW1 is shown in FIG. 1 and the corresponding derived amino acid sequence in FIG. 2. Similarly, the DNA sequence of HMW2 is shown in FIG. 3 and the corresponding derived amino acid sequence in FIG. 4. Partial purification of the isolated proteins and N-terminal sequence analysis indicated that the expressed proteins are truncated since their sequence starts at residue number 442 of both full length HMW1 and HMW2 gene products.

Subcloning studies with respect to the hmw1 and hmw2 genes indicated that correct processing of the HMW proteins required the products of additional downstream genes. It has been found that both the hmw1 and hmw2 genes are flanked by two additional downstream open reading frames (ORFs), designated b and c, respectively, (see FIGS. 6 and 7).

The b ORFs are 1635 bp in length, extending from nucleotides 5114 to 6748 in the case of hmw1 and nucleotides 5375 to 7009 in the case of hmw2, with their derived amino acid sequences 99% identical. The derived amino acid sequences demonstrate similarity with the derived amino acid sequences of two genes which encode proteins required for secretion and activation of hemolysins of *P. mirabilis* and *S. marcescens*.

The c ORFs are 1950 bp in length, extending from nucleotides 7062 to 9011 in the case of hmw1 and nucleotides 7249 to 9198 in the case of hmw2, with their derived amino acid sequences 96% identical. The hmw1 c ORF is preceded by a series of 9 bp direct tandem repeats. In plasmid subclones, interruption of the hmw1 b or c ORF results in defective processing and secretion of the hmw1 structural gene product.

The two high molecular weight proteins have been isolated and purified and shown to be partially protective against otitis media in chinchillas and to function as adhesins. These results indicate the potential for use of such high molecular proteins and structurally-related proteins of other non-typeable strains of *Haemophilus influenzae* as components in non-typeable *Haemophilus influenzae* vaccines.

Since the proteins provided herein are good cross-reactive antigens and are present in the majority of non-typeable Haemophilus strains, it is evident that these HMW proteins may become integral constituents of a universal Haemophilus vaccine. Indeed, these proteins may be used not only as protective antigens against otitis, sinusitis and bronchitis caused by the non-typeable Haemophilus strains, but also may be used as carriers for the protective Hib polysaccharides in a conjugate vaccine against meningitis. The proteins also may be used as carriers for other antigens, haptens and polysaccharides from other organisms, so as to induce immunity to such antigens, haptens and polysaccharides.

The nucleotide sequences encoding two high molecular weight proteins of a different non-typeable Haemophilus strain (designated HMW3 and HMW4) have been largely elucidated, and are presented in FIGS. 8 and 9. HMW3 has an apparent molecular weight of 125 kDa while HMW4 has an apparent molecular weight of 123 kDa. These high molecular weight proteins are antigenically related to the HMW1 and HMW2 proteins and to FHA. Sequence analysis of HMW3 is approximately 85% complete and of HMW4 95% complete, with short stretches at the 5'-ends of each gene remaining to be sequenced.

FIG. 10 contains a multiple sequence comparison of the derived amino acid sequences for the four high molecular weight proteins identified herein. As may be seen from this comparison, stretches of identical peptide sequence may be found throughout the length of the comparison, with HMW3 more closely resembling HMW1 and HMW4 more closely resembling HMW2. This information is highly suggestive of a considerable sequence homology between high molecular weight proteins from various non-typeable Haemophilus strains.

In addition, mutants of non-typeable *H. influenzae*. strains that are deficient in expression of HMW1 or HMW2 or both have been constructed and examined for their capacity to adhere to cultured human opithelial cells. The hmw1 and hmw2 gene clusters have been expressed in *E. coli* and have been examined for in vitro adherence. The results of such experimentation demonstrate that both HMW1 and HMW2 mediate attachment and hence are adhesins and that this function is present even in the absence of other *H. influenzae* surface structures.

With the isolation and purification of the high molecular weight proteins, the inventors are able to determine the major protective epitopes by conventional epitope mapping and synthesize peptides corresponding to these determinants to be incorporated in fully synthetic or recombinant vaccines. Accordingly, the invention also comprises a synthetic peptide having an amino acid sequence corresponding to at least one protective epitope of a high molecular weight protein of a non-typeable *Haemophilus influenzae*. Such peptides are of varying length that constitute portions of the high-molecular-weight proteins, that can be used to induce immunity, either directly or as part of a conjugate, against the relative organisms and thus constitute vaccines for protection against the corresponding diseases.

The present invention also provides any variant or fragment of the proteins that retains the potential immunological ability to protect against disease caused by non-typeable Haemophilus strains. The variants may be constructed by partial deletions or mutations of the genes and expression of the resulting modified genes to give the protein variations.

EXAMPLES

Example 1

Non-typeable *H. influenzae* strains 5 and 12 were isolated in pure culture from the middle ear fluid of children with acute otitis media. Chromosomal DNA from strain 12, providing genes encoding proteins HMW1 and HMW2, was prepared by preparing Sau3A partial restriction digests of chromosomal DNA and fractionating on sucrose gradients. Fractions containing DNA fragments in the 9 to 20 kbp range were pooled and a library was prepared by ligation into λEMBL3 arms. Ligation mixtures were packaged in vitro and plate-amplified in a P2 lysogen of *E. coli* LE392.

Figure 5B:
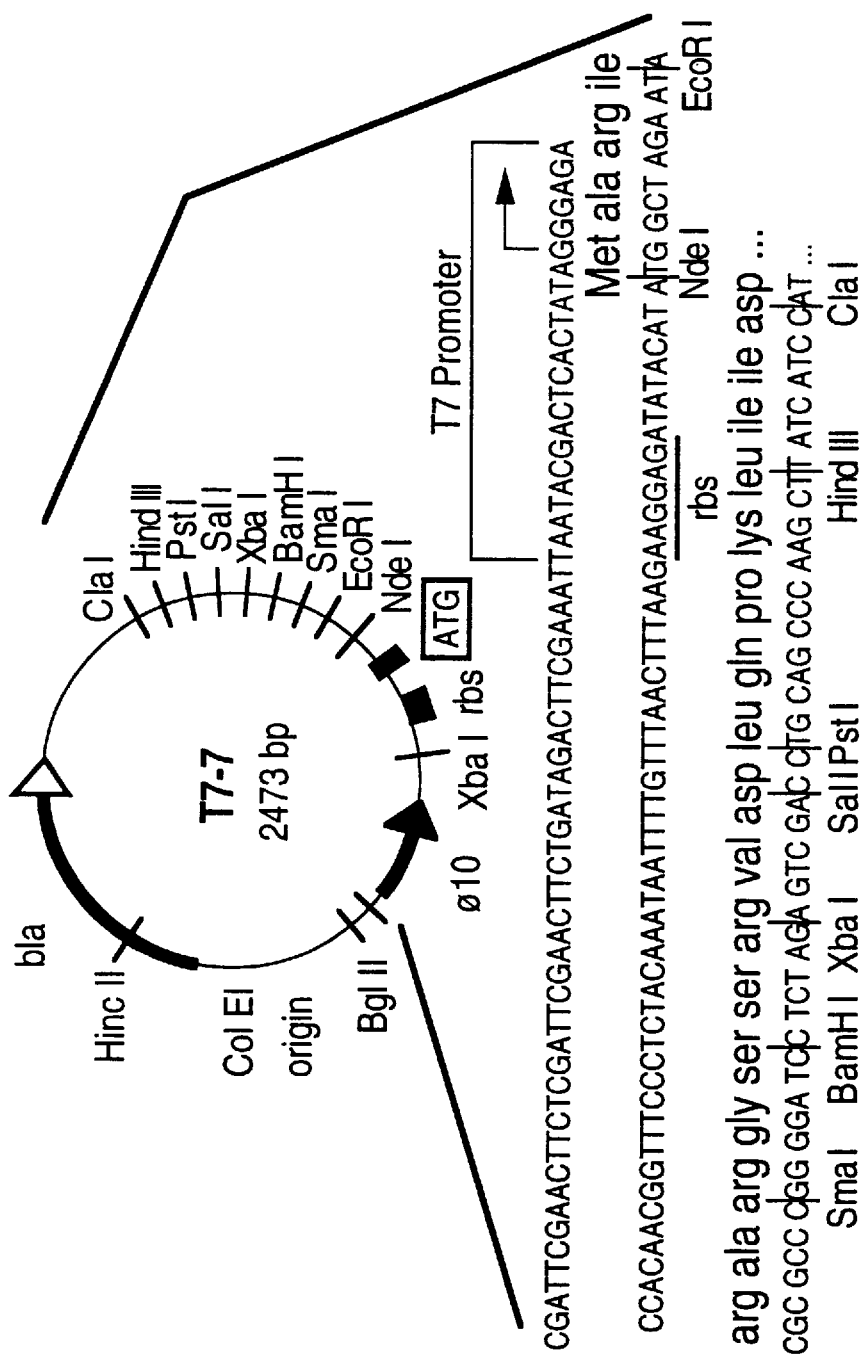
FIG. 5B shows the restriction map of the T7 expression vector pT7-7.

For plasmid subcloning studies, DNA from a representative recombinant phage was subcloned into the T7 expression plasmid pT7-7, containing the T7 RNA polymerase promoter φ10, a ribosome-binding site and the translational start site for the T7 gene 10 protein upstream from a multiple cloning site (see FIG. 5B).

DNA sequence analysis was performed by the dideoxy method and both strands of the HMW1 gene and a single strand of the HMW2 gene were sequenced.

Western immunoblot analysis was performed to identify the recombinant proteins being produced by reactive phage clones. Phage lysates grown in LE392 cells or plaques picked directly from a lawn of LE392 cells on YT plates were solubilized in gel electrophoresis sample buffer prior to electrophoresis. Sodium dodecyl sulfate (SDS)-polyacrylamide gel electrophoresis was performed on 7.5% or 11% polyacrylamide modified Laemmli gels. After transfer of the proteins to nitrocellulose sheets, the sheets were probed sequentially with an E. coli-absorbed human serum sample containing high-titer antibody to the high-molecular-weight proteins and then with alkaline phosphatase-conjugated goat anti-human immunoglobulin G (IgG) second antibody. Sera from healthy adults contains high-titer antibody directed against surface exposed high-molecular-weight proteins of non-typeable H. influenzae. One such serum sample was used as the screening antiserum after having been extensively absorbed with LE392 cells.

To identify recombinant proteins being produced by E. coli transformed with recombinant plasmids, the plasmids of interest were used to transform E. coli BL21 (DE3)/pLysS. The transformed strains were grown to an $A_{600}$ of 0.5 in L broth containing 50 μg of ampicillin per ml. IPTG was then added to 1 mM. One hour later, cells were harvested, and a sonicate of the cells was prepared. The protein concentrations of the samples were determined by the bicinchoninic acid method. Cell sonicates containing 100 μg of total protein were solubilized in electrophoresis sample buffer, subjected to SDS-polyacrylamide gel electrophoresis, and transferred to nitrocellulose. The nitrocellulose was then probed sequentially with the E. coli-absorbed adult serum sample and than with alkaline phosphatase-conjugated goat anti-human IgG second antibody.

Western (immunoblot analysis also was performed to determine whether homologous and heterologous non-typeable H. influenzae strains expressed high-molecular-weight proteins antigenically related to the protein encoded by the cloned HMW1 gene (rHMW1). Cell sonicates of bacterial cells were solubilized in electrophoresis sample buffer, subjected to SDS-polyacrylamide gel electrophoresis, and transferred to nitrocellulose. Nitrocellulose was probed sequentially with polyclonal rabbit rHMW1 antiserum and then with alkaline phosphatase-conjugated goat anti-rabbit IgG second antibody.

Finally, Western immunoblot analysis was performed to determine whether non-typeable Haemophilus strains expressed proteins antigenically related to the filamentous hemagglutinin protein of Bordetella pertussis. Monoclonal antibody X3C, a murine immunoglobulin G (IgG) antibody which recognizes filamentous hemagglutinin, was used to probe cell sonicates by Western blot. An alkaline phosphatase-conjugated goat anti-mouse IgG second antibody was used for detection.

To generate recombinant protein antiserum, E. coli BL21 (DE3)/pLysS was transformed with pHMW1-4, and expression of recombinant protein was induced with IPTG, as described above. A cell sonicate of the bacterial cells was prepared and separated into a supernatant and pellet fraction by centrifugation at 10,000×g for 30 min. The recombinant protein fractionated with the pellet fraction. A rabbit was subcutaneously immunized on biweekly schedule with 1 mg of protein from the pellet fraction, the first dose given with Freund's complete adjuvant and subsequent doses with Freund's incomplete adjuvant. Following the fourth injection, the rabbit was bled. Prior to use in the Western blot assay, the antiserum was absorbed extensively with sonicates of the host E. coli strain transformed with cloning vector alone.

To assess the sharing of antigenic determinants between HMW1 and filamentous hemagglutinin, enzyme-linked immunosorbent assay (ELISA) plates (Costar, Cambridge, Mass.) were coated with 60 μl of a 4-ug/ml solution of filamentous hemagglutinin in Dulbecco's phosphate-buffered saline per well for 2 h at room temperature. Wells were blocked for 1 h with 1% bovine serum albumin in Dulbecco's phosphate-buffered saline prior to addition of serum dilutions. rHMW1 antiserum was serially diluted in 0.1% Brij (Sigma, St. Louis, Mo.) in Dulbecco's phosphate-buffered saline and incubated for 3 h at room temperature. After being washed, the plates were incubated with peroxidase-conjugated goat anti-rabbit lgG antibody (Bio-Rad) for 2 h at room temperature and subsequently developed with 2,2'-azino-bis(3-ethylbenzthiazoline-6-sulfonic acid) (Sigma) at a concentration of 0.54 in mg/ml in 0.1M sodium citrate buffer, pH 4.2, containing 0.03% $H_2O_2$. Absorbances were read on an automated ELISA reader.

Recombinant phage expressing HMW1 or HMW2 were recovered as follows. The non-typeable H. influenzae strain 12 genomic library was screened for clones expressing high-molecular-weight proteins with an E. coli-absorbed human serum sample containing a high titer of antibodies directed against the high-molecular-weight proteins.

Numerous strongly reactive clones were identified along with more weakly reactive ones. Twenty strongly reactive clones were plaque-purified and examined by Western blot for expression of recombinant proteins. Each of the strongly reactive clones expressed one of two types of high-molecular-weight proteins, designated HMW1 and HMW2. The major immunoreactive protein bands in the HMW1 and HMW2 lysates migrated with apparent molecular masses of 125 and 120 kDa, respectively. In addition to the major bands, each lysate contained minor protein bands of higher apparent molecular weight. Protein bands seen in the HMW2 lysates at molecular masses of less than 120 kDa were not regularly observed and presumably represent proteolytic degradation products. Lysates of LE392 infected with the λEMBL3 cloning vector alone were non-reactive when immunologically screened with the same serum sample. Thus, the observed activity was not due to cross-reactive E. coli proteins or λEMBL3-encoded proteins. Furthermore, the recombinant proteins were not simply binding immunoglobulin nonspecifically, since the proteins were not reactive with the goat anti-human IgG conjugate alone, with normal rabbit sera, or with serum from a number of healthy young infants.

Representative clones expressing either the HMW1 or HMW2 recombinant proteins were characterized further. The restriction maps of the two phage types were different from each other, including the regions encoding the HMW1 and HMW2 structural genes. FIG. 5A shows restriction maps of representative recombinant phage which contained the HMW1 or HMW2 structural genes. The locations of the structural genes are indicated by the shaded bars.

HMW1 plasmid subclones were constructed by using the T7 expression plasmid T7-7 (FIGS. 5A and B). HMW2 plasmid subclones also were constructed, and the results with these latter subclones were similar to those observed with the HMW1 constructs.

The approximate location and direction of transcription of the HMW1 structure gene were initially determined by using plasmid pHMW1 (FIG. 5A). This plasmid was constructed by inserting the 8.5-kb BamHI-SalI fragment from λHMW1 into BamHI- and SalI-cut pT7-7. E. coli transformed with pHMW1 expressed an immunoreactive recombinant protein with an apparent molecular mass of 115 kDa, which was strongly inducible with IPTG. This protein was significantly smaller than the 125-kDa major protein expressed by the parent phage, indicating that it either was being expressed as a fusion protein or was truncated at the carboxy terminus.

To more precisely localize the 3' end of the structural gene, additional plasmids were constructed with progressive deletions from the 3' end of the pHMW1 construct. Plasmid pHMW1-1 was constructed by digestion of pHMW1 with PstI, isolation of the resulting 8.8-kb fragment, and religation. Plasmid pHMW1-2 was constructed by digestion of pHMW1 with HindIII, isolation of the resulting 7.5-kb fragment, and religation. E. coli transformed with either plasmid pHMW1-1 or pHMW1-2 also expressed an immunoreactive recombinant protein with an apparent molecular mass of 115 kDa. These results indicated that the 3' end of the structural gene was 5' of the HindIII site.

To more precisely localize the 5' end of the gene, plasmids pHMW1-4 and pHMW1-7 were constructed. Plasmid pHMW1-4 was constructed by cloning the 5.1-kb BamHI-HindIII fragment from λHMW1 into a pT7-7 derived plasmid containing the upstream 3.8-kb EcoRI-BamHi fragment. E. coli transformed with pHMW1-4 expressed an immunoreactive protein with an apparent molecular mass of approximately 160 kDa. Although protein production was inducible with IPTG, the levels of protein production in these transformants were substantially lower than those with the pHMW1-2 transformants described above. Plasmid pHMW1-7 was constructed by digesting pHMW1-4 with NdeI and SpeI. The 9.0-kbp fragment generated by this double digestion was isolated, blunt ended, and religated. E. coli transformed with pHMW1-7 also expressed an immunoreactive protein with an apparent molecular mass of 160 kDa, a protein identical in size to that expressed by the pHMW1-4 transformants. The result indicated that the initiation codon for the HMW1 structural gene was 3' of the SpeI site. DNA sequence analysis confirmed this conclusion.

As noted above, the λHMW1 phage clones expressed a major immunoreactive band of 125 kDa, whereas the HMW1 plasmid clones pHMW1-4 and pHMW1-7, which contained what was believed to be the full-length gene, expressed an immunoreactive protein of approximately 160 kDa. This size discrepancy was disconcerting. One possible explanation was that an additional gene or genes necessary for correct processing of the HMW1 gene product were deleted in the process of subcloning. To address this possibility, plasmid pHMW1-14 was constructed. This construct was generated by digesting pHMW1 with NdeI and MluI and inserting the 7.6-kbp NdeI-MluI fragment isolated from pHMW1-4. Such a construct would contain the full-length HMW1 gene as well as the DNA 3' of the HMW1 gene which was present in the original HMW1 phage. E. coli transformed with this plasmid expressed major immunoreactive proteins with apparent molecular masses of 125 and 160 kDa as well as additional degradation products. The 125- and 160-kDa bands were identical to the major and minor immunoreactive bands detected in the HMW1 phage lysates. Interestingly, the pHMW1-14 construct also expressed significant amounts of protein in the uninduced condition, a situation not observed with the earlier constructs.

The relationship between the 125- and 160-kDa proteins remains somewhat unclear. Sequence analysis, described below, reveals that the HMW1 gene would be predicted to encode a protein of 159 kDa. It is believed that the 160-kDa protein is a precursor form of the mature 125-kDa protein, with the conversion from one protein to the other being dependent on the products of the two downstream genes.

Sequence analysis of the HMW1 gene (FIG. 1) revealed a 4,608-bp open reading frame (ORF), beginning with an ATG codon at nucleotide 351 and ending with a TAG stop codon at nucleotide 4959. A putative ribosome-binding site with the sequence AGGAG begins 10 bp upstream of the putative initiation codon. Five other in-frame ATG codons are located within 250 bp of the beginning of the ORF, but none of these is preceded by a typical ribosome-binding site. The 5'-flanking region of the ORF contains a series of direct tandem repeats, with the 7-bp sequence ATCTTTC repeated 16 times. These tandem repeats stop 100 bp 5' of the putative initiation codon. An 8-bp inverted repeat characteristic of a rho-independent transcriptional terminator is present, beginning at nucleotide 4983, 25 bp 3' of the presumed translational stop. Multiple termination codons are present in all three reading frames both upstream and downstream of the ORF. The derived amino acid sequence of the protein encoded by the HMW1 gene (FIG. 2) has a molecular weight of 159,000, in good agreement with the apparent molecular weights of the proteins expressed by the HMW1-4 and HMW1-7 transformants. The derived amino acid sequence of the amino terminus does not demonstrate the characteristics of a typical signal sequence. The BamHI site used in generation of pHMW1 comprises bp 1743 through 1748 of the nucleotide sequence. The ORF downstream of the BamHI site would be predicted to encode a protein of 111 kDa, in good agreement with the 115 kDa estimated for the apparent molecular mass of the pHMW1-encoded fusion protein.

The sequence of the HMW2 gene (FIG. 2) consists of a 4,431-bp ORF, beginning with an ATG codon at nucleotide 352 and ending with a TAG stop codon at nucleotide 4783. The first 1,259 bp of the ORF of the HMW2 gene are identical to those of the HMW1 gene. Thereafter, the sequences begin to diverge but are 80% identical overall. With the exception of a single base addition at nucleotide 93 of the HMW2 sequence, the 5'-flanking regions of the HMW1 and HMW2 genes are identical for 310 bp upstream from the respective initiation codons. Thus, the HMW2 gene is preceded by the same set of tandem repeats and the same putative ribosome-binding site which lies 5' of the HMW1 gene. A putative transcriptional terminator identical to that identified 3' of the HMW1 ORF is noted, beginning at nucleotide 4804. The discrepancy in the lengths of the two genes is principally accounted for by a 186-bp gap in the HMW2 sequence, beginning at nucleotide position 3839. The derived amino acid sequence of the protein encoded by the HMW2 gene (FIG. 4) has a molecular weight of 155,000 and is 71% identical with the derived amino acid sequence of the HMW1 gene.

The derived amino acid sequences of both the HMW1 and HMW2 genes (FIGS. 2 and 4) demonstrated sequence similarity with the derived amino acid sequence of filamentous hemagglutinin of Bordetella pertussis, a surface-associated protein of this organism. The initial and optimized TFASTA scores for the HMW1-filamentous hemagglutinin sequence comparison were 87 and 186, respectively, with a word size of 2. The z score for the comparison was 45.8. The initial and optimized TFASTA scores for the HMW2-filamentous hemagglutinin sequence comparison were 68 and 196, respectively. The z score for the latter comparison was 48.7. The magnitudes of the initial and optimized TFASTA scores and the z scores suggested that a biologically significant relationship existed between the HMW1 and HMW2 gene products and filamentous hemagglutinin. When the derived amino acid sequences of HMW1, HMW2, and filamentous hemagglutinin genes were aligned and compared, the similarities were most notable at the amino-terminal ends of the three sequences. Twelve of the first 22 amino acids in the predicted peptide sequences were identical. In additional, the sequences demonstrated a common five-amino-acid stretch, Asn-Pro-Asn-Gly-Ile, and several shorter stretches of sequence identity within the first 200 amino acids.

Example 2

To further explore the HMW1-filamentous hemagglutinin relationship, the ability of antiserum prepared against the HMW1-4 recombinant protein (rHMW1) to recognize purified filamentous hemagglutinin was assessed. The rHMW1 antiserum demonstrated ELISA reactivity with filamentous hemagglutinin in a dose-dependent manner. Preimmune rabbit serum had minimal reactivity in this assay. The rHMW1 antiserum also was examined in a Western blot assay and demonstrated weak but positive reactivity with purified filamentous hemagglutinin in this system also.

To identify the native Haemophilus protein corresponding to the HMW1 gene product and to determine the extent to which proteins antigenically related to the HMW1 cloned gene product were common among other non-typeable *H. influenzae* strains, a panel of Haemophilus strains was screened by Western blot with the rHMW1 antiserum. The antiserum recognized both a 125- and a 120-kDa protein band in the homologous strain 12, the putative mature protein products of the HMW1 and HMW2 genes, respectively.

When used to screen heterologous non-typeable *H. influenzae* strains, rHMW1 antiserum recognized high-molecular-weight proteins in 75% of 125 epidemiologically unrelated strains. In general, the antiserum reacted with one or two protein bands in the 100- to 150-kDa range in each of the heterologous strains in a pattern similar but not identical to that seen in the homologous strain.

Monoclonal antibody X3C is a murine IgG antibody directed against the filamentous hemagglutinin protein of *B. pertussis*. This antibody can inhibit the binding of *B. pertussis* cells to Chinese hamster ovary cells and HeLa cells in culture and will inhibit hemagglutination of erythrocytas by purified filamentous hemagglutinin. A Western blot assay was performed in which this monoclonal antibody was screened against the same panel of non-typeable *H. influenzae* strains discussed above. Monoclonal antibody X3C recognized both the high-molecular-weight proteins in non-typeable *H. influenzae* strain 12 which were recognized by the recombinant-protein antiserum. In addition, the monoclonal antibody recognized protein bands in a subset of heterologous non-typeable *H. influenzae* strains which were identical to those recognized by the recombinant-protein antiserum. On occasion, the filamentous hemagglutinin monoclonal antibody appeared to recognize only one of the two bands which had been recognized by the recombinant-protein antiserum. Overall, monoclonal antibody X3C recognized high-molecular-weight protein bands identical to those recognized by the rHMW1 antiserum in approximately 35% of our collection of non-typeable *H. influenzae* strains.

Example 3

Mutants deficient in expression of HMW1, MW2 or both proteins were constructed to examine the role of these proteins in bacterial adherence. The following strategy was employed. pHMW1-14 (see Example 1, FIG. 5A) was digested with BamHI and then ligated to a kanamycin cassette isolated on a 1.3-kb BamH1 fragment from pUC4K. The resultant plasmid (pHMW1-17) was linearized by digestion with XbaI and transformed into non-typeable *H. influenzae* strain 12, followed by selection for kanamycin resistant colonies. Southern analysis of a series of these colonies demonstrated two populations of transformants, one with an insertion in the HMW1 structural gene and the other with an insertion in the HMW2 structural gene. One mutant from each of these classes was selected for further studies.

Mutants deficient in expression of both proteins were recovered using the following protocol. After deletion of the 2.1-kp fragment of DNA between two EcoRI sites spanning the 3'-portion of the HMW1 structural gene in pHMW-15, the kanamycin cassette from pUC4K was inserted as a 1.3-kb EcoR1 fragment. The resulting plasmid (pHMW1-16)was linearized by digestion with XbaI and transformed into strain 12, followed again by selection for kanamycin resistant colonies. Southern analysis of a representative sampling of these colonies demonstrated that in seven of eight cases, insertion into both the HMW1 and HMW2 loci had occurred. One such mutant was selected for further studies.

To confirm the intended phenotypes, the mutant strains were examined by Western blot analysis with a polyclonal antiserum against recombinant HMW1 protein. The parental strain expressed both the 125-kD HMW1 and the 120-kD HMW2 protein. In contrast, the HMW2 mutant failed to express the 120-kD protein, and the HMW1 mutant failed to express the 125-kD protein. The double mutant lacked expression of either protein. On the basis of whole cell lysates, outer membrane profiles, and colony morphology, the wild type strain and the mutants were otherwise identical with one another. Transmission electron microscopy demonstrated that none of the four strains expressed pili.

The capacity of wild type strain 12 to adhere to Chang epithelial cells was examined. In such assays, bacteria were inoculated into broth and allowed to grow to a density of $-2 \times 10^9$ cfu/ml. Approximately $2 \times 10^7$ cfu were inoculated onto epithelial cell monolayers, and plates were gently centrifuged at 165×g for 5 minutes to facilitate contact between bacteria and the epithelial surface. After incubation for 30 minutes at 37° C. in 5% $CO_2$, monolayers were rinsed 5 times with PBS to remove nonadherent organisms and were treated with trypsin-EDTA (0.05% trypsin, 0.5% EDTA) in PBS to release them from the plastic support. Well contents were agitated, and dilutions were plated on solid medium to yield the number of adherent bacteria per monolayer. Percent adherence was calculated by dividing the number of adherent cfu per monolayer by the number of inoculated cfu.

As depicted in Table 1 below (the Tables appear at the end of the descriptive text), this strain adhered quite efficiently, with nearly 90% of the inoculum binding to the monolayer. Adherence by the mutant expressing HMW1 but not HMW2 (HMW2⁻) was also quite efficient and comparable to that by the wild type strain. In contrast, attachment by the strain expressing HMW2 but deficient in expression of HMW1 (HMW1⁻) was decreased about 15-fold relative to the wild type. Adherence by the double mutant (HMW1⁻/HMW2⁻) was decreased even further, approximately 50-fold compared with the wild type and approximately 3-fold compared with the HMW1 mutant. Considered together, these results suggest that both the HMW1 protein and the, HMW2 protein influence attachment to Chang epithelial cells. Interestingly, optimal adherence to this cell line appears to require HMW1 but not HMW2.

Example 4

Using the plasmids pHMW1-16 and pHMW1-17 (see Example 3) and following a scheme similar to that employed with strain 12 as described in Example 3, three non-typeable Haemophilus strain 5 mutants were isolated, including one with the kanamycin gene inserted into the hmw1-like (designated hmw3) locus, a second with an insertion in the hmw2-like (designated hmw4) locus, and a third with insertions in both loci. As predicted, Western immunoblot analysis demonstrated that the mutant with insertion of the kanamycin cassette into the hmw1-like locus had lost expression of the HMW3 125-kD protein, while the mutant with insertion into the hmw2-like locus failed to express the HMW4 123-kD protein. The mutant with a double insertion was unable to express either of the high molecular weight proteins.

As shown in Table 1 below, wild type strain 5 demonstrated high level adherence, with almost 80% of the inoculum adhering per monolayer. Adherence by the mutant deficient in expression of the HMW2-like protein was also quite high. In contrast, adherence by the mutant unable to express the, HMW1-like protein was reduced about 5-fold relative to the wild type, and attachment by the double mutant was diminished even further (approximately 25-fold). Examination of Giemsa-stained samples confirmed these observations (not shown). Thus, the results with strain 5 corroborate the findings with strain 12 and the HMW1 and HMW2 proteins.

Example 5

To confirm an adherence function for the HMW1 and HMW2 proteins and to examine the effect of HMW1 and HMW2 independently of other *H. influenzae* surface structures, the hmw1 and the hmw2 gene clusters were introduced into *E. coli* DH5α, using plasmids pHMW1-14 and pHMW2-21, respectively. As a control, the cloning vector, pT7-7, was also transformed into *E. coli* DH5α. Western blot analysis demonstrated that *E. coli* DH5α containing the hmw1 genes expressed a 125 kDa protein, while the same strain harboring the hmw2 genes expressed a 120-kDa protein. *E. coli* DH5α containing pT7-7 failed to react with antiserum against recombinant HMW1. Transmission electron microscopy revealed no pili or other surface appendages on any of the *E. coli* strains.

Adherence by the *E. coli* strains was quantitated and compared with adherence by wild type non-typeable *H. influenzae* strain 12. As shown in Table 2 below, adherence by *E. coli* DH5α containing vector alone was less than 1% of that for strain 12. In contrast, *E. coli* DH5α harboring the hmw1 gene cluster demonstrated adherence levels comparable to those for strain 12. Adherence by *E. coli* DH5α containing the hmw2 genes was approximately 6-fold lower than attachment by strain 12 but was increased 20-fold adherence by *E. coli* DH5α with pT7-7 alone. These results indicate that the HMW1 and HMW2 proteins are capable of independently mediating attachment to Chang conjunctival cells. These results are consistent with the results with the *H. influenzae* mutants reported in Example 3 and 4, providing further evidence that, with Chang epithelial cells, HMW1 is a more efficient adhesin than is HMW2.

Experiments with *E. coli* HB101 harboring pT7-7, pHMW1-14, or pHMW2-21 confirmed the results obtained with the DH5α derivatives (see Table 2).

Example 6

HMW1 and HMW2 were isolated and purified from non-typeable *H. influenzae* (NTHI) strain 12 in the following manner. Non-typeable Haemophilus bacteria from frozen stock culture were streaked onto a chocolate plate and grown overnight at 37° C. in an incubator with 5% $CO_2$. 50 ml starter culture of brain heart infusion (BHI) broth, supplemented with 10 µg/ml each of hemin and NAD was inoculated with growth on chocolate plate. The starter culture was grown until the optical density (O.D.—600 nm) reached 0.6 and 0.08 and then the bacteria in the starter culture was used to inoculate six 500 ml flasks of supplemented BHI using 8 to 10 ml per flask. The bacteria were grown in 500 ml flasks for an additional 5 to 6 hours at which time the O.D. was 1.5 or greater. Cultures were centrifuged at 10,000 rpm for 10 minutes.

Bacterial pellets were resuspended in a total volume of 250 ml of an extraction solution comprising 0.5M NaCl, 0.01M $Na_2EDTA$, 0.01M Tris 50 µM 1,10-phenanthroline, pH 7.5. The cells were not sonicated or otherwise disrupted. The resuspended cells were allowed to sit on ice at 0° C. for 60 minutes. The resuspended cells were centrifuged at 10,000 rpm for 10 minutes at 4° C. to remove the majority of intact cells and cellular debris. The supernatant was collected and centrifuged at 100,000×g for 60 minutes at 4° C. The supernatant again was collected and dialyzed overnight at 4° C. against 0.01M sodium phosphate, pH 6.0.

The sample was centrifuged at 10,000 rpm for 10 minutes at 4° C. to remove insoluble debris precipitated from solution during dialysis. The supernatant was applied to a 10 ml CM Sepharose column which has been pre-equilibrated with 0.01M sodium phosphate, pH 6. Following application to this column, the column was washed with 0.01M sodium phosphate. Proteins were elevated from the column with a 0–0.5M KCl gradient in 0.01M Na phosphate, pH 6 and fractions were collected for gel examination. Coomassie gels of column fractions were carried out to identify those fractions containing high molecular weight proteins. The fractions containing high molecular weight proteins were pooled and concentrated to a 1 to 3 ml volume in preparation for application of sample to gel filtration column.

A Sepharose CL-4B gel filtration column was equilibrated with phosphate-buffered saline, pH 7.5. The concentrated high molecular weight protein sample was applied to the gel filtration column and column fractions were collected. Coomassie gels were performed on the column fractions to identify those containing high molecular weight proteins. The column fractions containing high molecular weight proteins were pooled.

The proteins were tested to determine whether they would protect against experimental otitis media cased by the homologous strain.

Chinchillas received three monthly subcutaneous injections with 40 µg of an HMW1–HMW2 protein mixture in Freund's adjuvant. One month after the last injection, the animals were challenged by intrabullar inoculation with 300 cfu MTHI strain 12.

Infection developed in 5 of 5 control animals versus 5 of 10 immunized animals. Among infected animals, geometric mean bacterial counts in middle ear fluid 7 days post-challenge were $7.4\times10^6$ in control animals verus $1.3\times10^5$ in immunized animals.

Serum antibody titres following immunization were comparable in uninfected and infected animals. However, infection in immunized animals was uniformly associated with the appearance of bacteria down-regulated in expression of the HMW proteins, suggesting bacterial selection in response to immunologic pressure.

Although this data shows that protection following immunization was not complete, this data suggests the HMW adhesin proteins are potentially important protective antigens which may comprise one component of a multi-component NTHI vaccine.

Example 7

A number of synthetic peptides were derived from HMW1. Antisera then was raised to these peptides. The anti-peptide antisera to peptide HMW1-P5 was shown to recognize HMW1. Peptide HMW1-P5 covers amino acids 1453 to 1481 of HMW1, has the sequence VDEVIEAKRILEKVKDLSDEEREALAKLG (SEQ ID NO:9), and represents bases 1498 to 1576 in FIG. 10.

This finding demonstrates that the DNA sequence and the derived protein is being interpreted in the correct reading frame and that peptides derived from the sequence can be produced which will be immunogenic.

SUMMARY OF DISCLOSURE

In summary of this disclosure, the present invention provides high molecular weight proteins of non-typeable Haemophilus, genes coding for the same and vaccines incorporating such proteins. Modifications are possible within the scope of this invention.

TABLE 1

Effect of mutation of high molecular weight proteins on adherence to Chang epithelial cells by nontypable *H. influenzae*.

| | ADHERENCE* | |
|---|---|---|
| Strain | % inoculum | relative to wild type† |
| Strain 12 derivatives | | |
| wild type | 87.7 ± 5.9 | 100.0 ± 6.7 |
| HMW1- mutant | 6.0 ± 0.9 | 6.8 ± 1.0 |
| HMW2- mutant | 89.9 ± 10.8 | 102.5 ± 12.3 |

TABLE 1-continued

Effect of mutation of high molecular weight proteins on adherence to Chang epithelial cells by nontypable *H. influenzae*.

| | ADHERENCE* | |
|---|---|---|
| Strain | % inoculum | relative to wild type† |
| HMW1-/HMW2- mutant | 2.0 ± 0.3 | 2.3 ± 0.3 |
| Strain 5 derivatives | | |
| wild type | 78.7 ± 3.2 | 100.0 ± 4.1 |
| HMW1-like mutant | 15.7 ± 2.6 | 19.9 ± 3.3 |
| HMW2-like mutant | 103.7 ± 14.0 | 131.7 ± 17.8 |
| double mutant | 3.5 ± 0.6 | 4.4 ± 0.8 |

*Numbers represent mean (± standard error of the mean) of mesurements in triplicate or quadruplicate from representative experiments.
†Adherence values for strain 12 derivatives are relative to strain 12 wild type; values for strain 5 derivatives are relative to strain 5 wild type.

TABLE 2

Adherence by *E. coli* DH5α and HB101 harboring hmw1 or hmw2 gene clusters.

| Strain* | Adherence relative to *H. influenzae* strain 12† |
|---|---|
| DH5α (pT7-7) | 0.7 ± 0.02 |
| DH5α (pHMW1-14) | 114.2 ± 15.9 |
| DH5α (pHMW2-21) | 14.0 ± 3.7 |
| HB101 (pT7-7) | 1.2 ± 0.5 |
| HB101 (pHMW1-14) | 93.6 ± 15.8 |
| HB101 (pHMW2-21) | 3.6 ± 0.9 |

*The plasmid pHMW1-14 contains the hmw1 gene cluster, while pHMW2-21 contains the hmw2 gene cluster; pT7-7 is the cloning vector used in these constructs.
†Numbers represent the mean (± standard error of the mean) of measurements made in triplicate from representative experiments.

What I claim is:

1. A conjugate comprising an isolated and purified high molecular weight protein of non-typeable *Haemophilus influenzae* which is selected from the group consisting of HMW1 encoded by the DNA sequence shown in FIG. 1 (SEQ ID no: 1) having the amino acid sequence shown in FIG. 2 (SEQ ID no:2) and having an apparent molecular weight of 125 kDa and HMW2 encoded by the DNA sequence shown in FIG. 3 (SEQ ID no: 3) having the derived amino acid sequence of FIG. 4 (SEQ ID n: 4) and having an apparent molecular weight of 120 kDa linked to an antigen, hapten or polysacharide for eliciting an immune response to said antigen, hapten or polysaccharide.

2. The conjugate as claimed in claim 1 wherein said polysaccharide is a protective polysaccharide against *Haemophilus influenzae* type b.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 5116 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
ACAGCGTTCT    CTTAATACTA    GTACAAACCC    ACAATAAAAT    ATGACAAACA    ACAATTACAA         6 0

CACCTTTTTT    GCAGTCTATA    TGCAAATATT    TTAAAAAATA    GTATAAATCC    GCCATATAAA        1 2 0

ATGGTATAAT    CTTTCATCTT    TCATCTTTCA    TCTTTCATCT    TTCATCTTTC    ATCTTTCATC        1 8 0

TTTCATCTTT    CATCTTTCAT    CTTTCATCTT    TCATCTTTCA    TCTTTCATCT    TTCATCTTTC        2 4 0

ACATGCCCTG    ATGAACCGAG    GGAAGGGAGG    GAGGGGCAAG    AATGAAGAGG    GAGCTGAACG        3 0 0

AACGCAAATG    ATAAAGTAAT    TTAATTGTTC    AACTAACCTT    AGGAGAAAAT    ATGAACAAGC        3 6 0
```

```
TATATCGTCT CAAATTCAGC AAACGCCTGA ATGCTTTGGT TGCTGTGTCT GAATTGGCAC      420
GGGGTTGTGA CCATTCCACA GAAAAAGGCA GCGAAAAACC TGCTCGCATG AAAGTGCGTC      480
ACTTAGCGTT AAAGCCACTT TCCGCTATGT TACTATCTTT AGGTGTAACA TCTATTCCAC      540
AATCTGTTTT AGCAAGCGGC TTACAAGGAA TGGATGTAGT ACACGGCACA GCCACTATGC      600
AAGTAGATGG TAATAAAACC ATTATCCGCA ACAGTGTTGA CGATATCATT AATTGGAAAC      660
AATTTAACAT CGACCAAAAT GAAATGGTGC AGTTTTTACA AGAAACAAC AACTCCGCCG       720
TATTCAACCG TGTTACATCT AACCAAATCT CCCAATTAAA AGGGATTTTA GATTCTAACG      780
GACAAGTCTT TTTAATCAAC CCAAATGGTA TCACAATAGG TAAAGACGCA ATTATTAACA      840
CTAATGGCTT TACGGCTTCT ACGCTAGACA TTTCTAACGA AAACATCAAG GCGCGTAATT     900
TCACCTTCGA GCAAACCAAA GATAAAGCGC TCGCTGAAAT TGTGAATCAC GGTTTAATTA      960
CTGTCGGTAA AGACGGCAGT GTAAATCTTA TTGGTGGCAA AGTGAAAAAC GAGGGTGTGA     1020
TTAGCGTAAA TGGTGGCAGC ATTTCTTTAC TCGCAGGGCA AAAAATCACC ATCAGCGATA     1080
TAATAAACCC AACCATTACT TACAGCATTG CCGCGCCTGA AAATGAAGCG GTCAATCTGG     1140
GCGATATTTT TGCCAAAGGC GGTAACATTA ATGTCCGTGC TGCCACTATT CGAAACCAAG     1200
GTAAACTTTC TGCTGATTCT GTAAGCAAAG ATAAAGCGG CAATATTGTT CTTTCCGCCA      1260
AAGAGGGTGA AGCGGAAATT GGCGGTGTAA TTTCCGCTCA AAATCAGCAA GCTAAAGGCG     1320
GCAAGCTGAT GATTACAGGC GATAAAGTCA CATTAAAAAC AGGTGCAGTT ATCGACCTTT     1380
CAGGTAAAGA AGGGGGAGAA ACTTACCTTG GCGGTGACGA GCGCGGCGAA GGTAAAAAGG     1440
GCATTCAATT AGCAAAGAAA ACCTCTTTAG AAAAAGGCTC AACCATCAAT GTATCAGGCA     1500
AAGAAAAAGG CGGACGCGCT ATTGTGTGGG GCGATATTGC GTTAATTGAC GGCAATATTA     1560
ACGCTCAAGG TAGTGGTGAT ATCGCTAAAA CCGGTGGTTT TGTGGAGACG TCGGGGCATG     1620
ATTTATTCAT CAAAGACAAT GCAATTGTTG ACGCCAAAGA GTGGTTGTTA GACCCGGATA     1680
ATGTATCTAT TAATGCAGAA ACAGCAGGAC GCAGCAATAC TTCAGAAGAC GATGAATACA     1740
CGGGATCCGG GAATAGTGCC AGCACCCCAA AACGAAACAA AGAAAGACA ACATTAACAA      1800
ACACAACTCT TGAGAGTATA CTAAAAAAAG GTACCTTTGT TAACATCACT GCTAATCAAC     1860
GCATCTATGT CAATAGCTCC ATTAATTTAT CCAATGGCAG CTTAACTCTT TGGAGTGAGG     1920
GTCGGAGCGG TGGCGGCGTT GAGATTAACA ACGATATTAC CACCGGTGAT GATACCAGAG     1980
GTGCAAACTT AACAATTTAC TCAGGCGGCT GGGTTGATGT TCATAAAAAT ATCTCACTCG     2040
GGGCGCAAGG TAACATAAAC ATTACAGCTA AACAAGATAT CGCCTTTGAG AAAGGAAGCA     2100
ACCAAGTCAT TACAGGTCAA GGGACTATTA CCTCAGGCAA TCAAAAAGGT TTTAGATTTA     2160
ATAATGTCTC TCTAAACGGC ACTGGCAGCG GACTGCAATT CACCACTAAA AGAACCAATA    2220
AATACGCTAT CACAAATAAA TTTGAAGGGA CTTAAATAT TTCAGGGAAA GTGAACATCT      2280
CAATGGTTTT ACCTAAAAAT GAAAGTGGAT ATGATAAATT CAAAGGACGC ACTTACTGGA     2340
ATTTAACCTC CTTAAATGTT TCCGAGAGTG GCGAGTTTAA CCTCACTATT GACTCCAGAG     2400
GAAGCGATAG TGCAGGCACA CTTACCCAGC CTTATAATTT AAACGGTATA TCATTCAACA     2460
AAGACACTAC CTTTAATGTT GAACGAAATG CAAGAGTCAA CTTTGACATC AAGGCACCAA     2520
TAGGGATAAA TAAGTATTCT AGTTTGAATT ACGCATCATT TAATGGAAAC ATTTCAGTTT     2580
CGGGAGGGGG GAGTGTTGAT TTCACACTTC TCGCCTCATC CTCTAACGTC CAAACCCCCG     2640
GTGTAGTTAT AAATTCTAAA TACTTTAATG TTTCAACAGG GTCAAGTTTA AGATTTAAAA     2700
CTTCAGGCTC AACAAAAACT GGCTTCTCAA TAGAGAAAGA TTTAACTTTA AATGCCACCG     2760
```

| | | | | | | |
|---|---|---|---|---|---|---|
| GAGGCAACAT | AACACTTTTG | CAAGTTGAAG | GCACCGATGG | AATGATTGGT | AAAGGCATTG | 2820 |
| TAGCCAAAAA | AAACATAACC | TTTGAAGGAG | GTAACATCAC | CTTTGGCTCC | AGGAAAGCCG | 2880 |
| TAACAGAAAT | CGAAGGCAAT | GTTACTATCA | ATAACAACGC | TAACGTCACT | CTTATCGGTT | 2940 |
| CGGATTTTGA | CAACCATCAA | AAACCTTTAA | CTATTAAAAA | AGATGTCATC | ATTAATAGCG | 3000 |
| GCAACCTTAC | CGCTGGAGGC | AATATTGTCA | ATATAGCCGG | AAATCTTACC | GTTGAAAGTA | 3060 |
| ACGCTAATTT | CAAAGCTATC | ACAAATTTCA | CTTTTAATGT | AGGCGGCTTG | TTTGACAACA | 3120 |
| AAGGCAATTC | AAATATTTCC | ATTGCCAAAG | GAGGGCTCG | CTTTAAAGAC | ATTGATAATT | 3180 |
| CCAAGAATTT | AAGCATCACC | ACCAACTCCA | GCTCCACTTA | CCGCACTATT | ATAAGCGGCA | 3240 |
| ATATAACCAA | TAAAACGGT | GATTTAAATA | TTACGAACGA | AGGTAGTGAT | ACTGAAATGC | 3300 |
| AAATTGGCGG | CGATGTCTCG | CAAAAGAAG | GTAATCTCAC | GATTTCTTCT | GACAAAATCA | 3360 |
| ATATTACCAA | ACAGATAACA | ATCAAGGCAG | GTGTTGATGG | GGAGAATTCC | GATTCAGACG | 3420 |
| CGACAAACAA | TGCCAATCTA | ACCATTAAAA | CCAAGAATT | GAAATTAACG | CAAGACCTAA | 3480 |
| ATATTTCAGG | TTTCAATAAA | GCAGAGATTA | CAGCTAAAGA | TGGTAGTGAT | TTAACTATTG | 3540 |
| GTAACACCAA | TAGTGCTGAT | GGTACTAATG | CCAAAAAGT | AACCTTTAAC | CAGGTTAAAG | 3600 |
| ATTCAAAAAT | CTCTGCTGAC | GGTCACAAGG | TGACACTACA | CAGCAAAGTG | GAAACATCCG | 3660 |
| GTAGTAATAA | CAACACTGAA | GATAGCAGTG | ACAATAATGC | CGGCTTAACT | ATCGATGCAA | 3720 |
| AAAATGTAAC | AGTAAACAAC | AATATTACTT | CTCACAAAGC | AGTGAGCATC | TCTGCGACAA | 3780 |
| GTGGAGAAAT | TACCACTAAA | ACAGGTACAA | CCATTAACGC | AACCACTGGT | AACGTGGAGA | 3840 |
| TAACCGCTCA | AACAGGTAGT | ATCCTAGGTG | GAATTGAGTC | CAGCTCTGGC | TCTGTAACAC | 3900 |
| TTACTGCAAC | CGAGGGCGCT | CTTGCTGTAA | GCAATATTTC | GGGCAACACC | GTTACTGTTA | 3960 |
| CTGCAAATAG | CGGTGCATTA | ACCACTTTGG | CAGGCTCTAC | AATTAAAGGA | ACCGAGAGTG | 4020 |
| TAACCACTTC | AAGTCAATCA | GGCGATATCG | GCGGTACGAT | TTCTGGTGGC | ACAGTAGAGG | 4080 |
| TTAAAGCAAC | CGAAAGTTTA | ACCACTCAAT | CCAATTCAAA | AATTAAAGCA | ACAACAGGCG | 4140 |
| AGGCTAACGT | AACAAGTGCA | ACAGGTACAA | TTGGTGGTAC | GATTTCCGGT | AATACGGTAA | 4200 |
| ATGTTACGGC | AAACGCTGGC | GATTAACAG | TTGGGAATGG | CGCAGAAATT | AATGCGACAG | 4260 |
| AAGGAGCTGC | AACCTTAACT | ACATCATCGG | GCAAATTAAC | TACCGAAGCT | AGTTCACACA | 4320 |
| TTACTTCAGC | CAAGGGTCAG | GTAAATCTTT | CAGCTCAGGA | TGGTAGCGTT | GCAGGAAGTA | 4380 |
| TTAATGCCGC | CAATGTGACA | CTAAATACTA | CAGGCACTTT | AACTACCGTG | AAGGGTTCAA | 4440 |
| ACATTAATGC | AACCAGCGGT | ACCTTGGTTA | TTAACGCAAA | AGACGCTGAG | CTAAATGGCG | 4500 |
| CAGCATTGGG | TAACCACACA | GTGGTAAATG | CAACCAACGC | AAATGGCTCC | GGCAGCGTAA | 4560 |
| TCGCGACAAC | CTCAAGCAGA | GTGAACATCA | CTGGGGATTT | AATCACAATA | AATGGATTAA | 4620 |
| ATATCATTTC | AAAAAACGGT | ATAAACACCG | TACTGTTAAA | AGGCGTTAAA | ATTGATGTGA | 4680 |
| AATACATTCA | ACCGGGTATA | GCAAGCGTAG | ATGAAGTAAT | TGAAGCGAAA | CGCATCCTTG | 4740 |
| AGAAGGTAAA | AGATTTATCT | GATGAAGAAA | GAGAAGCGTT | AGCTAAACTT | GGAGTAAGTG | 4800 |
| CTGTACGTTT | TATTGAGCCA | AATAATACAA | TTACAGTCGA | TACACAAAAT | GAATTTGCAA | 4860 |
| CCAGACCATT | AAGTCGAATA | GTGATTTCTG | AAGGCAGGGC | GTGTTTCTCA | AACAGTGATG | 4920 |
| GCGCGACGGT | GTGCGTTAAT | ATCGCTGATA | ACGGGCGGTA | GCGGTCAGTA | ATTGACAAGG | 4980 |
| TAGATTTCAT | CCTGCAATGA | AGTCATTTTA | TTTTCGTATT | ATTTACTGTG | TGGGTTAAAG | 5040 |
| TTCAGTACGG | GCTTTACCCA | TCTTGTAAAA | AATTACGGAG | AATACAATAA | AGTATTTTA | 5100 |
| ACAGGTTATT | ATTATG | | | | | 5116 |

(2) INFORMATION FOR SEQ ID NO:2:

(i) SEQUENCE CHARACTERISTICS:
        (A) LENGTH: 1536 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

```
Met Asn Lys Ile Tyr Arg Leu Lys Phe Ser Lys Arg Leu Asn Ala Leu
  1               5                  10                  15

Val Ala Val Ser Glu Leu Ala Arg Gly Cys Asp His Ser Thr Glu Lys
             20                  25                  30

Gly Ser Glu Lys Pro Ala Arg Met Lys Val Arg His Leu Ala Leu Lys
         35                  40                  45

Pro Leu Ser Ala Met Leu Leu Ser Leu Gly Val Thr Ser Ile Pro Gln
         50                  55                  60

Ser Val Leu Ala Ser Gly Leu Gln Gly Met Asp Val Val His Gly Thr
 65                  70                  75                  80

Ala Thr Met Gln Val Asp Gly Asn Lys Thr Ile Ile Arg Asn Ser Val
                 85                  90                  95

Asp Ala Ile Ile Asn Trp Lys Gln Phe Asn Ile Asp Gln Asn Glu Met
                100                 105                 110

Val Gln Phe Leu Gln Glu Asn Asn Ser Ala Val Phe Asn Arg Val
                115                 120                 125

Thr Ser Asn Gln Ile Ser Gln Leu Lys Gly Ile Leu Asp Ser Asn Gly
        130                 135                 140

Gln Val Phe Leu Ile Asn Pro Asn Gly Ile Thr Ile Gly Lys Asp Ala
145                 150                 155                 160

Ile Ile Asn Thr Asn Gly Phe Thr Ala Ser Thr Leu Asp Ile Ser Asn
                165                 170                 175

Glu Asn Ile Lys Ala Arg Asn Phe Thr Phe Glu Gln Thr Lys Asp Lys
                180                 185                 190

Ala Leu Ala Glu Ile Val Asn His Gly Leu Ile Thr Val Gly Lys Asp
            195                 200                 205

Gly Ser Val Asn Leu Ile Gly Gly Lys Val Lys Asn Glu Gly Val Ile
    210                 215                 220

Ser Val Asn Gly Gly Ser Ile Ser Leu Leu Ala Gly Gln Lys Ile Thr
225                 230                 235                 240

Ile Ser Asp Ile Ile Asn Pro Thr Ile Thr Tyr Ser Ile Ala Ala Pro
                245                 250                 255

Glu Asn Glu Ala Val Asn Leu Gly Asp Ile Phe Ala Lys Gly Gly Asn
            260                 265                 270

Ile Asn Val Arg Ala Ala Thr Ile Arg Asn Gln Gly Lys Leu Ser Ala
        275                 280                 285

Asp Ser Val Ser Lys Asp Lys Ser Gly Asn Ile Val Leu Ser Ala Lys
    290                 295                 300

Glu Gly Glu Ala Glu Ile Gly Gly Val Ile Ser Ala Gln Asn Gln Gln
305                 310                 315                 320

Ala Lys Gly Gly Lys Leu Met Ile Thr Gly Asp Lys Val Thr Leu Lys
                325                 330                 335

Thr Gly Ala Val Ile Asp Leu Ser Gly Lys Glu Gly Gly Glu Thr Tyr
            340                 345                 350

Leu Gly Gly Asp Glu Arg Gly Glu Gly Lys Asn Gly Ile Gln Leu Ala
```

-continued

|     |     | 355 |     |     |     | 360 |     |     |     | 365 |     |     |     |     |
| --- | --- | --- | --- | --- | --- | --- | --- | --- | --- | --- | --- | --- | --- | --- |
| Lys | Lys 370 | Thr | Ser | Leu | Glu | Lys 375 | Gly | Ser | Thr | Ile | Asn 380 | Val | Ser | Gly | Lys |
| Glu 385 | Lys | Gly | Gly | Arg | Ala 390 | Ile | Val | Trp | Gly | Asp 395 | Ile | Ala | Leu | Ile | Asp 400 |
| Gly | Asn | Ile | Asn | Ala 405 | Gln | Gly | Ser | Gly | Asp 410 | Ile | Ala | Lys | Thr | Gly 415 | Gly |
| Phe | Val | Glu | Thr 420 | Ser | Gly | His | Asp | Leu 425 | Phe | Ile | Lys | Asp | Asn 430 | Ala | Ile |
| Val | Asp | Ala 435 | Lys | Glu | Trp | Leu | Leu 440 | Asp | Phe | Asp | Asn | Val 445 | Ser | Ile | Asn |
| Ala | Glu 450 | Thr | Ala | Gly | Arg | Ser 455 | Asn | Thr | Ser | Glu | Asp 460 | Asp | Glu | Tyr | Thr |
| Gly 465 | Ser | Gly | Asn | Ser | Ala 470 | Ser | Thr | Pro | Lys | Arg 475 | Asn | Lys | Glu | Lys | Thr 480 |
| Thr | Leu | Thr | Asn | Thr 485 | Thr | Leu | Glu | Ser | Ile 490 | Leu | Lys | Lys | Gly | Thr 495 | Phe |
| Val | Asn | Ile | Thr 500 | Ala | Asn | Gln | Arg | Ile 505 | Tyr | Val | Asn | Ser | Ser 510 | Ile | Asn |
| Leu | Ser | Asn 515 | Gly | Ser | Leu | Thr | Leu 520 | Trp | Ser | Glu | Gly | Arg 525 | Ser | Gly | Gly |
| Gly | Val 530 | Glu | Ile | Asn | Asn | Asp 535 | Ile | Thr | Thr | Gly | Asp 540 | Asp | Thr | Arg | Gly |
| Ala 545 | Asn | Leu | Thr | Ile | Tyr 550 | Ser | Gly | Gly | Trp | Val 555 | Asp | Val | His | Lys | Asn 560 |
| Ile | Ser | Leu | Gly | Ala 565 | Gln | Gly | Asn | Ile | Asn 570 | Ile | Thr | Ala | Lys | Gln 575 | Asp |
| Ile | Ala | Phe | Glu 580 | Lys | Gly | Ser | Asn | Gln 585 | Val | Ile | Thr | Gly | Gln 590 | Gly | Thr |
| Ile | Thr | Ser 595 | Gly | Asn | Gln | Lys | Gly 600 | Phe | Arg | Phe | Asn | Asn 605 | Val | Ser | Leu |
| Asn | Gly 610 | Thr | Gly | Ser | Gly | Leu 615 | Gln | Phe | Thr | Thr | Lys 620 | Arg | Thr | Asn | Lys |
| Tyr 625 | Ala | Ile | Thr | Asn | Lys 630 | Phe | Glu | Gly | Thr | Leu 635 | Asn | Ile | Ser | Gly | Lys 640 |
| Val | Asn | Ile | Ser | Met 645 | Val | Leu | Pro | Lys | Asn 650 | Glu | Ser | Gly | Tyr | Asp 655 | Lys |
| Phe | Lys | Gly | Arg 660 | Thr | Tyr | Trp | Asn | Leu 665 | Thr | Ser | Leu | Asn | Val 670 | Ser | Glu |
| Ser | Gly | Glu 675 | Phe | Asn | Leu | Thr | Ile 680 | Asp | Ser | Arg | Gly | Ser 685 | Asp | Ser | Ala |
| Gly | Thr 690 | Leu | Thr | Gln | Pro | Tyr 695 | Asn | Leu | Asn | Gly | Ile 700 | Ser | Phe | Asn | Lys |
| Asp 705 | Thr | Thr | Phe | Asn | Val 710 | Glu | Arg | Asn | Ala | Arg 715 | Val | Asn | Phe | Asp | Ile 720 |
| Lys | Ala | Pro | Ile | Gly 725 | Ile | Asn | Lys | Tyr | Ser 730 | Ser | Leu | Asn | Tyr | Ala 735 | Ser |
| Phe | Asn | Gly | Asn 740 | Ile | Ser | Val | Ser | Gly 745 | Gly | Gly | Ser | Val | Asp 750 | Phe | Thr |
| Leu | Leu | Ala 755 | Ser | Ser | Ser | Asn | Val 760 | Gln | Thr | Pro | Gly | Val 765 | Val | Ile | Asn |
| Ser | Lys 770 | Tyr | Phe | Asn | Val | Ser 775 | Thr | Gly | Ser | Ser | Leu 780 | Arg | Phe | Lys | Thr |

-continued

```
Ser Gly Ser Thr Lys Thr Gly Phe Ser Ile Glu Lys Asp Leu Thr Leu
785                 790                 795                 800

Asn Ala Thr Gly Gly Asn Ile Thr Leu Leu Gln Val Glu Gly Thr Asp
                805                 810                 815

Gly Met Ile Gly Lys Gly Ile Val Ala Lys Lys Asn Ile Thr Phe Glu
            820                 825                 830

Gly Gly Asn Ile Thr Phe Gly Ser Arg Lys Ala Val Thr Glu Ile Glu
            835                 840                 845

Gly Asn Val Thr Ile Asn Asn Ala Asn Val Thr Leu Ile Gly Ser
        850                 855                 860

Asp Phe Asp Asn His Gln Lys Pro Leu Thr Ile Lys Lys Asp Val Ile
865                 870                 875                 880

Ile Asn Ser Gly Asn Leu Thr Ala Gly Gly Asn Ile Val Asn Ile Ala
                885                 890                 895

Gly Asn Leu Thr Val Glu Ser Asn Ala Asn Phe Lys Ala Ile Thr Asn
            900                 905                 910

Phe Thr Phe Asn Val Gly Gly Leu Phe Asp Asn Lys Gly Asn Ser Asn
            915                 920                 925

Ile Ser Ile Ala Lys Gly Gly Ala Arg Phe Lys Asp Ile Asp Asn Ser
    930                 935                 940

Lys Asn Leu Ser Ile Thr Thr Asn Ser Ser Ser Thr Tyr Arg Thr Ile
945                 950                 955                 960

Ile Ser Gly Asn Ile Thr Asn Lys Asn Gly Asp Leu Asn Ile Thr Asn
                965                 970                 975

Glu Gly Ser Asp Thr Glu Met Gln Ile Gly Gly Asp Val Ser Gln Lys
            980                 985                 990

Glu Gly Asn Leu Thr Ile Ser Ser Asp Lys Ile Asn Ile Thr Lys Gln
            995                 1000                1005

Ile Thr Ile Lys Ala Gly Val Asp Gly Glu Asn Ser Asp Ser Asp Ala
    1010                1015                1020

Thr Asn Asn Ala Asn Leu Thr Ile Lys Thr Lys Glu Leu Lys Leu Thr
1025                1030                1035                1040

Gln Asp Leu Asn Ile Ser Gly Phe Asn Lys Ala Glu Ile Thr Ala Lys
                1045                1050                1055

Asp Gly Ser Asp Leu Thr Ile Gly Asn Thr Asn Ser Ala Asp Gly Thr
            1060                1065                1070

Asn Ala Lys Lys Val Thr Phe Asn Gln Val Lys Asp Ser Lys Ile Ser
            1075                1080                1085

Ala Asp Gly His Lys Val Thr Leu His Ser Lys Val Glu Thr Ser Gly
    1090                1095                1100

Ser Asn Asn Asn Thr Glu Asp Ser Ser Asp Asn Ala Gly Leu Thr
1105                1110                1115                1120

Ile Asp Ala Lys Asn Val Thr Val Asn Asn Asn Ile Thr Ser His Lys
                1125                1130                1135

Ala Val Ser Ile Ser Ala Thr Ser Gly Glu Ile Thr Thr Lys Thr Gly
            1140                1145                1150

Thr Thr Ile Asn Ala Thr Thr Gly Asn Val Glu Ile Thr Ala Gln Thr
            1155                1160                1165

Gly Ser Ile Leu Gly Gly Ile Glu Ser Ser Ser Gly Ser Val Thr Leu
            1170                1175                1180

Thr Ala Thr Glu Gly Ala Leu Ala Val Ser Asn Ile Ser Gly Asn Thr
1185                1190                1195                1200

Val Thr Val Thr Ala Asn Ser Gly Ala Leu Thr Thr Leu Ala Gly Ser
            1205                1210                1215
```

| | | | | | | | | | | | | | | |
|---|---|---|---|---|---|---|---|---|---|---|---|---|---|---|
|Thr|Ile|Lys|Gly|Thr|Glu|Ser|Val|Thr|Thr|Ser|Ser|Gln|Ser|Gly|Asp|
| | | |1220| | | |1225| | | |1230| | | |
|Ile|Gly|Gly|Thr|Ile|Ser|Gly|Gly|Thr|Val|Glu|Val|Lys|Ala|Thr|Glu|
| | |1235| | | |1240| | | |1245| | | | |
|Ser|Leu|Thr|Thr|Gln|Ser|Asn|Ser|Lys|Ile|Lys|Ala|Thr|Thr|Gly|Glu|
| |1250| | | |1255| | | |1260| | | | | |
|Ala|Asn|Val|Thr|Ser|Ala|Thr|Gly|Thr|Ile|Gly|Gly|Thr|Ile|Ser|Gly|
|1265| | | |1270| | | |1275| | | | | |1280|
|Asn|Thr|Val|Asn|Val|Thr|Ala|Asn|Ala|Gly|Asp|Leu|Thr|Val|Gly|Asn|
| | | |1285| | | |1290| | | |1295| | | |
|Gly|Ala|Glu|Ile|Asn|Ala|Thr|Glu|Gly|Ala|Ala|Thr|Leu|Thr|Thr|Ser|
| | |1300| | | |1305| | | |1310| | | | |
|Ser|Gly|Lys|Leu|Thr|Thr|Glu|Ala|Ser|Ser|His|Ile|Thr|Ser|Ala|Lys|
| |1315| | | |1320| | | |1325| | | | | |
|Gly|Gln|Val|Asn|Leu|Ser|Ala|Gln|Asp|Gly|Ser|Val|Ala|Gly|Ser|Ile|
| |1330| | | |1335| | | |1340| | | | | |
|Asn|Ala|Ala|Asn|Val|Thr|Leu|Asn|Thr|Thr|Gly|Thr|Leu|Thr|Thr|Val|
|1345| | | |1350| | | |1355| | | | | |1360|
|Lys|Gly|Ser|Asn|Ile|Asn|Ala|Thr|Ser|Gly|Thr|Leu|Val|Ile|Asn|Ala|
| | | |1365| | | |1370| | | | | |1375| |
|Lys|Asp|Ala|Glu|Leu|Asn|Gly|Ala|Ala|Leu|Gly|Asn|His|Thr|Val|Val|
| | |1380| | | |1385| | | |1390| | | | |
|Asn|Ala|Thr|Asn|Ala|Asn|Gly|Ser|Gly|Ser|Val|Ile|Ala|Thr|Thr|Ser|
| |1395| | | |1400| | | |1405| | | | | |
|Ser|Arg|Val|Asn|Ile|Thr|Gly|Asp|Leu|Ile|Thr|Ile|Asn|Gly|Leu|Asn|
| |1410| | | |1415| | | |1420| | | | | |
|Ile|Ile|Ser|Lys|Asn|Gly|Ile|Asn|Thr|Val|Leu|Leu|Lys|Gly|Val|Lys|
|1425| | | |1430| | | |1435| | | | | |1440|
|Ile|Asp|Val|Lys|Tyr|Ile|Gln|Pro|Gly|Ile|Ala|Ser|Val|Asp|Glu|Val|
| | | |1445| | | |1450| | | |1455| | | |
|Ile|Glu|Ala|Lys|Arg|Ile|Leu|Glu|Lys|Val|Lys|Asp|Leu|Ser|Asp|Glu|
| | |1460| | | |1465| | | |1470| | | | |
|Glu|Arg|Glu|Ala|Leu|Ala|Lys|Leu|Gly|Val|Ser|Ala|Val|Arg|Phe|Ile|
| |1475| | | |1480| | | |1485| | | | | |
|Glu|Pro|Asn|Asn|Thr|Ile|Thr|Val|Asp|Thr|Gln|Asn|Glu|Phe|Ala|Thr|
| |1490| | | |1495| | | |1500| | | | | |
|Arg|Pro|Leu|Ser|Arg|Ile|Val|Ile|Ser|Glu|Gly|Arg|Ala|Cys|Phe|Ser|
|1505| | | |1510| | | |1515| | | | | |1520|
|Asn|Ser|Asp|Gly|Ala|Thr|Val|Cys|Val|Asn|Ile|Ala|Asp|Asn|Gly|Arg|
| | | |1525| | | |1530| | | |1535| | | |

( 2 ) INFORMATION FOR SEQ ID NO:3:

( i ) SEQUENCE CHARACTERISTICS:
        ( A ) LENGTH: 4937 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

```
TAAATATACA  AGATAATAAA  AATAAATCAA  GATTTTTGTG  ATGACAAACA  ACAATTACAA        60
CACCTTTTTT  GCAGTCTATA  TGCAAATATT  TTAAAAAAAT  AGTATAAATC  CGCCATATAA       120
AATGGTATAA  TCTTTCATCT  TTCATCTTTA  ATCTTTCATC  TTTCATCTTT  CATCTTTCAT       180
```

| | | | | | | |
|---|---|---|---|---|---|---|
| CTTTCATCTT | TCATCTTTCA | TCTTTCATCT | TTCATCTTTC | ATCTTTCATC | TTTCATCTTT | 240 |
| CACATGAAAT | GATGAACCGA | GGGAAGGGAG | GGAGGGGCAA | GAATGAAGAG | GGAGCTGAAC | 300 |
| GAACGCAAAT | GATAAAGTAA | TTTAATTGTT | CAACTAACCT | TAGGAGAAAA | TATGAACAAG | 360 |
| ATATATCGTC | TCAAATTCAG | CAAACGCCTG | AATGCTTTGG | TTGCTGTGTC | TGAATTGGCA | 420 |
| CGGGGTTGTG | ACCATTCCAC | AGAAAAGGC | TTCCGCTATG | TTACTATCTT | TAGGTGTAAC | 480 |
| CACTTAGCGT | TAAAGCCACT | TTCCGCTATG | TTACTATCTT | TAGGTGTAAC | ATCTATTCCA | 540 |
| CAATCTGTTT | TAGCAAGCGG | CTTACAAGGA | ATGGATGTAG | TACACGGCAC | AGCCACTATG | 600 |
| CAAGTAGATG | GTAATAAAAC | CATTATCCGC | AACAGTGTTG | ACGCTATCAT | TAATTGGAAA | 660 |
| CAATTTAACA | TCGACCAAAA | TGAAATGGTG | CAGTTTTTAC | AAGAAAACAA | CAACTCCGCC | 720 |
| GTATTCAACC | GTGTTACATC | TAACCAAATC | TCCCAATTAA | AAGGGATTTT | AGATTCTAAC | 780 |
| GGACAAGTCT | TTTTAATCAA | CCCAAATGGT | ATCACAATAG | GTAAAGACGC | AATTATTAAC | 840 |
| ACTAATGGCT | TTACGGCTTC | TACGCTAGAC | ATTTCTAACG | AAAACATCAA | GGCGCGTAAT | 900 |
| TTCACCTTCG | AGCAAACCAA | AGATAAAGCG | CTCGCTGAAA | TTGTGAATCA | CGGTTTAATT | 960 |
| ACTGTCGGTA | AAGACGGCAG | TGTAAATCTT | ATTGGTGGCA | AAGTGAAAAA | CGAGGGTGTG | 1020 |
| ATTAGCGTAA | ATGGTGGCAG | CATTTCTTTA | CTCGCAGGGC | AAAAAATCAC | CATCAGCGAT | 1080 |
| ATAATAAACC | CAACCATTAC | TTACAGCATT | GCCGCGCCTG | AAAATGAAGC | GGTCAATCTG | 1140 |
| GGCGATATTT | TTGCCAAAGG | CGGTAACATT | AATGTCCGTG | CTGCCACTAT | TCGAAACCAA | 1200 |
| GGTAAACTTT | CTGCTGATTC | TGTAAGCAAA | GATAAAGCG | GCAATATTGT | TCTTTCCGCC | 1260 |
| AAAGAGGGTG | AAGCGGAAAT | TGGCGGTGTA | ATTTCCGCTC | AAAATCAGCA | AGCTAAAGGC | 1320 |
| GGCAAGCTGA | TGATTACAGG | CGATAAAGTC | ACATTAAAAA | CAGGTGCAGT | TATCGACCTT | 1380 |
| TCAGGTAAAG | AAGGGGGAGA | AACTTACCTT | GGCGGTGACG | AGCGCGGCGA | AGGTAAAAAC | 1440 |
| GGCATTCAAT | TAGCAAAGAA | AACCTCTTTA | GAAAAAGGCT | CAACCATCAA | TGTATCAGGC | 1500 |
| AAAGAAAAAG | GCGGACGCGC | TATTGTGTGG | GGCGATATTG | CGTTAATTGA | CGGCAATATT | 1560 |
| AACGCTCAAG | GTAGTGGTGA | TATCGCTAAA | ACCGGTGGTT | TTGTGGAGAC | ATCGGGGCAT | 1620 |
| TATTTATCCA | TTGACAGCAA | TGCAATTGTT | AAAACAAAAG | AGTGGTTGCT | AGACCCTGAT | 1680 |
| GATGTAACAA | TTGAAGCCGA | AGACCCCCTT | CGCAATAATA | CCGGTATAAA | TGATGAATTC | 1740 |
| CCAACAGGCA | CCGGTGAAGC | AAGCGACCCT | AAAAAAAATA | GCGAACTCAA | AACAACGCTA | 1800 |
| ACCAATACAA | CTATTTCAAA | TTATCTGAAA | AACGCCTGGA | CAATGAATAT | AACGGCATCA | 1860 |
| AGAAAACTTA | CCGTTAATAG | CTCAATCAAC | ATCGGAAGCA | ACTCCCACTT | AATTCTCCAT | 1920 |
| AGTAAAGGTC | AGCGTGGCGG | AGGCGTTCAG | ATTGATGGAG | ATATTACTTC | TAAAGGCGGA | 1980 |
| AATTTAACCA | TTTATTCTGG | CGGATGGGTT | GATGTTCATA | AAAATATTAC | GCTTGATCAG | 2040 |
| GGTTTTTTAA | ATATTACCGC | CGCTTCCGTA | GCTTTTGAAG | GTGGAAATAA | CAAAGCACGC | 2100 |
| GACGCGGCAA | ATGCTAAAAT | TGTCGCCCAG | GGCACTGTAA | CCATTACAGG | AGAGGGAAAA | 2160 |
| GATTTCAGGG | CTAACAACGT | ATCTTTAAAC | GGAACGGGTA | AAGGTCTGAA | TATCATTTCA | 2220 |
| TCAGTGAATA | ATTTAACCCA | CAATCTTAGT | GGCACAATTA | ACATATCTGG | GAATATAACA | 2280 |
| ATTAACCAAA | CTACGAGAAA | GAACACCTCG | TATTGGCAAA | CCAGCCATGA | TTCGCACTGG | 2340 |
| AACGTCAGTG | CTCTTAATCT | AGAGACAGGC | GCAAATTTTA | CCTTTATTAA | ATACATTTCA | 2400 |
| AGCAATAGCA | AAGGCTTAAC | AACACAGTAT | AGAAGCTCTG | CAGGGGTGAA | TTTTAACGGC | 2460 |
| GTAAATGGCA | ACATGTCATT | CAATCTCAAA | GAAGGAGCGA | AAGTTAATTT | CAAATTAAAA | 2520 |
| CCAAACGAGA | ACATGAACAC | AAGCAAACCT | TTACCAATTC | GGTTTTTAGC | CAATATCACA | 2580 |

| | | | | | | |
|---|---|---|---|---|---|---|
| GCCACTGGTG | GGGGCTCTGT | TTTTTTTGAT | ATATATGCCA | ACCATTCTGG | CAGAGGGGCT | 2640 |
| GAGTTAAAAA | TGAGTGAAAT | TAATATCTCT | AACGGCGCTA | ATTTTACCTT | AAATTCCCAT | 2700 |
| GTTCGCGGCG | ATGACGCTTT | TAAAATCAAC | AAAGACTTAA | CCATAAATGC | AACCAATTCA | 2760 |
| AATTTCAGCC | TCAGACAGAC | GAAAGATGAT | TTTTATGACG | GGTACGCACG | CAATGCCATC | 2820 |
| AATTCAACCT | ACAACATATC | CATTCTGGGC | GGTAATGTCA | CCCTTGGTGG | ACAAAACTCA | 2880 |
| AGCAGCAGCA | TTACGGGGAA | TATTACTATC | GAGAAAGCAG | CAAATGTTAC | GCTAGAAGCC | 2940 |
| AATAACGCCC | CTAATCAGCA | AAACATAAGG | GATAGAGTTA | TAAAACTTGG | CAGCTTGCTC | 3000 |
| GTTAATGGGA | GTTTAAGTTT | AACTGGCGAA | AATGCAGATA | TTAAAGGCAA | TCTCACTATT | 3060 |
| TCAGAAAGCG | CCACTTTTAA | AGGAAAGACT | AGAGATACCC | TAAATATCAC | CGGCAATTTT | 3120 |
| ACCAATAATG | GCACTGCCGA | AATTAATATA | ACACAAGGAG | TGGTAAAACT | TGGCAATGTT | 3180 |
| ACCAATGATG | GTGATTTAAA | CATTACCACT | CACGCTAAAC | GCAACCAAAG | AAGCATCATC | 3240 |
| GGCGGAGATA | TAATCAACAA | AAAAGGAAGC | TTAAATATTA | CAGACAGTAA | TAATGATGCT | 3300 |
| GAAATCCAAA | TTGGCGGCAA | TATCTCGCAA | AAGAAGGCA | ACCTCACGAT | TTCTTCCGAT | 3360 |
| AAAATTAATA | TCACCAAACA | GATAACAATC | AAAAAGGGTA | TTGATGGAGA | GGACTCTAGT | 3420 |
| TCAGATGCGA | CAAGTAATGC | CAACCTAACT | ATTAAAACCA | AGAATTGAA | ATTGACAGAA | 3480 |
| GACCTAAGTA | TTTCAGGTTT | CAATAAAGCA | GAGATTACAG | CCAAAGATGG | TAGAGATTTA | 3540 |
| ACTATTGGCA | ACAGTAATGA | CGGTAACAGC | GGTGCCGAAG | CCAAAACAGT | AACTTTTAAC | 3600 |
| AATGTTAAAG | ATTCAAAAAT | CTCTGCTGAC | GGTCACAATG | TGACACTAAA | TAGCAAAGTG | 3660 |
| AAAACATCTA | GCAGCAATGG | CGGACGTGAA | AGCAATAGCG | ACAACGATAC | CGGCTTAACT | 3720 |
| ATTACTGCAA | AAAATGTAGA | AGTAAACAAA | GATATTACTT | CTCTCAAAAC | AGTAAATATC | 3780 |
| ACCGCGTCGG | AAAAGGTTAC | CACCACAGCA | GGCTCGACCA | TTAACGCAAC | AAATGGCAAA | 3840 |
| GCAAGTATTA | CAACCAAAAC | AGGTGATATC | AGCGGTACGA | TTTCCGGTAA | CACGGTAAGT | 3900 |
| GTTAGCGCGA | CTGGTGATTT | AACCACTAAA | TCCGGCTCAA | AAATTGAAGC | GAAATCGGGT | 3960 |
| GAGGCTAATG | TAACAAGTGC | AACAGGTACA | ATTGGCGGTA | CAATTTCCGG | TAATACGGTA | 4020 |
| AATGTTACGG | CAAACGCTGG | CGATTTAACA | GTTGGGAATG | GCGCAGAAAT | TAATGCGACA | 4080 |
| GAAGGAGCTG | CAACCTTAAC | CGCAACAGGG | AATACCTTGA | CTACTGAAGC | CGGTTCTAGC | 4140 |
| ATCACTTCAA | CTAAGGGTCA | GGTAGACCTC | TTGGCTCAGA | ATGGTAGCAT | CGCAGGAAGC | 4200 |
| ATTAATGCTG | CTAATGTGAC | ATTAAATACT | ACAGGCACCT | TAACCACCGT | GGCAGGCTCG | 4260 |
| GATATTAAAG | CAACCAGCGG | CACCTTGGTT | ATTAACGCAA | AAGATGCTAA | GCTAAATGGT | 4320 |
| GATGCATCAG | GTGATAGTAC | AGAAGTGAAT | GCAGTCAACG | CAAGCGGCTC | TGGTAGTGTG | 4380 |
| ACTGCGGCAA | CCTCAAGCAG | TGTGAATATC | ACTGGGGATT | TAAACACAGT | AAATGGGTTA | 4440 |
| AATATCATTT | CGAAAGATGG | TAGAAACACT | GTGCGCTTAA | GAGGCAAGGA | AATTGAGGTG | 4500 |
| AAATATATCC | AGCCAGGTGT | AGCAAGTGTA | GAAGAAGTAA | TTGAAGCGAA | ACGCGTCCTT | 4560 |
| GAAAAGTAA | AAGATTTATC | TGATGAAGAA | AGAGAAACAT | TAGCTAAACT | TGGTGTAAGT | 4620 |
| GCTGTACGTT | TTGTTGAGCC | AAATAATACA | ATTACAGTCA | ATACACAAAA | TGAATTTACA | 4680 |
| ACCAGACCGT | CAAGTCAAGT | GATAATTTCT | GAAGGTAAGG | CGTGTTTCTC | AAGTGGTAAT | 4740 |
| GGCGCACGAG | TATGTACCAA | TGTTGCTGAC | GATGGACAGC | CGTAGTCAGT | AATTGACAAG | 4800 |
| GTAGATTTCA | TCCTGCAATG | AAGTCATTTT | ATTTTCGTAT | TATTTACTGT | GTGGGTTAAA | 4860 |
| GTTCAGTACG | GGCTTTACCC | ATCTTGTAAA | AAATTACGGA | GAATACAATA | AAGTATTTTT | 4920 |
| AACAGGTTAT | TATTATG | | | | | 4937 |

( 2 ) INFORMATION FOR SEQ ID NO:4:

( i ) SEQUENCE CHARACTERISTICS:
        ( A ) LENGTH: 1477 amino acids
        ( B ) TYPE: amino acid
        ( C ) STRANDEDNESS: single
        ( D ) TOPOLOGY: linear ( x i ) SEQUENCE DESCRIPTION: SEQ ID NO:4:

```
Met Asn Lys Ile Tyr Arg Leu Lys Phe Ser Lys Arg Leu Asn Ala Leu
 1               5                  10                  15
Val Ala Val Ser Glu Leu Ala Arg Gly Cys Asp His Ser Thr Glu Lys
                20                  25                  30
Gly Ser Glu Lys Pro Ala Arg Met Lys Val Arg His Leu Ala Leu Lys
                35                  40                  45
Pro Leu Ser Ala Met Leu Leu Ser Leu Gly Val Thr Ser Ile Pro Gln
            50                  55                  60
Ser Val Leu Ala Ser Gly Leu Gln Gly Met Asp Val Val His Gly Thr
 65                  70                  75                  80
Ala Thr Met Gln Val Asp Gly Asn Lys Thr Ile Ile Arg Asn Ser Val
                    85                  90                  95
Asp Ala Ile Ile Asn Trp Lys Gln Phe Asn Ile Asp Gln Asn Glu Met
               100                 105                 110
Val Gln Phe Leu Gln Glu Asn Asn Ser Ala Val Phe Asn Arg Val
               115                 120                 125
Thr Ser Asn Gln Ile Ser Gln Leu Lys Gly Ile Leu Asp Ser Asn Gly
           130                 135                 140
Gln Val Phe Leu Ile Asn Pro Asn Gly Ile Thr Ile Gly Lys Asp Ala
145                 150                 155                 160
Ile Ile Asn Thr Asn Gly Phe Thr Ala Ser Thr Leu Asp Ile Ser Asn
                165                 170                 175
Glu Asn Ile Lys Ala Arg Asn Phe Thr Phe Glu Gln Thr Lys Asp Lys
                180                 185                 190
Ala Leu Ala Glu Ile Val Asn His Gly Leu Ile Thr Val Gly Lys Asp
            195                 200                 205
Gly Ser Val Asn Leu Ile Gly Gly Lys Val Lys Asn Glu Gly Val Ile
    210                 215                 220
Ser Val Asn Gly Gly Ser Ile Ser Leu Leu Ala Gly Gln Lys Ile Thr
225                 230                 235                 240
Ile Ser Asp Ile Ile Asn Pro Thr Ile Thr Tyr Ser Ile Ala Ala Pro
                245                 250                 255
Glu Asn Glu Ala Val Asn Leu Gly Asp Ile Phe Ala Lys Gly Asn
                260                 265                 270
Ile Asn Val Arg Ala Ala Thr Ile Arg Asn Gln Gly Lys Leu Ser Ala
            275                 280                 285
Asp Ser Val Ser Lys Asp Lys Ser Gly Asn Ile Val Leu Ser Ala Lys
    290                 295                 300
Glu Gly Glu Ala Glu Ile Gly Gly Val Ile Ser Ala Gln Asn Gln Gln
305                 310                 315                 320
Ala Lys Gly Gly Lys Leu Met Ile Thr Gly Asp Lys Val Thr Leu Lys
                325                 330                 335
Thr Gly Ala Val Ile Asp Leu Ser Gly Lys Glu Gly Gly Glu Thr Tyr
                340                 345                 350
Leu Gly Gly Asp Glu Arg Gly Glu Gly Lys Asn Gly Ile Gln Leu Ala
            355                 360                 365
```

-continued

```
Lys Lys Thr Ser Leu Glu Lys Gly Ser Thr Ile Asn Val Ser Gly Lys
    370             375             380
Glu Lys Gly Gly Phe Ala Ile Val Trp Gly Asp Ile Ala Leu Ile Asp
385             390             395             400
Gly Asn Ile Asn Ala Gln Gly Ser Gly Asp Ile Ala Lys Thr Gly Gly
                405             410             415
Phe Val Glu Thr Ser Gly His Asp Leu Phe Ile Lys Asp Asn Ala Ile
            420             425             430
Val Asp Ala Lys Glu Trp Leu Leu Asp Phe Asp Asn Val Ser Ile Asn
            435             440             445
Ala Glu Asp Pro Leu Phe Asn Asn Thr Gly Ile Asn Asp Glu Phe Pro
    450             455             460
Thr Gly Thr Gly Glu Ala Ser Asp Pro Lys Lys Asn Ser Glu Leu Lys
465             470             475             480
Thr Thr Leu Thr Asn Thr Thr Ile Ser Asn Tyr Leu Lys Asn Ala Trp
                485             490             495
Thr Met Asn Ile Thr Ala Ser Arg Lys Leu Thr Val Asn Ser Ser Ile
            500             505             510
Asn Ile Gly Ser Asn Ser His Leu Ile Leu His Ser Lys Gly Gln Arg
        515             520             525
Gly Gly Gly Val Gln Ile Asp Gly Asp Ile Thr Ser Lys Gly Gly Asn
    530             535             540
Leu Thr Ile Tyr Ser Gly Gly Trp Val Asp Val His Lys Asn Ile Thr
545             550             555             560
Leu Asp Gln Gly Phe Leu Asn Ile Thr Ala Ala Ser Val Ala Phe Glu
                565             570             575
Gly Gly Asn Asn Lys Ala Arg Asp Ala Ala Asn Ala Lys Ile Val Ala
            580             585             590
Gln Gly Thr Val Thr Ile Thr Gly Glu Gly Lys Asp Phe Arg Ala Asn
            595             600             605
Asn Val Ser Leu Asn Gly Thr Gly Lys Gly Leu Asn Ile Ile Ser Ser
    610             615             620
Val Asn Asn Leu Thr His Asn Leu Ser Gly Thr Ile Asn Ile Ser Gly
625             630             635             640
Asn Ile Thr Ile Asn Gln Thr Thr Arg Lys Asn Thr Ser Tyr Trp Gln
                645             650             655
Thr Ser His Asp Ser His Trp Asn Val Ser Ala Leu Asn Leu Glu Thr
            660             665             670
Gly Ala Asn Phe Thr Phe Ile Lys Tyr Ile Ser Ser Asn Ser Lys Gly
            675             680             685
Leu Thr Thr Gln Tyr Arg Ser Ser Ala Gly Val Asn Phe Asn Gly Val
    690             695             700
Asn Gly Asn Met Ser Phe Asn Leu Lys Glu Gly Ala Lys Val Asn Phe
705             710             715             720
Lys Leu Lys Pro Asn Glu Asn Met Asn Thr Ser Lys Pro Leu Pro Ile
                725             730             735
Arg Phe Leu Ala Asn Ile Thr Ala Thr Gly Gly Gly Ser Val Phe Phe
            740             745             750
Asp Ile Tyr Ala Asn His Ser Gly Arg Gly Ala Glu Leu Lys Met Ser
        755             760             765
Glu Ile Asn Ile Ser Asn Gly Ala Asn Phe Thr Leu Asn Ser His Val
    770             775             780
Arg Gly Asp Asp Ala Phe Lys Ile Asn Lys Asp Leu Thr Ile Asn Ala
785             790             795             800
```

Thr Asn Ser Asn Phe Ser Leu Arg Gln Thr Lys Asp Asp Phe Tyr Asp
                    805                 810                 815

Gly Tyr Ala Arg Asn Ala Ile Asn Ser Thr Tyr Asn Ile Ser Ile Leu
            820                 825                 830

Gly Gly Asn Val Thr Leu Gly Gly Gln Asn Ser Ser Ser Ile Thr
        835                 840                 845

Gly Asn Ile Thr Ile Glu Lys Ala Ala Asn Val Thr Leu Glu Ala Asn
850                 855                 860

Asn Ala Pro Asn Gln Gln Asn Ile Arg Asp Arg Val Ile Lys Leu Gly
865                 870                 875                 880

Ser Leu Leu Val Asn Gly Ser Leu Ser Leu Thr Gly Glu Asn Ala Asp
                885                 890                 895

Ile Lys Gly Asn Leu Thr Ile Ser Glu Ser Ala Thr Phe Lys Gly Lys
            900                 905                 910

Thr Arg Asp Thr Leu Asn Ile Thr Gly Asn Phe Thr Asn Asn Gly Thr
        915                 920                 925

Ala Glu Ile Asn Ile Thr Gln Gly Val Val Lys Leu Gly Asn Val Thr
        930                 935                 940

Asn Asp Gly Asp Leu Asn Ile Thr Thr His Ala Lys Arg Asn Gln Arg
945                 950                 955                 960

Ser Ile Ile Gly Gly Asp Ile Ile Asn Lys Lys Gly Ser Leu Asn Ile
                965                 970                 975

Thr Asp Ser Asn Asn Asp Ala Glu Ile Gln Ile Gly Gly Asn Ile Ser
            980                 985                 990

Gln Lys Glu Gly Asn Leu Thr Ile Ser Ser Asp Lys Ile Asn Ile Thr
        995                 1000                1005

Lys Gln Ile Thr Ile Lys Lys Gly Ile Asp Gly Glu Asp Ser Ser Ser
    1010                1015                1020

Asp Ala Thr Ser Asn Ala Asn Leu Thr Ile Lys Thr Lys Glu Leu Lys
1025                1030                1035                1040

Leu Thr Glu Asp Leu Ser Ile Ser Gly Phe Asn Lys Ala Glu Ile Thr
            1045                1050                1055

Ala Lys Asp Gly Arg Asp Leu Thr Ile Gly Asn Ser Asn Asp Gly Asn
            1060                1065                1070

Ser Gly Ala Glu Ala Lys Thr Val Thr Phe Asn Asn Val Lys Asp Ser
        1075                1080                1085

Lys Ile Ser Ala Asp Gly His Asn Val Thr Leu Asn Ser Lys Val Lys
        1090                1095                1100

Thr Ser Ser Ser Asn Gly Gly Arg Glu Ser Asn Ser Asp Asn Asp Thr
1105                1110                1115                1120

Gly Leu Thr Ile Thr Ala Lys Asn Val Glu Val Asn Lys Asp Ile Thr
            1125                1130                1135

Ser Leu Lys Thr Val Asn Ile Thr Ala Ser Glu Lys Val Thr Thr Thr
            1140                1145                1150

Ala Gly Ser Thr Ile Asn Ala Thr Asn Gly Lys Ala Ser Ile Thr Thr
        1155                1160                1165

Lys Thr Gly Asp Ile Ser Gly Thr Ile Ser Gly Asn Thr Val Ser Val
        1170                1175                1180

Ser Ala Thr Val Asp Leu Thr Thr Lys Ser Gly Ser Lys Ile Glu Ala
1185                1190                1195                1200

Lys Ser Gly Glu Ala Asn Val Thr Ser Ala Thr Gly Thr Ile Gly Gly
            1205                1210                1215

Thr Ile Ser Gly Asn Thr Val Asn Val Thr Ala Asn Ala Gly Asp Leu

|       |       |       |       |       |       |       |       |       |       |       |       |       |       |       |
|-------|-------|-------|-------|-------|-------|-------|-------|-------|-------|-------|-------|-------|-------|-------|
|       |       |       |       | 1220  |       |       |       |       | 1225  |       |       |       |       | 1230  |
|  Thr  |  Val  |  Gly  |  Asn  |  Gly  |  Ala  |  Glu  |  Ile  |  Asn  |  Ala  |  Thr  |  Glu  |  Gly  |  Ala  |  Ala  |  Thr  |
|       |       |       |       | 1235  |       |       |       |       | 1240  |       |       |       |       | 1245  |
|  Leu  |  Thr  |  Ala  |  Thr  |  Gly  |  Asn  |  Thr  |  Leu  |  Thr  |  Thr  |  Glu  |  Ala  |  Gly  |  Ser  |  Ser  |  Ile  |
|       |       |       |       | 1250  |       |       |       |       | 1255  |       |       |       |       | 1260  |
|  Thr  |  Ser  |  Thr  |  Lys  |  Gly  |  Gln  |  Val  |  Asp  |  Leu  |  Leu  |  Ala  |  Gln  |  Asn  |  Gly  |  Ser  |  Ile  |
|  1265 |       |       |       |       |  1270 |       |       |       |       |  1275 |       |       |       |       |  1280 |
|  Ala  |  Gly  |  Ser  |  Ile  |  Asn  |  Ala  |  Ala  |  Asn  |  Val  |  Thr  |  Leu  |  Asn  |  Thr  |  Thr  |  Gly  |  Thr  |
|       |       |       |       | 1285  |       |       |       |       | 1290  |       |       |       |       | 1295  |
|  Leu  |  Thr  |  Thr  |  Val  |  Ala  |  Gly  |  Ser  |  Asp  |  Ile  |  Lys  |  Ala  |  Thr  |  Ser  |  Gly  |  Thr  |  Leu  |
|       |       |       |       | 1300  |       |       |       |       | 1305  |       |       |       |       | 1310  |
|  Val  |  Ile  |  Asn  |  Ala  |  Lys  |  Asp  |  Ala  |  Lys  |  Leu  |  Asn  |  Gly  |  Asp  |  Ala  |  Ser  |  Gly  |  Asp  |
|       |       |       |       | 1315  |       |       |       |       | 1320  |       |       |       |       | 1325  |
|  Ser  |  Thr  |  Glu  |  Val  |  Asn  |  Ala  |  Val  |  Asn  |  Ala  |  Ser  |  Gly  |  Ser  |  Gly  |  Ser  |  Val  |  Thr  |
|       |       |       |       | 1330  |       |       |       |       | 1335  |       |       |       |       | 1340  |
|  Ala  |  Ala  |  Thr  |  Ser  |  Ser  |  Ser  |  Val  |  Asn  |  Ile  |  Thr  |  Gly  |  Asp  |  Leu  |  Asn  |  Thr  |  Val  |
|  1345 |       |       |       |       |  1350 |       |       |       |       |  1355 |       |       |       |       |  1360 |
|  Asn  |  Gly  |  Leu  |  Asn  |  Ile  |  Ile  |  Ser  |  Lys  |  Asp  |  Gly  |  Arg  |  Asn  |  Thr  |  Val  |  Arg  |  Leu  |
|       |       |       |       | 1365  |       |       |       |       | 1370  |       |       |       |       | 1375  |
|  Arg  |  Gly  |  Lys  |  Glu  |  Ile  |  Glu  |  Val  |  Lys  |  Tyr  |  Ile  |  Gln  |  Pro  |  Gly  |  Val  |  Ala  |  Ser  |
|       |       |       |       | 1380  |       |       |       |       | 1385  |       |       |       |       | 1390  |
|  Val  |  Glu  |  Glu  |  Val  |  Ile  |  Glu  |  Ala  |  Lys  |  Arg  |  Val  |  Leu  |  Glu  |  Lys  |  Val  |  Lys  |  Asp  |
|       |       |       |       | 1395  |       |       |       |       | 1400  |       |       |       |       | 1405  |
|  Leu  |  Ser  |  Asp  |  Glu  |  Glu  |  Arg  |  Glu  |  Thr  |  Leu  |  Ala  |  Lys  |  Leu  |  Gly  |  Val  |  Ser  |  Ala  |
|       |       |       |       | 1410  |       |       |       |       | 1415  |       |       |       |       | 1420  |
|  Val  |  Arg  |  Phe  |  Val  |  Glu  |  Pro  |  Asn  |  Asn  |  Thr  |  Ile  |  Thr  |  Val  |  Asn  |  Thr  |  Gln  |  Asn  |
|  1425 |       |       |       |       |  1430 |       |       |       |       |  1435 |       |       |       |       |  1440 |
|  Glu  |  Phe  |  Thr  |  Thr  |  Arg  |  Pro  |  Ser  |  Ser  |  Gln  |  Val  |  Ile  |  Ile  |  Ser  |  Glu  |  Gly  |  Lys  |
|       |       |       |       | 1445  |       |       |       |       | 1450  |       |       |       |       | 1455  |
|  Ala  |  Cys  |  Phe  |  Ser  |  Ser  |  Gly  |  Asn  |  Gly  |  Ala  |  Arg  |  Val  |  Cys  |  Thr  |  Asn  |  Val  |  Ala  |
|       |       |       |       | 1460  |       |       |       |       | 1465  |       |       |       |       | 1470  |
|  Asp  |  Asp  |  Gly  |  Gln  |  Pro  |       |       |       |       |       |       |       |       |       |       |       |
|       |       |       |       | 1475  |       |       |       |       |       |       |       |       |       |       |       |

( 2 ) INFORMATION FOR SEQ ID NO:5:

( i ) SEQUENCE CHARACTERISTICS:
        ( A ) LENGTH: 9171 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

```
ACAGCGTTCT  CTTAATACTA  GTACAAACCC  ACAATAAAAT  ATGACAAACA  ACAATTACAA       60
CACCTTTTTT  GCAGTCTATA  TGCAAATATT  TTAAAAAATA  GTATAAATCC  GCCATATAAA      120
ATGGTATAAT  CTTTCATCTT  TCATCTTTCA  TCTTTCATCT  TTCATCTTTC  ATCTTTCATC      180
TTTCATCTTT  CATCTTTCAT  CTTTCATCTT  TCATCTTTCA  TCTTTCATCT  TTCATCTTTC      240
ACATGAAATG  ATGAACCGAG  GGAAGGGAGG  GAGGGGCAAG  AATGAAGAGG  GAGCTGAACG      300
AACGCAAATG  ATAAAGTAAT  TTAATTGTTC  AACTAACCTT  AGGAGAAAAT  ATGAACAAGA      360
TATATCGTCT  CAAATTCAGC  AAACGCCTGA  ATGCTTTGGT  TGCTGTGTCT  GAATTGGCAC      420
GGGGTTGTGA  CCATTCCACA  GAAAAAGGCA  GCGAAAAACC  TGCTCGCATG  AAAGTGCGTC      480
ACTTAGCGTT  AAAGCCACTT  TCCGCTATGT  TACTATCTTT  AGGTGTAACA  TCTATTCCAC      540
```

```
AATCTGTTTT  AGCAAGCGGC  TTACAAGGAA  TGGATGTAGT  ACACGGCACA  GCCACTATGC   600
AAGTAGATGG  TAATAAAACC  ATTATCCGCA  ACAGTGTTGA  CGCTATCATT  AATTGGAAAC   660
AATTTAACAT  CGACCAAAAT  GAAATGGTGC  AGTTTTTACA  AGAAAACAAC  AACTCCGCCG   720
TATTCAACCG  TGTTACATCT  AACCAAATCT  CCCAATTAAA  AGGGATTTTA  GATTCTAACG   780
GACAAGTCTT  TTTAATCAAC  CCAAATGGTA  TCACAATAGG  TAAAGACGCA  ATTATTAACA   840
CTAATGGCTT  TACGGCTTCT  ACGCTAGACA  TTTCTAACGA  AAACATCAAG  GCGCGTAATT   900
TCACCTTCGA  GCAAACCAAA  GATAAAGCGC  TCGCTGAAAT  TGTGAATCAC  GGTTTAATTA   960
CTGTCGGTAA  AGACGGCAGT  GTAAATCTTA  TTGGTGGCAA  AGTGAAAAAC  GAGGGTGTGA  1020
TTAGCGTAAA  TGGTGGCAGC  ATTTCTTTAC  TCGCAGGGCA  AAAAATCACC  ATCAGCGATA  1080
TAATAAACCC  AACCATTACT  TACAGCATTG  CCGCGCCTGA  AAATGAAGCG  GTCAATCTGG  1140
GCGATATTTT  TGCCAAGGGC  GGTAACATTA  ATGTCCGTGC  TGCCACTATT  CGAAACCAAG  1200
CTTTCCGCCA  AGAGGGTGA   AGCGGAAATT  GGCGGTGTAA  TTTCCGCTCA  AAATCAGCAA  1260
GCTAAAGGCG  GCAAGCTGAT  GATTACAGGC  GATAAAGTCA  CATTAAAAAC  AGGTGCAGTT  1320
ATCGACCTTT  CAGGTAAAGA  AGGGGGAGAA  ACTTACCTTG  GCGGTGACGA  GCGCGGCGAA  1380
GGTAAAAACG  GCATTCAATT  AGCAAAGAAA  ACCTCTTTAG  AAAAAGGCTC  AACCATCAAT  1440
GTATCAGGCA  AAGAAAAAGG  CGGACGCGCT  ATTGTGTGGG  GCGATATTGC  GTTAATTGAC  1500
GGCAATATTA  ACGCTCAAGG  TAGTGGTGAT  ATCGCTAAAA  CCGGTGGTTT  TGTGGAGACG  1560
TCGGGGCATG  ATTTATTCAT  CAAAGACAAT  GCAATTGTTG  ACGCCAAAGA  GTGGTTGTTA  1620
GACCCGGATA  ATGTATCTAT  TAATGCAGAA  ACAGCAGGAC  GCAGCAATAC  TTCAGAAGAC  1680
GATGAATACA  CGGGATCCGG  GAATAGTGCC  AGCACCCCAA  AACGAAACAA  AGAAAAGACA  1740
ACATTAACAA  ACACAACTCT  TGAGAGTATA  CTAAAAAAAG  GTACCTTTGT  TAACATCACT  1800
GCTAATCAAC  GCATCTATGT  CAATAGCTCC  ATTAATTTAT  CCAATGGCAG  CTTAACTCTT  1860
TGGAGTGAGG  GTCGGAGCGG  TGGCGGCGTT  GAGATTAACA  ACGATATTAC  CACCGGTGAT  1920
GATACCAGAG  GTGCAAACTT  AACAATTTAC  TCAGGCGGCT  GGGTTGATGT  TCATAAAAAT  1980
ATCTCACTCG  GGGCGCAAGG  TAACATAAAC  ATTACAGCTA  ACAAGATAT   CGCCTTTGAG  2040
AAAGGAAGCA  ACCAAGTCAT  TACAGGTCAA  GGGACTATTA  CCTCAGGCAA  TCAAAAAGGT  2100
TTTAGATTTA  ATAATGTCTC  TCTAAACGGC  ACTGGCAGCG  GACTGCAATT  CACCACTAAA  2160
AGAACCAATA  AATACGCTAT  CACAAATAAA  TTTGAAGGGA  CTTTAAATAT  TTCAGGGAAA  2220
GTGAACATCT  CAATGGTTTT  ACCTAAAAAT  GAAAGTGGAT  ATGATAAATT  CAAAGGACGC  2280
ACTTACTGGA  ATTTAACCTC  GAAAGTGGAT  ATGATAAATT  CAAAGGACGC  CCTCACTATT  2340
GACTCCAGAG  GAAGCGATAG  TGCAGGCACA  CTTACCCAGC  CTTATAATTT  AAACGGTATA  2400
TCATTCAACA  AAGACACTAC  CTTTAATGTT  GAACGAAATG  CAAGAGTCAA  CTTTGACATC  2460
AAGGCACCAA  TAGGGATAAA  TAAGTATTCT  AGTTTGAATT  ACGCATCATT  TAATGGAAAC  2520
ATTTCAGTTT  CGGGAGGGGG  GAGTGTTGAT  TTCACACTTC  TCGCCTCATC  CTCTAACGTC  2580
CAAACCCCCG  GTGTAGTTAT  AAATTCTAAA  TACTTTAATG  TTTCAACAGG  GTCAAGTTTA  2640
AGATTTAAAA  CTTCAGGCTC  AACAAAAACT  GGCTTCTCAA  TAGAGAAAGA  TTTAACTTTA  2700
AATGCCACCG  GAGGCAACAT  AACACTTTTG  CAAGTTGAAG  GCACCGATGG  AATGATTGGT  2760
AAAGGCATTG  TAGCCAAAAA  AAACATAACC  TTTGAAGGAG  GTAAGATGAG  GTTTGGCTCC  2820
AGGAAAGCCG  TAACAGAAAT  CGAAGGCAAT  GTTACTATCA  ATAACAACGC  TAACGTCACT  2880
CTTATCGGTT  CGGATTTTGA  CAACCATCAA  AAACCTTTAA  CTATTAAAAA  AGATGTCATC  2940
```

```
ATTAATAGCG  GCAACCTTAC  CGCTGGAGGC  AATATTGTCA  ATATAGCCGG  AAATCTTACC   3000

GTTGAAAGTA  ACGCTAATTT  CAAAGCTATC  ACAAATTTCA  CTTTTAATGT  AGGCGGCTTG   3060

TTTGACAACA  AAGGCAATTC  AAATATTTCC  ATTGCCAAAG  GAGGGGCTCG  CTTTAAAGAC   3120

ATTGATAATT  CCAAGAATTT  AAGCATCACC  ACCAACTCCA  GCTCCACTTA  CCGCACTATT   3180

ATAAGCGGCA  ATATAACCAA  TAAAAACGGT  GATTTAAATA  TTACGAACGA  AGGTAGTGAT   3240

ACTGAAATGC  AAATTGGCGG  CGATGTCTCG  CAAAAGAAG   GTAATCTCAC  GATTTCTTCT   3300

GACAAAATCA  ATATTACCAA  ACAGATAACA  ATCAAGGCAG  GTGTTGATGG  GGAGAATTCC   3360

GATTCAGACG  CGACAAACAA  TGCCAATCTA  ACCATTAAAA  CCAAGAATT   GAAATTAACG   3420

CAAGACCTAA  ATATTTCAGG  TTTCAATAAA  GCAGAGATTA  CAGCTAAAGA  TGGTAGTGAT   3480

TTAACTATTG  GTAACACCAA  TAGTGCTGAT  GGTACTAATG  CCAAAAAGT   AACCTTTAAC   3540

CAGGTTAAAG  ATTCAAAAAT  CTCTGCTGAC  GGTCACAAGG  TGACACTACA  CAGCAAAGTG   3600

GAAACATCCG  GTAGTAATAA  CAACACTGAA  GATAGCAGTG  ACAATAATGC  CGGCTTAACT   3660

ATCGATGCAA  AAAATGTAAC  AGTAAACAAC  AATATTACTT  CTCACAAAGC  AGTGAGCATC   3720

TCTGCGACAA  GTGGAGAAAT  TACCACTAAA  ACAGGTACAA  CCATTAACGC  AACCACTGGT   3780

AACGTGGAGA  TAACCGCTCA  AACAGGTAGT  ATCCTAGGTG  GAATTGAGTC  CAGCTCTGGC   3840

TCTGTAACAC  TTACTGCAAC  CGAGGGCGCT  CTTGCTGTAA  GCAATATTTC  GGGCAACACC   3900

GTTACTGTTA  CTGCAAATAG  CGGTGCATTA  ACCACTTTGG  CAGGCTCTAC  AATTAAAGGA   3960

ACCGAGAGTG  TAACCACTTC  AAGTCAATCA  GGCGATATCG  GCGGTACGAT  TTCTGGTGGC   4020

ACAGTAGAGG  TTAAAGCAAC  CGAAAGTTTA  ACCACTCAAT  CCAATTCAAA  AATTAAAGCA   4080

ACAACAGGCG  AGGCTAACGT  AACAAGTGCA  ACAGGTACAA  TTGGTGGTAC  GATTTCCGGT   4140

AATACGGTAA  ATGTTACGGC  AAACGCTGGC  GATTTAACAG  TTGGGAATGG  CGCAGAAATT   4200

AATGCGACAG  AAGGAGCTGC  AACCTTAACT  ACATCATCGG  GCAAATTAAC  TACCGAAGCT   4260

AGTTCACACA  TTACTTCAGC  CAAGGGTCAG  GTAAATCTTT  CAGCTCAGGA  TGGTAGCGTT   4320

GCAGGAAGTA  TTAATGCCGC  CAATGTGACA  CTAAATACTA  CAGGCACTTT  AACTACCGTG   4380

AAGGGTTCAA  ACATTAATGC  AACCAGCGGT  ACCTTGGTTA  TTAACGCAAA  AGACGCTGAG   4440

CTAAATGGCG  CAGCATTGGG  TAACCACACA  GTGGTAAATG  CAACCAACGC  AAATGGCTCC   4500

GGCAGCGTAA  TCGCGACAAC  CTCAAGCAGA  GTGAACATCA  CTGGGGATTT  AATCACAATA   4560

AATGGATTAA  ATATCATTTC  AAAAAACGGT  ATAAACACCG  TACTGTTAAA  AGGCGTTAAA   4620

ATTGATGTGA  AATACATTCA  ACCGGGTATA  GCAAGCGTAG  ATGAAGTAAT  TGAAGCGAAA   4680

CGCATCCTTG  AGAAGGTAAA  AGATTTATCT  GATGAAGAAA  GAGAAGCGTT  AGCTAAACTT   4740

GGCGTAAGTG  CTGTACGTTT  TATTGAGCCA  AATAATACAA  TTACAGTCGA  TACACAAAAT   4800

GAATTTGCAA  CCAGACCATT  AAGTCGAATA  GTGATTTCTG  AAGGCAGGGC  GTGTTTCTCA   4860

AACAGTGATG  GCGCGACGGT  GTGCGTTAAT  ATCGCTGATA  ACGGGCGGTA  GCGGTCAGTA   4920

ATTGACAAGG  TAGATTTCAT  CCTGCAATGA  AGTCATTTTA  TTTTCGTATT  ATTTACTGTG   4980

TGGGTTAAAG  TTCAGTACGG  GCTTTACCCA  TCTTGTAAAA  AATTACGGAG  AATACAATAA   5040

AGTATTTTTA  ACAGGTTATT  ATTATGAAAA  ATATAAAAAG  CAGATTAAAA  CTCAGTGCAA   5100

TATCAGTATT  GCTTGGCCTG  GCTTCTTCAT  CATTGTATGC  AGAAGAAGCG  TTTTTAGTAA   5160

AAGGCTTTCA  GTTATCTGGT  GCACTTGAAA  CTTAAGTGA   AGACGCCCAA  CTGTCTGTAG   5220

CAAAATCTTT  ATCTAAATAC  CAAGGCTCGC  AAACTTTAAC  AAACCTAAAA  ACAGCACAGC   5280

TTGAATTACA  GGCTGTGCTA  GATAAGATTG  AGCCAAATAA  GTTTGATGTG  ATATTGCCAC   5340
```

```
AACAAACCAT TACGGATGGC AATATTATGT TTGAGCTAGT CTCGAAATCA GCCGCAGAAA    5400
GCCAAGTTTT TTATAAGGCG AGCCAGGGTT ATAGTGAAGA AAATATCGCT CGTAGCCTGC    5460
CATCTTTGAA ACAAGGAAAA GTGTATGAAG ATGGTCGTCA GTGGTTCGAT TTGCGTGAAT    5520
TCAATATGGC AAAAGAAAAT CCACTTAAAG TCACTCGCGT GCATTACGAG TTAAACCCTA    5580
AAAACAAAAC CTCTGATTTG GTAGTTGCAG GTTTTCGCC TTTTGGCAAA ACGCGTAGCT    5640
TTGTTTCCTA TGATAATTTC GGCGCAAGGG AGTTAACTA TCAACGTGTA AGTCTAGGTT    5700
TTGTAAATGC CAATTTGACC GGACATGATG ATGTATTAAA TCTAAACGCA TTGACCAATG    5760
TAAAAGCACC ATCAAAATCT TATGCGGTAG GCATAGGATA TACTTATCCG TTTTATGATA    5820
AACACCAATC CTTAAGTCTT TATACCAGCA TGAGTTATGC TGATTCTAAT GATATCGACG    5880
GCTTACCAAG TGCGATTAAT CGTAAATTAT CAAAAGGTCA ATCTATCTCT GCGAATCTGA    5940
AATGGAGTTA TTATCTCCCG ACATTTAACC TTGGAATGGA AGACCAGTTT AAAATTAATT    6000
TAGGCTACAA CTACCGCCAT ATTAATCAAA CATCCGAGTT AAACACCCTG GGTGCAACGA    6060
AGAAAAAATT TGCAGTATCA GGCGTAAGTG CAGGCATTGA TGGACATATC CAATTTACCC    6120
CTAAACAAT CTTTAATATT GATTTAACTC ATCATTATTA CGCGAGTAAA TTACCAGGCT    6180
CTTTTGGAAT GGAGCGCATT GGCGAAACAT TTAATCGCAG CTATCACATT AGCACAGCCA    6240
GTTAGGGTT GAGTCAAGAG TTTGCTCAAG GTTGGCATTT TAGCAGTCAA TTATCGGGTC    6300
AGTTACTCT ACAAGATATA AGTAGCATAG ATTTATTCTC TGTAACAGGT ACTTATGGCG    6360
TCAGAGGCTT TAAATACGGC GGTGCAAGTG GTGAGCGCGG TCTTGTATGG CGTAATGAAT    6420
TAAGTATGCC AAAATACACC CGCTTTCAAA TCAGCCCTTA TGCGTTTTAT GATGCAGGTC    6480
AGTTCCGTTA TAATAGCGAA AATGCTAAAA CTTACGGCGA AGATATGCAC ACGGTATCCT    6540
CTGCGGGTTT AGGCATTAAA ACCTCTCCTA CACAAAACTT AAGCTTAGAT GCTTTTGTTG    6600
CTCGTCGCTT TGCAAATGCC AATAGTGACA ATTTGAATGG CAACAAAAAA CGCACAAGCT    6660
CACCTACAAC CTTCTGGGGT AGATTAACAT TCAGTTTCTA ACCCTGAAAT TTAATCAACT    6720
GGTAAGCGTT CCGCCTACCA GTTTATAACT ATATGCTTTA CCCGCCAATT TACAGTCTAT    6780
ACGCAACCCT GTTTTCATCC TTATATATCA AACAAACTAA GCAAACCAAG CAAACCAAGC    6840
AAACCAAGCA AACCAAGCAA ACCAAGCAAA CCAAGCAAAC CAAGCAAACC AAGCAAACCA    6900
AGCAAACCAA GCAAACCAAG CAAACCAAGC AAACCAAGCA ATGCTAAAAA ACAATTTATA    6960
TGATAAACTA AAACATACTC CATACCATGG CAATACAAGG GATTAATAA TATGACAAAA    7020
GAAAATTTAC AAAGTGTTCC ACAAAATACG ACCGCTTCAC TTGTAGAATC AAACAACGAC    7080
CAAACTTCCC TGCAAATACT TAAACAACCA CCCAAACCCA ACCTATTACG CCTGGAACAA    7140
CATGTCGCCA AAAAGATTA TGAGCTTGCT TGCCGCGAAT TAATGGCGAT TTTGGAAAAA    7200
ATGGACGCTA ATTTTGGAGG CGTTCACGAT ATTGAATTTG ACGCACCTGC TCAGCTGGCA    7260
TATCTACCCG AAAAACTACT AATTCATTTT GCCACTCGTC TCGCTAATGC AATTACAACA    7320
CTCTTTTCCG ACCCCGAATT GGCAATTTCC GAAGAAGGGG CATTAAAGAT GATTAGCCTG    7380
CAACGCTGGT TGACGCTGAT TTTTGCCTCT TCCCCCTACG TTAACGCAGA CCATATTCTC    7440
AATAAATATA ATATCAACCC AGATTCCGAA GGTGGCTTTC ATTTAGCAAC AGACAACTCT    7500
TCTATTGCTA AATTCTGTAT TTTTTACTTA CCCGAATCCA ATGTCAATAT GAGTTTAGAT    7560
GCGTTATGGG CAGGGAATCA ACAACTTTGT GCTTCATTGT GTTTTGCGTT GCAGTCTTCA    7620
CGTTTTATTG GTACTGCATC TGCGTTTCAT AAAAGAGCGG TGGTTTTACA GTGGTTTCCT    7680
AAAAAACTCG CCGAAATTGC TAATTTAGAT GAATTGCCTG CAAATATCCT TCATGATGTA    7740
```

| | | | | | |
|---|---|---|---|---|---|
| TATATGCACT | GCAGTTATGA | TTTAGCAAAA | AACAAGCACG | ATGTTAAGCG | TCCATTAAAC | 7800
| GAACTTGTCC | GCAAGCATAT | CCTCACGCAA | GGATGGCAAG | ACCGCTACCT | TTACACCTTA | 7860
| GGTAAAAAGG | ACGGCAAACC | TGTGATGATG | GTACTGCTTG | AACATTTTAA | TTCGGGACAT | 7920
| TCGATTTATC | GCACGCATTC | AACTTCAATG | ATTGCTGCTC | GAGAAAAATT | CTATTTAGTC | 7980
| GGCTTAGGCC | ATGAGGGCGT | TGATAACATA | GGTCGAGAAG | TGTTTGACGA | GTTCTTTGAA | 8040
| ATCAGTAGCA | ATAATATAAT | GGAGAGACTG | TTTTTTATCC | GTAAACAGTG | CGAAACTTTC | 8100
| CAACCCGCAG | TGTTCTATAT | GCCAAGCATT | GGCATGGATA | TTACCACGAT | TTTTGTGAGC | 8160
| AACACTCGGC | TTGCCCCTAT | TCAAGCTGTA | GCCTTGGGTC | ATCCTGCCAC | TACGCATTCT | 8220
| GAATTTATTG | ATTATGTCAT | CGTAGAAGAT | GATTATGTGG | GCAGTGAAGA | TTGTTTTAGC | 8280
| GAAACCCTTT | TACGCTTACC | CAAAGATGCC | CTACCTTATG | TACCATCTGC | ACTCGCCCCA | 8340
| CAAAAGTGG | ATTATGTACT | CAGGGAAAAC | CCTGAAGTAG | TCAATATCGG | TATTGCCGCT | 8400
| ACCACAATGA | AATTAAACCC | TGAATTTTTG | CTAACATTGC | AAGAAATCAG | AGATAAAGCT | 8460
| AAAGTCAAAA | TACATTTTCA | TTTCGCACTT | GGACAATCAA | CAGGCTTGAC | ACACCCTTAT | 8520
| GTCAAATGGT | TTATCGAAAG | CTATTTAGGT | GACGATGCCA | CTGCACATCC | CCACGCACCT | 8580
| TATCACGATT | ATCTGGCAAT | ATTGCGTGAT | TGCGATATGC | TACTAAATCC | GTTTCCTTTC | 8640
| GGTAATACTA | ACGGCATAAT | TGATATGGTT | ACATTAGGTT | TAGTTGGTGT | ATGCAAAACG | 8700
| GGGGATGAAG | TACATGAACA | TATTGATGAA | GGTCTGTTTA | AACGCTTAGG | ACTACCAGAA | 8760
| TGGCTGATAG | CCGACACACG | AGAAACATAT | ATTGAATGTG | CTTTGCGTCT | AGCAGAAAAC | 8820
| CATCAAGAAC | GCCTTGAACT | CCGTCGTTAC | ATCATAGAAA | ACAACGGCTT | ACAAAAGCTT | 8880
| TTTACAGGCG | ACCCTCGTCC | ATTGGGCAAA | ATACTGCTTA | AGAAAACAAA | TGAATGGAAG | 8940
| CGGAAGCACT | TGAGTAAAAA | ATAACGGTTT | TTTAAAGTAA | AAGTGCGGTT | AATTTTCAAA | 9000
| GCGTTTTAAA | AACCTCTCAA | AAATCAACCG | CACTTTTATC | TTTATAACGC | TCCCGCGCGC | 9060
| TGACAGTTTA | TCTCTTTCTT | AAAATACCCA | TAAAATTGTG | GCAATAGTTG | GGTAATCAAA | 9120
| TTCAATTGTT | GATACGGCAA | ACTAAAGACG | GCGCGTTCTT | CGGCAGTCAT | C | 9171

( 2 ) INFORMATION FOR SEQ ID NO:6:

( i ) SEQUENCE CHARACTERISTICS:
        ( A ) LENGTH: 9323 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

| | | | | | |
|---|---|---|---|---|---|
| CGCCACTTCA | ATTTTGGATT | GTTGAAATTC | AACTAACCAA | AAAGTGCGGT | TAAAATCTGT | 60
| GGAGAAAATA | GGTTGTAGTG | AAGAACGAGG | TAATTGTTCA | AAAGGATAAA | GCTCTCTTAA | 120
| TTGGGCATTG | GTTGGCGTTT | CTTTTCGGT | TAATAGTAAA | TTATATTCTG | GACGACTATG | 180
| CAATCCACCA | ACAACTTTAC | CGTTGGTTTT | AAGCGTTAAT | GTAAGTTCTT | GCTCTTCTTG | 240
| GCGAATACGT | AATCCCATTT | TTTGTTTAGC | AAGAAAATGA | TCGGGATAAT | CATAATAGGT | 300
| GTTGCCCAAA | AATAAATTTT | GATGTTCTAA | AATCATAAAT | TTTGCAAGAT | ATTGTGGCAA | 360
| TTCAATACCT | ATTTGTGGCG | AAATCGCCAA | TTTTAATTCA | ATTTCTTGTA | GCATAATATT | 420
| TCCCACTCAA | ATCAACTGGT | TAAATATACA | AGATAATAAA | AATAAATCAA | GATTTTTGTG | 480
| ATGACAAACA | ACAATTACAA | CACCTTTTTT | GCAGTCTATA | TGCAAATATT | TTAAAAAAAT | 540

| | | | | | | |
|---|---|---|---|---|---|---|
| AGTATAAATC | CGCCATATAA | AATGGTATAA | TCTTTCATCT | TTCATCTTTC | ATCTTTCATC | 600 |
| TTTCATCTTT | CATCTTTCAT | CTTTCATCTT | TCATCTTTCA | TCTTTCATCT | TTCATCTTTC | 660 |
| ATCTTTCATC | TTTCATCTTT | CACATGAAAT | GATGAACCGA | GGGAAGGGAG | GGAGGGGCAA | 720 |
| GAATGAAGAG | GGAGCTGAAC | GAACGCAAAT | GATAAAGTAA | TTTAATTGTT | CAACTAACCT | 780 |
| TAGGAGAAAA | TATGAACAAG | ATATATCGTC | TCAAATTCAG | CAAACGCCTG | AATGCTTTGG | 840 |
| TTGCTGTGTC | TGAATTGGCA | CGGGGTTGTG | ACCATTCCAC | AGAAAAGGC | AGCGAAAAC | 900 |
| CTGCTCGCAT | GAAAGTGCGT | CACTTAGCGT | TAAAGCCACT | TTCCGCTATG | TTACTATCTT | 960 |
| TAGGTGTAAC | ATCTATTCCA | CAATCTGTTT | TAGCAAGCGG | CAATTTAACA | TCGACCAAAA | 1020 |
| TGAAATGGTG | CAGTTTTTAC | AAGAAAACAA | GTAATAAAAC | CATTATCCGC | AACAGTGTTG | 1080 |
| ACGCTATCAT | TAATTGGAAA | CAATTTAACA | TCGACCAAAA | TGAAATGGTG | CAGTTTTTAC | 1140 |
| AAGAAAACAA | CAACTCCGCC | GTATTCAACC | GTGTTACATC | TAACCAAATC | TCCCAATTAA | 1200 |
| AAGGGATTTT | AGATTCTAAC | GGACAAGTCT | TTTTAATCAA | CCCAAATGGT | ATCACAATAG | 1260 |
| GTAAAGACGC | AATTATTAAC | ACTAATGGCT | TTACGGCTTC | TACGCTAGAC | ATTTCTAACG | 1320 |
| AAAACATCAA | GGCGCGTAAT | TTCACCTTCG | AGCAAACCAA | AGATAAAGCG | CTCGCTGAAA | 1380 |
| TTGTGAATCA | CGGTTTAATT | ACTGTCGGTA | AGACGGCAG | TGTAAATCTT | ATTGGTGGCA | 1440 |
| AAGTGAAAAA | CGAGGGTGTG | ATTAGCGTAA | ATGGTGGCAG | CATTTCTTTA | CTCGCAGGGC | 1500 |
| AAAAAATCAC | CATCAGCGAT | ATAATAAACC | CAACCATTAC | TTACAGCATT | GCCGCGCCTG | 1560 |
| AAAATGAAGC | GGTCAATCTG | GGCGATATTT | TTGCCAAAGG | CGGTAACATT | AATGTCCGTG | 1620 |
| CTGCCACTAT | TCGAAACCAA | GGTAAACTTT | CTGCTGATTC | TGTAAGCAAA | GATAAAAGCG | 1680 |
| GCAATATTGT | TCTTTCCGCC | AAAGAGGGTG | AAGCGGAAAT | TGGCGGTGTA | ATTTCCGCTC | 1740 |
| AAAATCAGCA | AGCTAAAGGC | GGCAAGCTGA | TGATAAAGTC | CGATAAAGTC | ACATTAAAAA | 1800 |
| CAGGTGCAGT | TATCGACCTT | TCAGGTAAAG | AAGGGGGAGA | AACTTACCTT | GGCGGTGACG | 1860 |
| AGCGCGGCGA | AGGTAAAAAC | GGCATTCAAT | TAGCAAAGAA | AACCTCTTTA | GAAAAAGGCT | 1920 |
| CAACCATCAA | TGTATCAGGC | AAAGAAAAG | GCGGACGCGC | TATTGTGTGG | GGCGATATTG | 1980 |
| CGTTAATTGA | CGGCAATATT | AACGCTCAAG | GTAGTGGTGA | TATCGCTAAA | ACCGGTGGTT | 2040 |
| TTGTGGAGAC | ATCGGGGCAT | TATTTATCCA | TTGACAGCAA | TGCAATTGTT | AAAACAAAAG | 2100 |
| AGTGGTTGCT | AGACCCTGAT | GATGTAACAA | TTGAAGCCGA | AGACCCCTT | CGCAATAATA | 2160 |
| CCGGTATAAA | TGATGAATTC | CCAACAGGCA | CCGGTGAAGC | AAGCGACCCT | AAAAAAAATA | 2220 |
| GCGAACTCAA | AACAACGCTA | ACCAATACAA | CTATTTCAAA | TTATCTGAAA | AACGCCTGGA | 2280 |
| CAATGAATAT | AACGGCATCA | AGAAAACTTA | CCGTTAATAG | CTCAATCAAC | ATCGGAAGCA | 2340 |
| ACTCCCACTT | AATTCTCCAT | AGTAAAGGTC | AGCGTGGCGG | AGGCGTTCAG | ATTGATGGAG | 2400 |
| ATATTACTTC | TAAAGGCGGA | AATTTAACCA | TTTATTCTGG | CGGATGGGTT | GATGTTCATA | 2460 |
| AAAATATTAC | GCTTGATCAG | GGTTTTTTAA | ATATTACCGC | CGCTTCCGTA | GCTTTTGAAG | 2520 |
| GTGGAAATAA | CAAAGCACGC | GACGCGGCAA | ATGCTAAAAT | TGTCGCCCAG | GGCACTGTAA | 2580 |
| CCATTACAGG | AGAGGGAAAA | GATTTCAGGG | CTAACAACGT | ATCTTTAAAC | GGAACGGGTA | 2640 |
| AAGGTCTGAA | TATCATTTCA | TCAGTGAATA | ATTTAACCCA | CAATCTTAGT | GGCACAATTA | 2700 |
| ACATATCTGG | GAATATAACA | ATTAACCAAA | CTACGAGAAA | GAACACCTCG | TATTGGCAAA | 2760 |
| CCAGCCATGA | TTCGCACTGG | AACGTCAGTG | CTCTTAATCT | AGAGACAGGC | GCAAATTTTA | 2820 |
| CCTTTATTAA | ATACATTTCA | AGCAATAGCA | AAGGCTTAAC | AACACAGTAT | AGAAGCTCTG | 2880 |
| CAGGGGTGAA | TTTTAACGGC | GTAAATGGCA | ACATGTCATT | CAATCTCAAA | GAAGGAGCGA | 2940 |

| | | | | | | |
|---|---|---|---|---|---|---|
| AAGTTAATTT | CAAATTAAAA | CCAAACGAGA | ACATGAACAC | AAGCAAACCT | TTACCAATTC | 3000 |
| GGTTTTTAGC | CAATATCACA | GCCACTGGTG | GGGGCTCTGT | TTTTTTTGAT | ATATATGCCA | 3060 |
| ACCATTCTGG | CAGAGGGGCT | GAGTTAAAAA | TGAGTGAAAT | TAATATCTCT | AACGGCGCTA | 3120 |
| ATTTTACCTT | AAATTCCCAT | GTTCGCGGCG | ATGACGCTTT | TAAAATCAAC | AAAGACTTAA | 3180 |
| CCATAAATGC | AACCAATTCA | AATTTCAGCC | TCAGACAGAC | GAAAGATGAT | TTTTATGACG | 3240 |
| GGTACGCACG | CAATGCCATC | AATTCAACCT | ACAACATATC | CATTCTGGGC | GGTAATGTCA | 3300 |
| CCCTTGGTGG | ACAAAACTCA | AGCAGCAGCA | TTACGGGGAA | TATTACTATC | GAGAAAGCAG | 3360 |
| CAAATGTTAC | GCTAGAAGCC | AATAACGCCC | CTAATCAGCA | AAACATAAGG | GATAGAGTTA | 3420 |
| TAAAACTTGG | CAGCTTGCTC | GTTAATGGGA | GTTAAGTTT | AACTGGCGAA | AATGCAGATA | 3480 |
| TTAAAGGCAA | TCTCACTATT | TCAGAAAGCG | CCACTTTTAA | AGGAAAGACT | AGAGATACCC | 3540 |
| TAAATATCAC | CGGCAATTTT | ACCAATAATG | GCACTGCCGA | AATTAATATA | ACACAAGGAG | 3600 |
| TGGTAAAACT | TGGCAATGTT | ACCAATGATG | GTGATTTAAA | CATTACCACT | CACGCTAAAC | 3660 |
| GCAACCAAAG | AAGCATCATC | GGCGGAGATA | TAATCAACAA | AAAGGAAGC | TTAAATATTA | 3720 |
| CAGACAGTAA | TAATGATGCT | GAAATCCAAA | TTGGCGGCAA | TATCTCGCAA | AAAGAAGGCA | 3780 |
| ACCTCACGAT | TTCTTCCGAT | AAAATTAATA | TCACCAAACA | GATAACAATC | AAAAAGGGTA | 3840 |
| TTGATGGAGA | GGACTCTAGT | TCAGATGCGA | CAAGTAATGC | CAACCTAACT | ATTAAAACCA | 3900 |
| AAGAATTGAA | ATTGACAGAA | GACCTAAGTA | TTTCAGGTTT | CAATAAAGCA | GAGATTACAG | 3960 |
| CCAAAGATGG | TAGAGATTTA | ACTATTGGCA | ACAGTAATGA | CGGTAACAGC | GGTGCCGAAG | 4020 |
| CCAAAACAGT | AACTTTTAAC | AATGTTAAAG | ATTCAAAAAT | CTCTGCTGAC | GGTCACAATG | 4080 |
| TGACACTAAA | TAGCAAAGTG | AAAACATCTA | GCAGCAATGG | CGGACGTGAA | AGCAATAGCG | 4140 |
| ACAACGATAC | CGGCTTAACT | ATTACTGCAA | AAAATGTAGA | AGTAAACAAA | GATATTACTT | 4200 |
| CTCTCAAAAC | AGTAAATATC | ACCGCGTCGG | AAAAGGTTAC | CACCACAGCA | GGCTCGACCA | 4260 |
| TTAACGCAAC | AAATGGCAAA | GCAAGTATTA | CAACCAAAAC | AGGTGATATC | AGCGGTACGA | 4320 |
| TTTCCGGTAA | CACGGTAAGT | GTTAGCGCGA | CTGGTGATTT | AACCACTAAA | TCCGGCTCAA | 4380 |
| AAATTGAAGC | GAAATCGGGT | GAGGCTAATG | TAACAAGTGC | AACAGGTACA | ATTGGCGGTA | 4440 |
| CAATTTCCGG | TAATACGGTA | AATGTTACGG | CAAACGCTGG | CGATTTAACA | GTTGGGAATG | 4500 |
| GCGCAGAAAT | TAATGCGACA | GAAGGAGCTG | CAACCTTAAC | CGCAACAGGG | AATACCTTGA | 4560 |
| CTACTGAAGC | CGGTTCTAGC | ATCACTTCAA | CTAAGGGTCA | GGTAGACCTC | TTGGCTCAGA | 4620 |
| ATGGTAGCAT | CGCAGGAAGC | ATTAATGCTG | CTAATGTGAC | ATTAAATACT | ACAGGCACCT | 4680 |
| TAACCACCGT | GGCAGGCTCG | GATATTAAAG | CAACCAGCGG | CACCTTGGTT | ATTAACGCAA | 4740 |
| AAGATGCTAA | GCTAAATGGT | GATGCATCAG | GTGATAGTAC | AGAAGTGAAT | GCAGTCAACG | 4800 |
| ACTGGGGATT | TGGTAGTGTG | ACTGCGGCAA | CCTCAAGCAG | TGTGAATATC | ACTGGGGATT | 4860 |
| TAAACACAGT | AAATGGGTTA | AATATCATTT | CGAAAGATGG | TAGAAACACT | GTGCGCTTAA | 4920 |
| GAGGCAAGGA | AATTGAGGTG | AAATATATCC | AGCCAGGTGT | AGCAAGTGTA | GAAGAAGTAA | 4980 |
| TTGAAGCGAA | ACGCGTCCTT | GAAAAAGTAA | AAGATTTATC | TGATGAAGAA | AGAGAAACAT | 5040 |
| TAGCTAAACT | TGGTGTAAGT | GCTGTACGTT | TTGTTGAGCC | AAATAATACA | ATTACAGTCA | 5100 |
| ATACACAAAA | TGAATTTACA | ACCAGACCGT | CAAGTCAAGT | GATAATTTCT | GAAGGTAAGG | 5160 |
| CGTGTTTCTC | AAGTGGTAAT | GGCGCACGAG | TATGTACCAA | TGTTGCTGAC | GATGGACAGC | 5220 |
| CGTAGTCAGT | AATTGACAAG | GTAGATTTCA | TCCTGCAATG | AAGTCATTTT | ATTTTCGTAT | 5280 |
| TATTTACTGT | GTGGGTTAAA | GTTCAGTACG | GGCTTTACCC | ATCTTGTAAA | AAATTACGGA | 5340 |

-continued

| | | | | | | |
|---|---|---|---|---|---|---|
| GAATACAATA | AAGTATTTTT | AACAGGTTAT | TATTATGAAA | AATATAAAAA | GCAGATTAAA | 5400 |
| ACTCAGTGCA | ATATCAGTAT | TGCTTGGCCT | GGCTTCTTCA | TCATTGTATG | CAGAAGAAGC | 5460 |
| GTTTTTAGTA | AAAGGCTTTC | AGTTATCTGG | TGCACTTGAA | ACTTAAGTG | AAGACGCCCA | 5520 |
| ACTGTCTGTA | GCAAAATCTT | TATCTAAATA | CCAAGGCTCG | CAAACTTTAA | CAAACCTAAA | 5580 |
| AACAGCACAG | CTTGAATTAC | AGGCTGTGCT | AGATAAGATT | GAGCCAAATA | AATTTGATGT | 5640 |
| GATATTGCCG | CAACAAACCA | TTACGGATGG | CAATATCATG | TTTGAGCTAG | TCTCGAAATC | 5700 |
| AGCCGCAGAA | AGCCAAGTTT | TTTATAAGGC | GAGCCAGGGT | TATAGTGAAG | AAAATATCGC | 5760 |
| TCGTAGCCTG | CCATCTTTGA | AACAAGGAAA | AGTGTATGAA | GATGGTCGTC | AGTGGTTCGA | 5820 |
| TTTGCGTGAA | TTTAATATGG | CAAAAGAAAA | CCCGCTTAAG | GTTACCCGTG | TACATTACGA | 5880 |
| ACTAAACCCT | AAAAACAAAA | CCTCTAATTT | GATAATTGCG | GGCTTCTCGC | CTTTTGGTAA | 5940 |
| AACGCGTAGC | TTTATTTCTT | ATGATAATTT | CGGCGCGAGA | GAGTTTAACT | ACCAACGTGT | 6000 |
| AAGCTTGGGT | TTTGTTAATG | CCAATTTAAC | TGGTCATGAT | GATGTGTTAA | TTATACCAGT | 6060 |
| ATGAGTTATG | CTGATTCTAA | TGATATCGAC | GGCTTACCAA | GTGCGATTAA | TCGTAAATTA | 6120 |
| TCAAAAGGTC | AATCTATCTC | TGCGAATCTG | AAATGGAGTT | ATTATCTCCC | AACATTTAAC | 6180 |
| CTTGGCATGG | AAGACCAATT | TAAAATTAAT | TTAGGCTACA | ACTACCGCCA | TATTAATCAA | 6240 |
| ACCTCCGCGT | TAAATCGCTT | GGGTGAAACG | AAGAAAAAAT | TTGCAGTATC | AGGCGTAAGT | 6300 |
| GCAGGCATTG | ATGGACATAT | CCAATTTACC | CCTAAAACAA | TCTTTAATAT | TGATTTAACT | 6360 |
| CATCATTATT | ACGCGAGTAA | ATTACCAGGC | TCTTTTGGAA | TGGAGCGCAT | TGGCGAAACA | 6420 |
| TTTAATCGCA | GCTATCACAT | TAGCACAGCC | AGTTTAGGGT | TGAGTCAAGA | GTTTGCTCAA | 6480 |
| GGTTGGCATT | TTAGCAGTCA | ATTATCAGGT | CAATTTACTC | TACAAGATAT | TAGCAGTATA | 6540 |
| GATTTATTCT | CTGTAACAGG | TACTTATGGC | GTCAGAGGCT | TTAAATACGG | CGGTGCAAGT | 6600 |
| GGTGAGCGCG | GTCTTGTATG | GCGTAATGAA | TTAAGTATGC | CAAAATACAC | CCGCTTCCAA | 6660 |
| ATCAGCCCTT | ATGCGTTTTA | TGATGCAGGT | CAGTTCCGTT | ATAATAGCGA | AAATGCTAAA | 6720 |
| ACTTACGGCG | AAGATATGCA | CACGGTATCC | TCTGCGGGTT | TAGGCATTAA | AACCTCTCCT | 6780 |
| ACACAAAACT | TAAGCCTAGA | TGCTTTTGTT | GCTCGTCGCT | TTGCAAATGC | CAATAGTGAC | 6840 |
| AATTTGAATG | GCAACAAAAA | ACGCACAAGC | TCACCTACAA | CCTTCTGGGG | GAGATTAACA | 6900 |
| TTCAGTTTCT | AACCCTGAAA | TTTAATCAAC | TGGTAAGCGT | TCCGCCTACC | AGTTTATAAC | 6960 |
| TATATGCTTT | ACCCGCCAAT | TTACAGTCTA | TAGGCAACCC | TGTTTTACC | CTTATATATC | 7020 |
| AAATAAACAA | GCTAAGCTGA | GCTAAGCAAA | CCAAGCAAAC | TCAAGCAAGC | CAAGTAATAC | 7080 |
| TAAAAAACA | ATTTATATGA | TAAACTAAAG | TATACTCCAT | GCCATGGCGA | TACAAGGGAT | 7140 |
| TTAATAATAT | GACAAAAGAA | AATTTGCAAA | ACGCTCCTCA | AGATGCGACC | GCTTTACTTG | 7200 |
| CGGAATTAAG | CAACAATCAA | ACTCCCCTGC | GAATATTTAA | ACAACCACGC | AAGCCCAGCC | 7260 |
| TATTACGCTT | GGAACAACAT | ATCGCAAAAA | AAGATTATGA | GTTTGCTTGT | CGTGAATTAA | 7320 |
| TGGTGATTCT | GGAAAAAATG | GACGCTAATT | TTGGAGGCGT | TCACGATATT | GAATTTGACG | 7380 |
| CACCCGCTCA | GCTGGCATAT | CTACCCGAAA | AATTACTAAT | TTATTTTGCC | ACTCGTCTCG | 7440 |
| CTAATGCAAT | TACAACACTC | TTTTCCGACC | CCGAATTGGC | AATTTCTGAA | GAAGGGGCGT | 7500 |
| TAAAGATGAT | TAGCCTGCAA | CGCTGGTTGA | CGCTGATTTT | TGCCTCTTCC | CCCTACGTTA | 7560 |
| ACGCAGACCA | TATTCTCAAT | AAATATAATA | TCAACCCAGA | TTCCGAAGGT | GGCTTTCATT | 7620 |
| TAGCAACAGA | CAACTCTTCT | ATTGCTAAAT | TCTGTATTTT | TTACTTACCC | GAATCCAATG | 7680 |
| TCAATATGAG | TTTAGATGCG | TTATGGGCAG | GGAATCAACA | ACTTTGTGCT | TCATTGTGTT | 7740 |

| | | | | | | |
|---|---|---|---|---|---|---|
| TTGCGTTGCA | GTCTTCACGT | TTTATTGGTA | CCGCATCTGC | GTTTCATAAA | AGAGCGGTGG | 7800 |
| TTTTACAGTG | GTTTCCTAAA | AAACTCGCCG | AAATTGCTAA | TTTAGATGAA | TTGCCTGCAA | 7860 |
| ATATCCTTCA | TGATGTATAT | ATGCACTGCA | GTTATGATTT | AGCAAAAAAC | AAGCACGATG | 7920 |
| TTAAGCGTCC | ATTAAACGAA | CTTGTCCGCA | AGCATATCCT | CACGCAAGGA | TGGCAAGACC | 7980 |
| GCTACCTTTA | CACCTTAGGT | AAAAAGGACG | GCAAACCTGT | GATGATGGTA | CTGCTTGAAC | 8040 |
| ATTTTAATTC | GGGACATTCG | ATTTATCGTA | CACATTCAAC | TTCAATGATT | GCTGCTCGAG | 8100 |
| AAAAATTCTA | TTTAGTCGGC | TTAGGCCATG | AGGGCGTTGA | TAAAATAGGT | CGAGAAGTGT | 8160 |
| TTGACGAGTT | CTTTGAAATC | AGTAGCAATA | ATATAATGGA | GAGACTGTTT | TTTATCCGTA | 8220 |
| AACAGTGCGA | AACTTTCCAA | CCCGCAGTGT | TCTATATGCC | AAGCATTGGC | ATGGATATTA | 8280 |
| CCACGATTTT | TGTGAGCAAC | ACTCGGCTTG | CCCCTATTCA | AGCTGTAGCC | CTGGGTCATC | 8340 |
| CTGCCACTAC | GCATTCTGAA | TTTATTGATT | ATGTCATCGT | AGAAGATGAT | TATGTGGGCA | 8400 |
| GTGAAGATTG | TTTCAGCGAA | ACCCTTTTAC | GCTTACCCAA | AGATGCCCTA | CCTTATGTAC | 8460 |
| CTTCTGCACT | CGCCCCACAA | AAAGTGGATT | ATGTACTCAG | GGAAAACCCT | GAAGTAGTCA | 8520 |
| ATATCGGTAT | TGCCGCTACC | ACAATGAAAT | TAAACCCTGA | ATTTTGCTA | ACATTGCAAG | 8580 |
| AAATCAGAGA | TAAAGCTAAA | GTCAAAATAC | ATTTTCATTT | CGCACTTGGA | CAATCAACAG | 8640 |
| GCTTGACACA | CCCTTATGTC | AAATGGTTTA | TCGAAAGCTA | TTTAGGTGAC | GATGCCACTG | 8700 |
| CACATCCCCA | CGCACCTTAT | CACGATTATC | TGGCAATATT | GCGTGATTGC | GATATGCTAC | 8760 |
| TAAATCCGTT | TCCTTTCGGT | AATACTAACG | GCATAATTGA | TATGGTTACA | TTAGGTTTAG | 8820 |
| TTGGTGTATG | CAAAACGGGG | GATGAAGTAC | ATGAACATAT | TGATGAAGGT | CTGTTTAAAC | 8880 |
| GCTTAGGACT | ACCAGAATGG | CTGATAGCCG | ACACACGAGA | AACATATATT | GAATGTGCTT | 8940 |
| TGCGTCTAGC | AGAAAACCAT | CAAGAACGCC | TTGAACTCCG | TCGTTACATC | ATAGAAAACA | 9000 |
| ACGGCTTACA | AAAGCTTTTT | ACAGGCGACC | CTCGTCCATT | GGGCAAAATA | CTGCTTAAGA | 9060 |
| AAACAAATGA | ATGGAAGCGG | AAGCACTTGA | GTAAAAAATA | ACGGTTTTTT | AAAGTAAAAG | 9120 |
| TGCGGTTAAT | TTTCAAAGCG | TTTTAAAAAC | CTCTCAAAAA | TCAACCGCAC | TTTTATCTTT | 9180 |
| ATAACGATCC | CGCACGCTGA | CAGTTTATCA | GCCTCCCGCC | ATAAAACTCC | GCCTTTCATG | 9240 |
| GCGGAGATTT | TAGCCAAAAC | TGGCAGAAAT | TAAAGGCTAA | AATCACCAAA | TTGCACCACA | 9300 |
| AAATCACCAA | TACCCACAAA | AAA | | | | 9323 |

(2) INFORMATION FOR SEQ ID NO:7:

(i) SEQUENCE CHARACTERISTICS:
        (A) LENGTH: 4287 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

| | | | | | | |
|---|---|---|---|---|---|---|
| GATCAATCTG | GGCGATATTT | TTGCCAAAGG | TGGTAACATT | AATGTCCGCG | CTGCCACTAT | 60 |
| TCGCAATAAA | GGTAAACTTT | CTGCCGACTC | TGTAAGCAAA | GATAAAGTG | GTAACATTGT | 120 |
| TCTCTCTGCC | AAAGAAGGTG | AAGCGGAAAT | TGGCGGTGTA | ATTTCCGCTC | AAAATCAGCA | 180 |
| AGCCAAAGGT | GGTAAGTTGA | TGATTACAGG | CGATAAAGTT | ACATTGAAAA | CGGGTGCACT | 240 |
| TATCGACCTT | TCGGGTAAAG | AAGGGGGAGA | AACTTATCTT | GGCGGTGACG | AGCGTGGCGA | 300 |
| AGGTAAAAAC | GGCATTCAAT | TAGCAAAGAA | AACCACTTTA | GAAAAAGGCT | CAACAATTAA | 360 |
| TGTGTCAGGT | AAAGAAAAAG | CTGGGCGCGC | TATTGTATGG | GGCGATATTG | CGTTAATTGA | 420 |

```
CGGCAATATT  AATGCCCAAG  GTAAAGATAT  CGCTAAAACT  GGTGGTTTTG  TGGAGACGTC   480
GGGGCATTAC  TTATCCATTG  ATGATAACGC  AATTGTTAAA  ACAAAGAAT   GGCTACTAGA   540
CCCAGAGAAT  GTGACTATTG  AAGCTCCTTC  CGCTTCTCGC  GTCGAGCTGG  GTGCCGATAG   600
GAATTCCCAC  TCGGCAGAGG  TGATAAAAGT  GACCCTAAAA  AAAATAACA   CCTCCTTGAC   660
AACACTAACC  AATACAACCA  TTTCAAATCT  TCTGAAAAGT  GCCCACGTGG  TGAACATAAC   720
GGCAAGGAGA  AAACTTACCG  TTAATAGCTC  TATCAGTATA  GAAAGAGGCT  CCCACTTAAT   780
TCTCCACAGT  GAAGGTCAGG  GCGGTCAAGG  TGTTCAGATT  GATAAAGATA  TTACTTCTGA   840
AGGCGGAAAT  TTAACCATTT  ATTCTGGCGG  ATGGGTTGAT  GTTCATAAAA  ATATTACGCT   900
TGGTAGCGGC  TTTTTAAACA  TCACAACTAA  AGAAGGAGAT  ATCGCCTTCG  AAGACAAGTC   960
TGGACGGAAC  AACCTAACCA  TTACAGCCCA  AGGGACCATC  ACCTCAGGTA  ATAGTAACGG  1020
CTTTAGATTT  AACAACGTCT  CTCTAAACAG  CCTTGGCGGA  AAGCTGAGCT  TTACTGACAG  1080
CAGAGAGGAC  AGAGGTAGAA  GAACTAAGGG  TAATATCTCA  AACAAATTTG  ACGGAACGTT  1140
AAACATTTCC  GGAACTGTAG  ATATCTCAAT  GAAAGCACCC  AAAGTCAGCT  GGTTTTACAG  1200
AGACAAAGGA  CGCACCTACT  GGAACGTAAC  CACTTTAAAT  GTTACCTCGG  GTAGTAAATT  1260
TAACCTCTCC  ATTGACAGCA  CAGGAAGTGG  CTCAACAGGT  CCAAGCATAC  GCAATGCAGA  1320
ATTAAATGGC  ATAACATTTA  ATAAAGCCAC  TTTTAATATC  GCACAAGGCT  CAACAGCTAA  1380
CTTTAGCATC  AAGGCATCAA  TAATGCCCTT  TAAGAGTAAC  GCTAACTACG  CATTATTTAA  1440
TGAAGATATT  TCAGTCTCAG  GGGGGGGTAG  CGTTAATTTC  AAACTTAACG  CCTCATCTAG  1500
CAACATACAA  ACCCCTGGCG  TAATTATAAA  ATCTCAAAAC  TTTAATGTCT  CAGGAGGGTC  1560
AACTTTAAAT  CTCAAGGCTG  AAGGTTCAAC  AGAAACCGCT  TTTTCAATAG  AAAATGATTT  1620
AAACTTAAAC  GCCACCGGTG  GCAATATAAC  AATCAGACAA  GTCGAGGGTA  CCGATTCACG  1680
CGTCAACAAA  GGTGTCGCAG  CCAAAAAAAA  CATAACTTTT  AAGGGGGTA   ATATCACCTT  1740
CGGCTCTCAA  AAAGCCACAA  CAGAAATCAA  AGGCAATGTT  ACCATCAATA  AAAACACTAA  1800
CGCTACTCTT  CGTGGTGCGA  ATTTTGCCGA  AAACAAATCG  CCTTTAAATA  TAGCAGGAAA  1860
TGTTATTAAT  AATGGCAACC  TTACCACTGC  CGGCTCCATT  ATCAATATAG  CCGGAAATCT  1920
TACTGTTTCA  AAAGGCGCTA  ACCTTCAAGC  TATAACAAAT  TACACTTTTA  ATGTAGCCGG  1980
CTCATTTGAC  AACAATGGCG  CTTCAAACAT  TTCCATTGCC  AGAGGAGGGG  CTAAATTTAA  2040
AGATATCAAT  AACACCAGTA  GCTTAAATAT  TACCACCAAC  TCTGATACCA  CTTACCGCAC  2100
CATTATAAAA  GGCAATATAT  CCAACAAATC  AGGTGATTTG  AATATTATTG  ATAAAAAAG   2160
CGACGCTGAA  ATCCAAATTG  GCGGCAATAT  CTCACAAAAA  GAAGGCAATC  TCACAATTTC  2220
TTCTGATAAA  GTAAATATTA  CCAATCAGAT  AACAATCAAA  GCAGGCGTTG  AAGGGGGGCG  2280
TTCTGATTCA  AGTGAGGCAG  AAAATGCTAA  CCTAACTATT  CAAACCAAAG  AGTTAAAATT  2340
GGCAGGAGAC  CTAAATATTT  CAGGCTTTAA  TAAAGCAGAA  ATTACAGCTA  AAAATGGCAG  2400
TGATTTAACT  ATTGGCAATG  CTAGCGGTGG  TAATGCTGAT  GCTAAAAAAG  TGACTTTTGA  2460
CAAGGTTAAA  GATTCAAAAA  TCTCGACTGA  CGGTCACAAT  GTAACACTAA  ATAGCGAAGT  2520
GAAACGTCT   AATGGTAGTA  GCAATGCTGG  TAATGATAAC  AGCACCGGTT  TAACCATTTC  2580
CGCAAAAGAT  GTAACGGTAA  ACAATAACGT  TACCTCCCAC  AAGACAATAA  ATATCTCTGC  2640
CGCAGCAGGA  AATGTAACAA  CCAAAGAAGG  CACAACTATC  AATGCAACCA  CAGGCAGCGT  2700
GGAAGTAACT  GCTCAAAATG  GTACAATTAA  AGGCAACATT  ACCTCGCAAA  ATGTAACAGT  2760
GACAGCAACA  GAAAATCTTG  TTACCACAGA  GAATGCTGTC  ATTAATGCAA  CCAGCGGCAC  2820
```

| | | | | | | |
|---|---|---|---|---|---|---|
| AGTAAACATT | AGTACAAAAA | CAGGGGATAT | TAAAGGTGGA | ATTGAATCAA | CTTCCGGTAA | 2880 |
| TGTAAATATT | ACAGCGAGCG | GCAATACACT | TAAGGTAAGT | AATATCACTG | GTCAAGATGT | 2940 |
| AACAGTAACA | GCGGATGCAG | GAGCCTTGAC | AACTACAGCA | GGCTCAACCA | TTAGTGCGAC | 3000 |
| AACAGGCAAT | GCAAATATTA | CAACCAAAAC | AGGTGATATC | AACGGTAAAG | TTGAATCCAG | 3060 |
| CTCCGGCTCT | GTAACACTTG | TTGCAACTGG | AGCAACTCTT | GCTGTAGGTA | ATATTTCAGG | 3120 |
| TAACACTGTT | ACTATTACTG | CGGATAGCGG | TAAATTAACC | TCCACAGTAG | GTTCTACAAT | 3180 |
| TAATGGGACT | AATAGTGTAA | CCACCTCAAG | CCAATCAGGC | GATATTGAAG | GTACAATTTC | 3240 |
| TGGTAATACA | GTAAATGTTA | CAGCAAGCAC | TGGTGATTTA | ACTATTGGAA | ATAGTGCAAA | 3300 |
| AGTTGAAGCG | AAAAATGGAG | CTGCAACCTT | AACTGCTGAA | TCAGGCAAAT | TAACCACCCA | 3360 |
| AACAGGCTCT | AGCATTACCT | CAAGCAATGG | TCAGACAACT | CTTACAGCCA | AGGATAGCAG | 3420 |
| TATCGCAGGA | AACATTAATG | CTGCTAATGT | GACGTTAAAT | ACCACAGGCA | CTTTAACTAC | 3480 |
| TACAGGGGAT | TCAAAGATTA | ACGCAACCAG | TGGTACCTTA | ACAATCAATG | CAAAAGATGC | 3540 |
| CAAATTAGAT | GGTGCTGCAT | CAGGTGACCG | CACAGTAGTA | AATGCAACTA | ACGCAAGTGG | 3600 |
| CTCTGGTAAC | GTGACTGCGA | AAACCTCAAG | CAGCGTGAAT | ATCACCGGGG | ATTTAAACAC | 3660 |
| AATAAATGGG | TTAAATATCA | TTTCGGAAAA | TGGTAGAAAC | ACTGTGCGCT | TAAGAGGCAA | 3720 |
| GGAAATTGAT | GTGAAATATA | TCCAACCAGG | TGTAGCAAGC | GTAGAAGAGG | TAATTGAAGC | 3780 |
| GAAACGCGTC | CTTGAGAAGG | TAAAAGATTT | ATCTGATGAA | GAAAGAGAAA | CACTAGCCAA | 3840 |
| ACTTGGTGTA | AGTGCTGTAC | GTTTCGTTGA | GCCAAATAAT | GCCATTACGG | TTAATACACA | 3900 |
| AAACGAGTTT | ACAACCAAAC | CATCAAGTCA | AGTGACAATT | TCTGAAGGTA | AGGCGTGTTT | 3960 |
| CTCAAGTGGT | AATGGCGCAC | GAGTATGTAC | CAATGTTGCT | GACGATGGAC | AGCAGTAGTC | 4020 |
| AGTAATTGAC | AAGGTAGATT | TCATCCTGCA | ATGAAGTCAT | TTTATTTTCG | TATTATTTAC | 4080 |
| TGTGTGGGTT | AAAGTTCAGT | ACGGGCTTTA | CCCACCTTGT | AAAAAATTAC | GAAAAATACA | 4140 |
| ATAAAGTATT | TTTAACAGGT | TATTATTATG | AAAAACATAA | AAAGCAGATT | AAAACTCAGT | 4200 |
| GCAATATCAA | TATTGCTTGG | CTTGGCTTCT | TCATCGACGT | ATGCAGAAGA | AGCGTTTTTA | 4260 |
| GTAAAAGGCT | TTCAGTTATC | TGGCGCG | | | | 4287 |

( 2 ) INFORMATION FOR SEQ ID NO:8:

( i ) SEQUENCE CHARACTERISTICS:
        ( A ) LENGTH: 4702 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

| | | | | | | |
|---|---|---|---|---|---|---|
| GGGAATGAGC | GTCGTACACG | GTACAGCAAC | CATGCAAGTA | GACGGCAATA | AAACCACTAT | 60 |
| CCGTAATAGC | ATCAATGCTA | TCATCAATTG | GAAACAATTT | AACATTGACC | AAAATGAAAT | 120 |
| GGAGCAGTTT | TTACAAGAAA | GCAGCAACTC | TGCCGTTTTC | AACCGTGTTA | CATCTGACCA | 180 |
| AATCTCCCAA | TTAAAAGGGA | TTTTAGATTC | TAACGGACAA | GTCTTTTTAA | TCAACCCAAA | 240 |
| TGGTATCACA | ATAGGTAAAG | ACGCAATTAT | TAACACTAAT | GGCTTACTG | CTTCTACGCT | 300 |
| AGACATTTCT | AACGAAAACA | TCAAGGCGCG | TAATTTCACC | CTTGAGCAAA | CCAAGGATAA | 360 |
| AGCACTCGCT | GAAATCGTGA | ATCACGGTTT | AATTACCGTT | GGTAAAGACG | GTAGCGTAAA | 420 |
| CCTTATTGGT | GGCAAAGTGA | AAAACGAGGG | CGTGATTAGC | GTAAATGGCG | GTAGTATTTC | 480 |

```
TTTACTTGCA GGGCAAAAAA TCACCATCAG CGATATAATA AATCCAACCA TCACTTACAG      540
CATTGCTGCA CCTGAAAACG AAGCGATCAA TCTGGGCGAT ATTTTTGCCA AAGGTGGTAA      600
CATTAATGTC CGCGCTGCCA CTATTCGCAA TAAAGGTAAA CTTTCTGCCG ACTCTGTAAG      660
CAAAGATAAA AGTGGTAACA TTGTTCTCTC TGCCAAAGAA GGTGAAGCGG AAATTGGCGG      720
TGTAATTTCC GCTCAAAATC AGCAAGCCAA AGGTGGTAAG TTGATGATTA CAGGTGATAA      780
AGTCACATTA AAAACAGGTG CAGTTATCGA CCTTTCAGGT AAAGAAGGGG GAGAGACTTA      840
TCTTGGCGGT GATGAGCGTG GCGAAGGTAA AAATGGTATT CAATTAGCGA AGAAAACCTC      900
TTTAGAAAAA GGCTCGACAA TTAATGTATC AGGCAAAGAA AAAGGCGGGC GCGCTATTGT      960
ATGGGGCGAT ATTGCATTAA TTAATGGTAA CATTAATGCT CAAGGTAGCG ATATTGCTAA     1020
AACTGGCGGC TTTGTGGAAA CATCAGGACA TGACTTATCC ATTGGTGATG ATGTGATTGT     1080
TGACGCTAAA GAGTGGTTAT TAGACCCAGA TGATGTGTCC ATTGAAACTC TTACATCTGG     1140
ACGCAATAAT ACCGGCGAAA ACCAAGGATA TACAACAGGA GATGGGACTA AAGAGTCACC     1200
TAAAGGTAAT AGTATTTCTA AACCTACATT AACAAACTCA ACTCTTGAGC AAATCCTAAG     1260
AAGAGGTTCT TATGTTAATA TCACTGCTAA TAATAGAATT TATGTTAATA GCTCCATCAA     1320
CTTATCTAAT GGCAGTTTAA CACTTCACAC TAAACGAGAT GGAGTTAAAA TTAACGGTGA     1380
TATTACCTCA AACGAAAATG GTAATTTAAC CATTAAAGCA GGCTCTTGGG TTGATGTTCA     1440
TAAAAACATC ACGCTTGGTA CGGGTTTTTT CAATATTGTC GCTGGGGATT CTGTAGCTTT     1500
TGAGAGAGAG GGCGATAAAG CACGTAACGC AACAGATGCT CAAATTACCG CACAAGGGAC     1560
GATAACCGTC AATAAGATG ATAAACAATT TAGATTCAAT AATGTATCTA TTAACGGGAC     1620
GGGCAAGGGT TTAAAGTTTA TTGCAAATCA AAATAATTTC ACTCATAAAT TGATGGCGA     1680
AATTAACATA TCTGGAATAG TAACAATTAA CCAAACCACG AAAAAAGATG TTAAATACTG     1740
GAATGCATCA AAAGACTCTT ACTGGAATGT TTCTTCTCTT ACTTTGAATA CGGTGCAAAA     1800
ATTTACCTTT ATAAAATTCG TTGATAGCGG CTCAAATTCC CAAGATTTGA GGTCATCACG     1860
TAGAAGTTTT GCAGGCGTAC ATTTTAACGG CATCGGAGGC AAAACAAACT TCAACATCGG     1920
AGCTAACGCA AAAGCCTTAT TTAAATTAAA ACCAAACGCC GCTACAGACC CAAAAAAAGA     1980
ATTACCTATT ACTTTTAACG CCAACATTAC AGCTACCGGT AACAGTGATA GCTCTGTGAT     2040
GTTTGACATA CACGCCAATC TTACCTCTAG AGCTGCCGGC ATAAACATGG ATTCAATTAA     2100
CATTACCGGC GGGCTTGACT TTTCCATAAC ATCCATAAT CGCAATAGTA ATGCTTTTGA     2160
AATCAAAAAA GACTTAACTA TAAATGCAAC TGGCTCGAAT TTTAGTCTTA AGCAAACGAA     2220
AGATTCTTTT TATAATGAAT ACAGCAAACA CGCCATTAAC TCAAGTCATA ATCTAACCAT     2280
TCTTGGCGGC AATGTCACTC TAGGTGGGGA AAATTCAAGC AGTAGCATTA CGGGCAATAT     2340
CAATATCACC AATAAAGCAA ATGTTACATT ACAAGCTGAC ACCAGCAACA GCAACACAGG     2400
CTTGAAGAAA AGAACTCTAA CTCTTGGCAA TATATCTGTT GAGGGGAATT TAAGCCTAAC     2460
TGGTGCAAAT GCAAACATTG TCGGCAATCT TTCTATTGCA GAAGATTCCA CATTTAAAGG     2520
AGAAGCCAGT GACAACCTAA ACATCACCGG CACCTTTACC AACAACGGTA CCGCCAACAT     2580
TAATATAAAA CAAGGAGTGG TAAAACTCCA AGGCGATATT ATCAATAAAG GTGGTTTAAA     2640
TATCACTACT AACGCCTCAG GCACTCAAAA AACCATTATT AACGGAAATA TAACTAACGA     2700
AAAAGGCGAC TTAAACATCA AGAATATTAA AGCCGACGCC GAAATCCAAA TTGGCGGCAA     2760
TATCTCACAA AAAGAAGGCA ATCTCACAAT TTCTTCTGAT AAAGTAAATA TTACCAATCA     2820
GATAACAATC AAAGCAGGCG TTGAAGGGGG GCGTTCTGAT TCAAGTGAGG CAGAAAATGC     2880
```

-continued

| | | | | | | |
|---|---|---|---|---|---|---|
| TAACCTAACT | ATTCAAACCA | AAGAGTTAAA | ATTGGCAGGA | GACCTAAATA | TTTCAGGCTT | 2940 |
| TAATAAAGCA | GAAATTACAG | CTAAAAATGG | CAGTGATTTA | ACTATTGGCA | ATGCTAGCGG | 3000 |
| TGGTAATGCT | GATGCTAAAA | AAGTGACTTT | TGACAAGGTT | AAAGATTCAA | AAATCTCGAC | 3060 |
| TGACGGTCAC | AATGTAACAC | TAAATAGCGA | AGTGAAAACG | TCTAATGGTA | GTAGCAATGC | 3120 |
| TGGTAATGAT | AACAGCACCG | GTTAACCAT | TTCCGCAAAA | GATGTAACGG | TAAACAATAA | 3180 |
| CGTTACCTCC | CACAAGACAA | TAAATATCTC | TGCCGCAGCA | GGAAATGTAA | CAACCAAAGA | 3240 |
| AGGCACAACT | ATCAATGCAA | CCACAGGCAG | CGTGGAAGTA | ACTGCTCAAA | ATGGTACAAT | 3300 |
| TAAAGGCAAC | ATTACCTCGC | AAAATGTAAC | AGTGACAGCA | ACAGAAAATC | TTGTTACCAC | 3360 |
| AGAGAATGCT | GTCATTAATG | CAACCAGCGG | CACAGTAAAC | ATTAGTACAA | AAACAGGGGA | 3420 |
| TATTAAAGGT | GGAATTGAAT | CAACTTCCGG | TAATGTAAAT | ATTACAGCGA | GCGGCAATAC | 3480 |
| ACTTAAGGTA | AGTAATATCA | CTGGTCAAGA | TGTAACAGTA | ACAGCGGATG | CAGGAGCCTT | 3540 |
| GACAACTACA | GCAGGCTCAA | CCATTAGTGC | GACAACAGGC | AATGCAAATA | TTACAACCAA | 3600 |
| AACAGGTGAT | ATCAACGGTA | AAGTTGAATC | CAGCTCCGGC | TCTGTAACAC | TTGTTGCAAC | 3660 |
| TGGAGCAACT | CTTGCTGTAG | GTAATATTTC | AGGTAACACT | GTTACTATTA | CTGCGGATAG | 3720 |
| CGGTAAATTA | ACCTCCACAG | TAGGTTCTAC | AATTAATGGG | ACTAATAGTG | TAACCACCTC | 3780 |
| AAGCCAATCA | GGCGATATTG | AAGGTACAAT | TTCTGGTAAT | ACAGTAAATG | TTACAGCAAG | 3840 |
| CACTGGTGAT | TTAACTATTG | GAAATAGTGC | AAAAGTTGAA | GCGAAAAATG | GAGCTGCAAC | 3900 |
| CTTAACTGCT | GAATCAGGCA | AATTAACCAC | CCAAACAGGC | TCTAGCATTA | CCTCAAGCAA | 3960 |
| TGGTCAGACA | ACTCTTACAG | CCAAGGATAG | CAGTATCGCA | GGAAACATTA | ATGCTGCTAA | 4020 |
| TGTGACGTTA | AATACCACAG | GCACTTTAAC | TACTACAGGG | GATTCAAAGA | TTAACGCAAC | 4080 |
| CAGTGGTACC | TTAACAATCA | ATGCAAAGA | TGCCAAATTA | GATGGTGCTG | CATCAGGTGA | 4140 |
| CCGCACAGTA | GTAAATGCAA | CTAACGCAAG | TGGCTCTGGT | AACGTGACTG | CGAAAACCTC | 4200 |
| AAGCAGCGTG | AATATCACCG | GGGATTTAAA | CACAATAAAT | GGGTTAAATA | TCATTTCGGA | 4260 |
| AAATGGTAGA | AACACTGTGC | GCTTAAGAGG | CAAGGAAATT | GATGTGAAAT | ATATCCAACC | 4320 |
| AGGTGTAGCA | AGCGTAGAAG | AGGTAATTGA | AGCGAAACGC | GTCCTTGAGA | AGGTAAAAGA | 4380 |
| TTTATCTGAT | GAAGAAAGAG | AAACACTAGC | CAAACTTGGT | GTAAGTGCTG | TACGTTTCGT | 4440 |
| TGAGCCAAAT | AATGCCATTA | CGGTTAATAC | ACAAAACGAG | TTTACAACCA | AACCATCAAG | 4500 |
| TCAAGTGACA | ATTTCTGAAG | GTAAGGCGTG | TTTCTCAAGT | GGTAATGGCG | CACGAGTATG | 4560 |
| TACCAATGTT | GCTGACGATG | GACAGCAGTA | GTCAGTAATT | GACAAGGTAG | ATTTCATCCT | 4620 |
| GCAATGAAGT | CATTTTATTT | TCGTATTATT | TACTGTGTGG | GTTAAAGTTC | AGTACGGGCT | 4680 |
| TTACCCACCT | TGTAAAAAAT | TA | | | | 4702 |